US011345742B1

(12) United States Patent
Gauhar et al.

(10) Patent No.: US 11,345,742 B1
(45) Date of Patent: May 31, 2022

(54) SHARK VNARS FOR TREATING COVID-19

(71) Applicant: Ossianix, Inc., Philadelphia, PA (US)

(72) Inventors: Aziz Gauhar, Hitchin (GB); Cyril V. Privezentzev, Sawston (GB); Pawel Stocki, Royston (GB); Julia Lynn Rutkowski, Bryn Mawr, PA (US)

(73) Assignee: Ossianix, Inc., Philadelphia, PA (US)

( * ) Notice: Subject to any disclaimer, the term of this patent is extended or adjusted under 35 U.S.C. 154(b) by 0 days.

(21) Appl. No.: 17/343,444

(22) Filed: Jun. 9, 2021

Related U.S. Application Data

(60) Provisional application No. 63/197,601, filed on Jun. 7, 2021.

(51) Int. Cl.
*C07K 16/10* (2006.01)
*A61P 31/14* (2006.01)

(52) U.S. Cl.
CPC .............. *C07K 16/10* (2013.01); *A61P 31/14* (2018.01); *C07K 2317/569* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS 6,180,370 B1 * 1/2001 Queen ................ C07K 16/2866
435/69.6

FOREIGN PATENT DOCUMENTS

WO    WO-2017196847 A1 * 11/2017 ............. C07K 16/32

OTHER PUBLICATIONS

Stanfield et al., J Mol Biol. Mar. 23, 2007;367(2):358-72. doi: 10.1016/j.jmb.2006.12.045. Epub Dec. 22, 2006.*
Barelle et al., Antibodies 2015, 4, 240-258; doi:10.3390/antib4030240.*
Juma et al., Cells. May 8, 2021; 10(5):1140. doi: 10.3390/cells10051140.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Montelongo-Jauregui et al., PLoS Pathog. Aug. 12, 2020;16(8):e1008735. doi: 10.1371/journal.ppat.1008735. eCollection Aug. 2020.*

Janeway CA Jr, Travers P, Walport M, et al., Immunobiology: The Immune System in Health and Disease. 5th edition. New York: Garland Science; 2001., Appendix I. Immunologists' Toolbox, 43 pages downloaded Jan. 14, 2022 from https://www.ncbi.nlm.nih.gov/books/NBK10755/.*
Baum, Alina et al. "REGN-COV2 antibodies prevent and treat SARS-CoV-2 infection in rhesus macaques and hamsters." Science (New York, N.Y.) vol. 370,6520 (2020): 1110-1115. doi:10.1126/science.abe2402.
Cao, Yunlong et al. "Potent Neutralizing Antibodies against SARS-CoV-2 Identified by High-Throughput Single-Cell Sequencing of Convalescent Patients B Cells." Cell vol. 182,1 (2020): 73-84 e16. doi:10.1016/j.cell.2020.05.025.
Chi, X., Liu, X., Wang, C. et al. Humanized single domain antibodies neutralize SARS-CoV-2 by targeting the spike receptor binding domain. Nat Commun 11, 4528 (2020). https://doi.org/10.1038/s41467-020-18387-8.
Doud, M.B., Lee, J.M. Bloom, J.D. How single mutations affect viral escape from broad and narrow antibodies to H1 influenza hemagglutinin. Nat Commun 9, 1386 (2018). https://doi.org/10.1038/s41467-018-03665-3.
Doud, Michael B et al. "Complete mapping of viral escape from neutralizing antibodies." PLoS pathogens vol. 13,3 e1006271 Mar. 13, 2017, doi:10.1371/journal.ppat.1006271.
Hanke, L., Vidakovics Perez, L., Sheward, D.J. et al. An alpaca nanobody neutralizes SARS-CoV-2 by blocking receptor interaction. Nat Commun 11, 4420 (2020). https://doi.org/10.1038/s41467-020-18174-5.
Hansen et al., "Studies in humanized mice and convalescent humans yield a SARS-CoV-2 antibody cocktail" Science 369, 1010-1014 (2020).
Jeyanathan, Mangalakumari et al. "Immunological considerations for COVID-19 vaccine strategies." Nature reviews. Immunology vol. 20,10 (2020): 615-632. doi:10.1038/s41577-020-00434-6.
Konning, Doreen et al. "Camelid and shark single domain antibodies: structural features and therapeutic potential." Current opinion in structural biology vol. 45 (2017): 10-16 doi:10.1016/j.sbi.2016.10.019.
Korber et al., "Spike mutation pipeline reveals the emergence of a more transmissible form of SARS-CoV-2" 2020—Dell—doi: 10.1016/j.celL2020.06.043.

(Continued)

*Primary Examiner* — Michael Szperka
(74) *Attorney, Agent, or Firm* — KDB Firm PLLC

(57) ABSTRACT

The present disclosure provides coronavirus S1-fragment specific binding moieties comprising Type II VNAR domains, VNAR antibodies, methods of using those moieties and antibodies to treat COVID-19. In some embodiments, a VNAR antibody, originally selected from a phage display library as a VNAR clone using S1fragments from the SARS-CoV-2 Wuhan strain, are also effective at specifically binding to and/or neutralizing SARS-CoV-2 and certain SARS-CoV-2 mutants.

26 Claims, 8 Drawing Sheets
Specification includes a Sequence Listing.

(56) References Cited

OTHER PUBLICATIONS

Liu, Lihong et al. "Potent neutralizing antibodies against multiple epitopes on SARS-CoV-2 spike." Nature vol. 584,7821 (2020): 450-456. doi: 10.1038/s41586-020-2571-7.
Stanfield, Robyn L et al. "Crystal structure of a shark single-domain antibody V region in complex with lysozyme." Science (New York, N.Y.) vol. 305,5691 (2004): 1770-3. doi:10.1126/science.1101148.
Thyagarajan, Bargavi, and Jesse D Bloom. "The inherent mutational tolerance and antigenic evolvability of influenza hemagglutinin." eLife vol. 3 e03300. Jul. 8, 2014, doi:10.7554/eLife.03300.
Wang, C., Li, W., Drabek, D. et al. A human monoclonal antibody blocking SARS-CoV-2 infection. Nat Commun 11, 2251 (2020). https://doi.org/10.1038/s41467-020-16256-y.
Watanabe, Yasunori et al. "Exploitation of glycosylation in enveloped virus pathobiology." Biochimica et biophysica acta. General subjects vol. 1863,10 (2019): 1480-1497. doi:10 1016/j.bbagen 2019.05 012.
Watanabe, Yasunori et al. "Site-specific glycan analysis of the SARS-CoV-2 spike." Science (New York, N.Y.) vol. 369,6501 (2020): 330-333. doi:10.1126/science.abb9983.
Yang, Lifei et al. "COVID-19 antibody therapeutics tracker: a global online database of antibody therapeutics for the prevention and treatment of COVID-19" Antibody therapeutics vol. 3,3 (2020): 205-212. doi:10.1093/abt/tbaa020.

\* cited by examiner

US 11,345,742 B1

SHARK VNARS FOR TREATING COVID-19

CROSS REFERENCE TO RELATED APPLICATION

This application claims the benefit of provisional application U.S. Ser. No. 63/197,601, filed on Jun. 7, 2021, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 9, 2021, is named 9030_2101-US2_SL.txt and is 170,721 bytes in size.

FIELD OF THE DISCLOSURE

The present disclosure relates to the identification of single domain VNARs derived by bio-panning against the spike protein from the SARS-CoV-2 Wuhan variant. The screen identified ten VNAR Fc fusion proteins (VNAR antibodies) that were shown in biochemical and cells-based assays to be highly effective in blocking the interaction of recombinant spike protein with ACE2 receptor and eight were confirmed to neutralize live Wuhan variant virus using in vitro assays. These ten VNAR antibodies retained high affinity binding and blocking activity against the S1-RBD N501Y mutant, and three had activity against the S1-RBD E484K mutant. The VNAR antibody panel directed against the SARS CoV-2 spike protein expands the molecular toolbox of novel antibody therapeutic approaches directed against COVID-19.

BACKGROUND

The current COVID-19 pandemic, caused by the transmission of severe acute respiratory syndrome coronavirus 2 (SARS-CoV-2), is associated with high infection rates and in some high-risk populations with high mortality rate. Immunological approaches, including vaccines and therapeutic antibodies, have been successfully pursued and are proving immensely helpful in preventing further spread of the virus as well as treating the severely ill. While a high level of protection in immunized populations is observed, establishing long-term safety and efficacy of vaccines will require continuous monitoring of protection especially against newly emerging variants, including B.1.1.7/501Y.V1 (Kent), lineage B.1.351/501Y.V2 (South African), and lineage P.1 (Brazilian). As vaccine-induced immunity can be less effective in older populations and immunocompromised individuals, and can potentially trigger a harmful response in some cases (Jeyanathan, Afkhami et al. 2020), passive immunization via direct administration of purified antibodies may provide a solution to both prevent and treat infections (Yang, Liu et al. 2020).

The receptor binding domain (S1-RBD) of the spike protein is the main target for various vaccine and antibody neutralization approaches. However, it is highly protected by being tightly folded within the structure and covered by a glycan shield (Watanabe, Allen et al. 2020). Furthermore, neutralizing antibodies to only a single dominant epitope can result in selective pressure for viral mutants that escape inhibition. Neutralizing antibodies to the S1-RBD domain have been isolated by cloning human B cells from infected patients and by immunizing humanized mice (Baum, Ajithdoss et al. 2020; Cao, Su et al. 2020; Liu, Wang et al. 2020) but these approaches are not without issues. A major problem with B cell cloning is that many antibodies, and in particular IgMs, will be generated to glycans on the spike protein which impede recognition of neutralizing epitopes. Both approaches suffer from immunodominance which limits epitope coverage and directs the response to viral epitopes more tolerant of mutations. RNA viruses spontaneously evolve as they spread across populations and mutations are already accumulating in the SARS-CoV-2 spike protein both within and outside the S1-RBD domain (Korber, Fischer et al. 2020), which makes targeting a single immunodominant epitope highly prone to escape upon mutation.

A potent antibody-evasion strategy employed by viruses is the so-called "glycan shield" present on many viral glycoproteins, which masks neutralizing antibody to antigenically conserved sites (Watanabe, Bowden et al. 2019). Shark VNAR single domain antibodies (also known as IgNARs), which have evolved to compliment conventional antibodies, offer an important alternative with significant advantages for combating viral defenses. Surface-exposed epitopes available to conventional IgGs are generally more tolerant of mutations which allow viral escape (Thyagarajan and Bloom 2014; Doud, Hensley et al. 2017; Doud, Lee et al. 2018). With their small size and long CDR3 loop, VNAR single domain antibodies are ideally designed to access buried epitopes beneath the glycan shield (Stanfield, Dooley et al. 2004; Konning, Zielonka et al. 2017).

To overcome these shortcomings of conventional antibodies, VNARs have been developed which target the spike protein within S1-RBD and N-terminal domain (S1-NTD). The VNAR domains directed against the SARS-CoV-2 spike protein expands the molecular toolbox of antibody therapeutic approaches directed against COVID-19 disease.

SUMMARY

The present disclosure provides coronavirus S1-fragment specific binding moieties comprising Type II VNAR domains, VNAR antibodies, methods of using those moieties and antibodies to treat COVID-19, and improved Type II VNAR libraries for screening, selecting and/or identifying VNARs that bind specifically to a target molecule of interest. In some embodiments, a VNAR antibody, originally selected from a phage display library as a VNAR clone using S1 fragments from the SARS-CoV-2 Wuhan strain, are also effective at specifically binding to and/or neutralizing SARS-CoV-2 and certain SARS-CoV-2 mutants.

In one aspect, the S1 fragment-binding moieties comprise a Type II VNAR domain represented by the formula, from N to C terminus,

FW1-CDR1-FW2-HV2-FW2'-HV4-FW3-CDR3-FW4, wherein CDR1 comprises or consists essentially of a peptide having an amino acid sequence of one of DSICALSS, DSNCALPS, DSVCALSS, or DSNCALSS (SEQ ID NOS. 150-153, respectively), wherein CDR3 comprises or consists essentially of a peptide having an amino acid sequence of one of VHMEDMNVRDYGGFWGEDV, VNLRSVLPCGWPDV, VENLPGSGSCLRYYLSDV, VREWACEDDGRVWGWEDV, VARTSGCEVYTYTGDV, VKNPSGCGVWYSQEDL, SEFKSGCGVFYELTDV, MVFKSVCEDNPYQYGL, or IWAHSGCEVITHAMDL (SEQ ID NOS. 154-162, respectively), and wherein said moiety is capable of specifically binding to an S1 fragment comprising amino acids 16-685 of a SARS-CoV-2 spike protein. In some embodiments, HV2 is TNEENISKG, TNEESISKG, RKEESISKG, or TNEENILTG (SEQ ID NOS. 163-166, respectively). In some embodiments, HV4 is SGSKS or RGSKS (SEQ ID NOS. 167-168, respectively). In embodiments, the VNAR domain comprises one of the CDR1s and CDR3s together with any one of the HV2s, with any one of the HV4s, or with both of any one of the HV2s and an HV4s.

In some embodiments of the moiety, the CDR1 peptide has an amino acid sequence of DSICALSS (SEQ ID NO: 150) and the CDR3 peptide has an amino acid sequence of VHMEDMNVRDYGGFWGEDV (SEQ ID NO: 154) (from VNAR 25);

the CDR1 peptide has the amino acid sequence of DSICALSS (SEQ ID NO: 150) and the CDR3 peptide has an amino acid sequence of VNLRSVLPCGWPDV (SEQ ID NO: 155) (from VNAR 46);

the CDR1 peptide has an amino acid sequence of DSICALSS (SEQ ID NO: 150) and the CDR3 peptide has an amino acid sequence of VENLPGSGSCLRYYLSDV (SEQ ID NO: 156) (from VNAR 61;

the CDR1 peptide has an amino acid sequence DSNCALPS (SEQ ID NO: 151) and the CDR3 peptide has an amino acid sequence of VREWACEDDGRVWGWEDV (SEQ ID NO: 157) (from VNAR 68);

the CDR1 peptide has an amino acid sequence of DSICALSS (SEQ ID NO: 150) and the CDR3 peptide has an amino acid sequence of VARTSGCEVYTYTGDV (SEQ ID NO: 158) (from VNAR 105 or 106);

the CDR1 peptide has an amino acid sequence of DSVCALSS (SEQ ID NO: 152) and the CDR3 peptide has an amino acid sequence of VKNPSGCGVWYSQEDL (SEQ ID NO: 159) (from VNAR 115);

the CDR1 peptide has an amino acid sequence of DSICALSS (SEQ ID NO: 150) and the CDR3 peptide has an amino acid sequence of SEFKSGCGVFYELTDV (SEQ ID NO: 160) (from VNAR 119);

the CDR1 peptide has an amino acid sequence of DSNCALSS (SEQ ID NO: 153) and the CDR3 peptide has an amino acid sequence of MVFKSVCEDNPYQYGL (SEQ ID NO: 161) (from VNAR 132); or the CDR1 peptide has an amino acid sequence of DSICALSS (SEQ ID NO: 150) and the CDR3 peptide has an amino acid sequence of IWAHSGCEVITHAMDL (SEQ ID NO: 162) (from VNAR 135).

In some embodiments, the moiety comprises any one of VNAR domains 25, 46, 61, 68, 105, 106, 115, 119, 132, or 135 (SEQ ID NOS. 25, 46, 61, 68, 105, 106, 115, 119, 132, or 135).

In an aspect, any of the moieties of the disclosure further comprise at least one heterologous agent operably linked thereto to thereby form a conjugate. Such heterologous agents, include but are not limited to, one or more of a small molecule diagnostic or therapeutic; a DNA, RNA, or hybrid DNA-RNA; a traceable marker; a radioactive agent; an antibody; a single chain variable domain; or an immunoglobulin fragment.

In some embodiments the heterologous agent is an immunoglobulin fragment and is operably linked to the VNAR domain to form a fusion protein. In an embodiment, the immunoglobulin fragment is a Fc domain, and preferably a human Fc domain. The human Fc domain can be from any immunoglobulin isotype. In preferred embodiment, the isotype is an IgG.

A further aspect relates to pharmaceutical compositions comprising at least one moiety, conjugate or fusion protein of the disclosure. In embodiments, such compositions can also have, independently, two, three, four, five or more of such moieties, conjugates or fusion proteins.

In an aspect, the disclosure provides a method of passive immunization against SARS-CoV-2, and variants thereof, which comprises administering a pharmaceutical composition of the disclosure to a subject in need thereof.

In another aspect, the disclosure provides a method of preventing or treating COVID-19 which comprises administering a pharmaceutical composition of the disclosure to a mammal or a subject for a time and in an amount effect to treat or prevent COVID-19.

In some embodiment of these methods, the subject or mammal has tested positive for SARS-CoV-2. In some embodiments of these methods, the subject or mammal has suspected exposure to SARS-CoV-2 and/or tested negative for SARS-CoV-2. In some embodiments of these methods, the composition is administered intravenously, subcutaneously, intramuscularly, intranasally or by inhalation.

In a further aspect, this disclosure provides VNAR antibodies which comprise a moiety of the disclosure fused to a human Fc domain, which upon expression form a bispecific VNAR antibody. In embodiments of the VNAR antibody, the moiety has a VNAR domain wherein the CDR1 peptide has an amino acid sequence of DSICALSS (SEQ ID NO: 150) and the CDR3 peptide has an amino acid sequence of VHMEDMNVRDYGGFWGEDV (SEQ ID NO: 154) (from VNAR 25);

the CDR1 peptide has the amino acid sequence of DSICALSS (SEQ ID NO: 150) and the CDR3 peptide has an amino acid sequence of VNLRSVLPCGWPDV (SEQ ID NO: 155) (from VNAR 46);

the CDR1 peptide has an amino acid sequence of DSICALSS (SEQ ID NO: 150) and the CDR3 peptide has an amino acid sequence of VENLPGSGSCLRYYLSDV (SEQ ID NO: 156) (from VNAR 61;

the CDR1 peptide has an amino acid sequence DSNCALPS (SEQ ID NO: 151) and the CDR3 peptide has an amino acid sequence of VREWACEDDGRVWGWEDV (SEQ ID NO: 157) (from VNAR 68);

the CDR1 peptide has an amino acid sequence of DSICALSS (SEQ ID NO: 150) and the CDR3 peptide has an amino acid sequence of VARTSGCEVYTYTGDV (SEQ ID NO: 158) (from VNAR 105 or 106);

the CDR1 peptide has an amino acid sequence of DSVCALSS (SEQ ID NO: 152) and the CDR3 peptide has an amino acid sequence of VKNPSGCGVWYSQEDL (SEQ ID NO: 159) (from VNAR 115);

the CDR1 peptide has an amino acid sequence of DSICALSS (SEQ ID NO: 150) and the CDR3 peptide has an amino acid sequence of SEFKSGCGVFYELTDV (SEQ ID NO: 160) (from VNAR 119);

the CDR1 peptide has an amino acid sequence of DSNCALSS (SEQ ID NO: 153) and the CDR3 peptide has an amino acid sequence of MVFKSVCEDNPYQYGL (SEQ ID NO: 161) (from VNAR 132); or the CDR1 peptide has an amino acid sequence of DSICALSS (SEQ ID NO: 150) and the CDR3 peptide has an amino acid sequence of IWAHSGCEVITHAMDL (SEQ ID NO: 162) (from VNAR 135). As indicated, the CDR1 and CDR3 peptides are the cognate pair found in the recited VNAR domain.

In some embodiments of the VNAR antibody, its VNAR domain is any one of VNAR domains 25, 46, 61, 68, 105, 106, 115, 119, 132, or 135 (SEQ ID NOS. 25, 46, 61, 68, 105, 106, 115, 119, 132, or 135). In an embodiment, a VNAR antibody is capable of neutralizing infection of SARS-CoV-2

A further aspect relates to pharmaceutical compositions comprising at least one VNAR antibody of the disclosure. In embodiments, such compositions can also have, independently, two, three, four, five or more VNAR antibodies.

In an aspect, the disclosure provides a method of passive immunization against SARS-CoV-2, and variants thereof, which comprises administering a pharmaceutical composition comprising one or more VNAR antibodies of the disclosure to a subject in need thereof.

In another aspect, the disclosure provides a method of preventing or treating COVID-19 which comprises administering a pharmaceutical composition comprising one or more VNAR antibodies of the disclosure to a mammal or a subject for a time and in an amount effect to treat or prevent COVID-19.

In some embodiment of these methods, the subject or mammal has tested positive for SARS-CoV-2. In some embodiments of these methods, the subject or mammal has suspected exposure to SARS-CoV-2 and/or tested negative for SARS-CoV-2. In some embodiments of these methods, the composition is administered intravenously, subcutaneously, intramuscularly, intranasally or by inhalation.

In yet another aspect, the disclosure provides a coronavirus S1 fragment binding moiety comprising a Type II VNAR domain capable of specifically binding to an S1 fragment comprising amino acids 16-685 of SARS-CoV-2 spike protein, wherein the said VNAR domain comprises an amino acid sequence of any one of VNAR clones 1-149 in Table 3 or Table 4 (SEQ ID NOS.1-149). In embodiments, these moieties further comprise at least one heterologous agent operably linked to the moiety to thereby form a conjugate.

Calculated $EC_{50}$ values are presented in Table 13.

Figure 13:
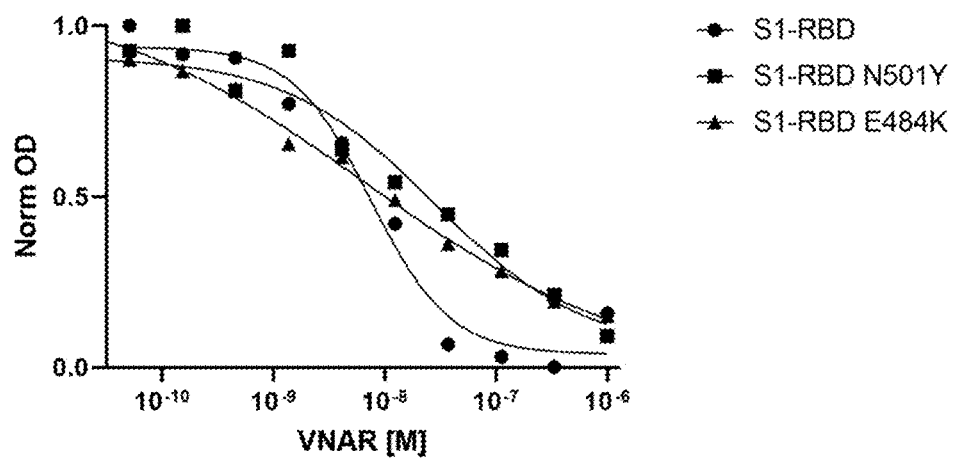

FIG. 13. $IC_{50}$ curves of VNAR antibody 25 that blocks Spike protein interactions with ACE2. ACE2 at a fixed concentration was premixed with serially-diluted VNAR antibodies before incubation with recombinant S1-RBD, S1-RBD N501Y or S1-RBD E484K immobilized on ELISA plates. ACE2 binding was detected by anti-FLAG HRP conjugated antibody. Data presented as normalized OD at 450 nm. All calculated $IC_{50}$ values are presented in Table 14.

Figure 14:
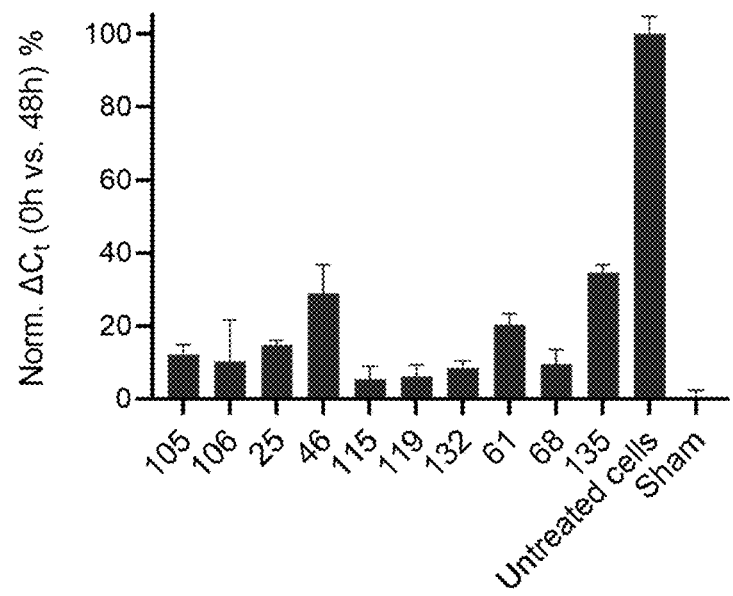

FIG. 14. Neutralization of SARS-CoV-2 virus by VNAR antibodies. Vero CCL81 cells were exposed to SARS-CoV-2 Wuhan strain preincubated with or without VNAR antibodies at 5 µg/mL (65 nM) for 48 hr using VNAR antibodies 25, 46, 61, 68, 105, 106, 115, 119, 132 and 135. Viral load was determined at the start of the experiment and after 48 hr using RT-qPCR. Infection was assessed relative to cells treated with the virus in the absence of VNAR antibodies.

Figure 15:
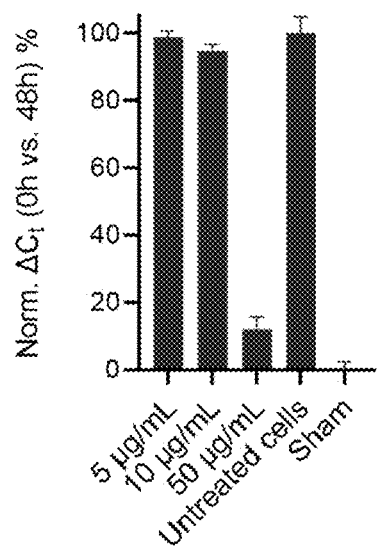

FIG. 15. Neutralization of SARS-CoV-2 virus by VNAR antibody 137. Vero CCL81 cells were exposed to SARS-CoV-2 Wuhan strain preincubated with or without VNAR antibody 137 at 5, 10, 50 µg/mL (65, 130, 650 nM) for 48 hr. Viral load was determined at start of the experiment and after 48 hr using RT-qPCR. Infection was assessed relative to cells treated with the virus in the absence of VNAR antibodies.

Figure 16:
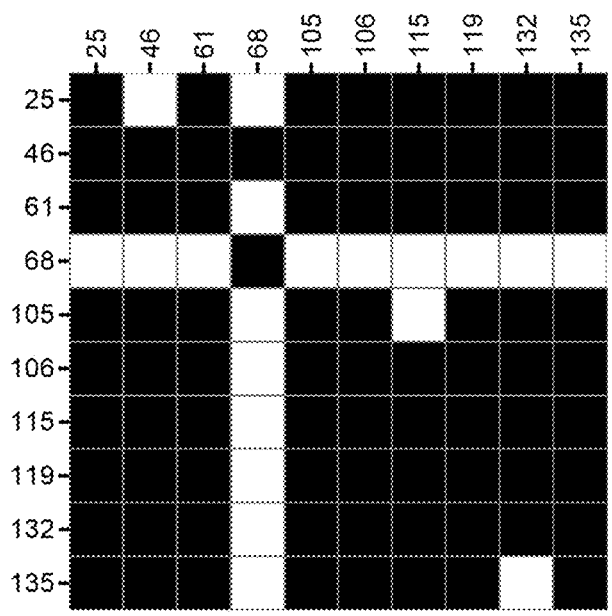

FIG. 16. Epitope binning of VNAR antibodies by cross competition ELISA. VNAR antibodies (25, 46, 61, 68, 105, 106, 115, 119, 132 and 135) were used to coat ELISA microplate wells, followed by addition of S1-RBD or premixed biotinylated S1-RBD and a competitor VNAR antibody. Binding of biotinylated S1-RBD to immobilized VNAR antibodies was detected by streptavidin-HRP. Black color indicate competition between two antibodies for the overlapping epitope bin. White color indicates no competition, thus a unique epitope bin.

DETAILED DESCRIPTION

Definitions

In order that the present disclosure may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "plurality" as used herein refers to the number of members of a collection, which minimum is at least 10, 20, 30, 50, 75, 100, 1000 or more, and which minimum or maximum number may not be readily ascertainable but which may be indicated by type of collection or the context of its use. For example, a phage display library contains a plurality of phage equal to its titer (which may be the same or different), and by extension encodes a corresponding plurality of polypeptides.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., cows, pigs), companion animals (e.g., dogs, cats) and rodents (e.g., mice and rats).

The term "non-human mammal" means a mammal which is not a human and includes, but is not limited to, a mouse, rat, rabbit, pig, cow, sheep, goat, dog, non-human primate, or other non-human mammals, typically as used in research. As used herein, "mammals" includes the foregoing non-human mammals and humans.

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment and is not necessarily meant to imply permanent prevention of the relevant disease, disorder or condition. Thus "preventing" or "prevention" of a condition may in certain contexts refer to reducing the risk of developing the condition or preventing or delaying the development of symptoms associated with the condition.

As used herein, an "effective amount," "therapeutically-effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

A physiologically-acceptable solution for use in an amount and for a time sufficient to effectively reduce a circulating concentration of the plurality of polypeptides is referred to herein as a perfusate. The amount of perfusate and time of perfusion depends on the non-human mammal and can be readily determined by those of skill in the art. For example, with a mouse, using a volume of perfusate approximately 10× the blood volume of the mouse is effective at reducing the circulating concentration of polypeptides. Likewise, any volume of perfusate that reduces the circulating concentration of the plurality of polypeptides by about 10%, 25%, 50% or more (relative to the theoretical concentration of the plurality of polypeptides) being delivered is considered effective at reducing the circulating concentration of that plurality.

As used herein, a "VNAR domain" or "VNAR" has the general structure, from N to C terminus, given by the formula FW1-CDR1-FW2-HV2-FW2'-HV4-FW3-CDR3-FW4, wherein the FWs are framework regions, CDRs are complementarity determining regions and HVs are hypervariable regions that form the variable domain of a shark IgNAR. The CDR3 region in naturally-occurring VNARs is of heterogeneous size, ranging from about 7 to about 32 amino acid residues in length. The VNAR domains of the invention can optionally have a His-Tag (or other convenient tag for purification purposes). In some cases, such tags are removable. Typical VNAR domains have amino acid residues (aa) 1-25 of the framework 1 (FW1) region; aa 26-33 of the complimentary determining region 1 (CDR1); aa 34-43 of FW2; aa 44-52 of the hypervariable 2 region (HV2); aa 53-84 of FW3; aa 61-65 of HV4; the CDR3 region (of variable length begins with aa 85) and FW4 (11 residues starting immediately after CDR3 at XGXG).

As used herein, binding to the target of interest is called specific binding, while binding to other sites is called nonspecific binding. As used herein, a binding moiety, specific binding moiety, antibody or VNAR domain that "specifically binds" to its target does so selectively or preferentially. Such moieties, antibodies and VNARS can exhibit specific binding to multiple targets such as occurs when one of these entities exhibits species cross reactivity.

Abbreviations used herein for conventional antibodies include: VL, variable region, light chain; VH, variable region, heavy chain; CL, constant region of light chain; HC, constant region of heavy chain.

SARS-CoV-2 S1 Fragment Binding Moieties and Conjugates Thereof

The present invention relates to coronavirus SARS-CoV-2 S1-fragment-specific binding moieties comprising Type II VNAR domains obtained by in vitro selection against recombinant spike protein fragments, including the recombinant S1 domain encoded by amino acids 16-685 of the spike protein and the S1-RBD domain encoded by amino acids 319-541 of the spike protein, using VNAR OSX3 and OSX6 phage display libraries.

In one aspect, the disclosure provides a coronavirus S1-fragment binding moiety comprising a Type II VNAR domain capable of specifically binding to an S1 fragment comprising amino acids 16-685 of SARS-CoV-2 spike protein, wherein the VNAR domain comprises an amino acid sequence of any one of VNAR clones 1-149 in Table 3 and Table 4 (SEQ ID NOS.1-149; see Example 2).

The CDR1, HV2, HV4 and CDR3 sequences for each of the foregoing VNAR domains identified from the OSX3 and OSX6 libraries are also listed in Tables 5 and 6 for convenience. Each CDR1, HV2, HV4 and CDR3 sequence is a subsequence of its respective VNAR domain set forth in SEQ ID NOS. 1-149. Hence, for each VNAR domain, the CDR1 sequence is found at amino acids 26-33 of the corresponding SEQ ID NO. for that domain; the HV2 sequence at amino acids 44-52; the HV4 sequence at amino acids 61-65; and the CDR3 sequence beginning at amino acid 85 and continuing the length of the particular CDR3.

In some embodiments, the foregoing moieties further comprise at least one heterologous agent operably linked to the moiety to thereby form a conjugate.

In a further aspect, the disclosure provides further S1 fragment-binding moieties which comprise a Type II VNAR domain represented by the formula, from N to C terminus,

FW1-CDR1-FW2-HV2-FW2'-HV4-FW3-CDR3-FW4, wherein CDR1 comprises or consists essentially of a peptide having an amino acid sequence of one of DSICALSS, DSNCALPS, DSVCALSS, or DSNCALSS (SEQ ID NOS. 150-153, respectively), wherein CDR3 comprises or consists essentially of a peptide having an amino acid sequence of one of VHMEDMNVRDYGGFWGEDV, VNLRSVLPCGWPDV, VENLPGSGSCLRYYLSDV, VREWACEDDGRVWGWEDV, VARTSGCEVYTYTGDV, VKNPSGCGVWYSQEDL, SEFKSGCGVFYELTDV, MVFKSVCEDNPYQYGL, or IWAHSGCEVITHAMDL (SEQ ID NOS. 154-162, respectively), and wherein said moiety is capable of specifically binding to an S1 fragment comprising amino acids 16-685 of a SARS-CoV-2 spike protein. In some embodiments, HV2 is TNEENISKG, TNEESISKG, RKEESISKG, or TNEENILTG (SEQ ID NOS. 163-166, respectively). In some embodiments, HV4 is SGSKS or RGSKS (SEQ ID NOS. 167-168, respectively). In embodiments, the VNAR domain comprises one of the CDRIs and CDR3s together with any one of the HV2s, with any one of the HV4s, or with both of any one of the HV2s and an HV4s.

In some embodiments of these further moieties, the CDR1 peptide has an amino acid sequence of DSICALSS (SEQ ID NO: 150) and the CDR3 peptide has an amino acid sequence of VHMEDMNVRDYGGFWGEDV (SEQ ID NO: 154) (from VNAR 25);

the CDR1 peptide has the amino acid sequence of DSICALSS (SEQ ID NO: 150) and the CDR3 peptide has an amino acid sequence of VNLRSVLPCGWPDV (SEQ ID NO: 155) (from VNAR 46);

the CDR1 peptide has an amino acid sequence of DSICALSS (SEQ ID NO: 150) and the CDR3 peptide has an amino acid sequence of VENLPGSGSCLRYYLSDV (SEQ ID NO: 156) (from VNAR 61;

the CDR1 peptide has an amino acid sequence DSNCALPS (SEQ ID NO: 151) and the CDR3 peptide has an amino acid sequence of VREWACEDDGRVWGWEDV (SEQ ID NO: 157) (from VNAR 68);

the CDR1 peptide has an amino acid sequence of DSICALSS (SEQ ID NO: 150) and the CDR3 peptide has an amino acid sequence of VARTSGCEVYTYTGDV (SEQ ID NO: 158) (from VNAR 105 or 106);

the CDR1 peptide has an amino acid sequence of DSVCALSS (SEQ ID NO: 152) and the CDR3 peptide has an amino acid sequence of VKNPSGCGVWYSQEDL (SEQ ID NO: 159) (from VNAR 115);

the CDR1 peptide has an amino acid sequence of DSICALSS (SEQ ID NO: 150) and the CDR3 peptide has an amino acid sequence of SEFKSGCGVFYELTDV (SEQ ID NO: 160) (from VNAR 119);

the CDR1 peptide has an amino acid sequence of DSNCALSS (SEQ ID NO: 153) and the CDR3 peptide has an amino acid sequence of MVFKSVCEDNPYQYGL (SEQ ID NO: 161) (from VNAR 132); or the CDR1 peptide has an amino acid sequence of DSI-CALSS (SEQ ID NO: 150) and the CDR3 peptide has an amino acid sequence of IWAHSGCEVITHAMDL (SEQ ID NO: 162) (from VNAR 135).

In some embodiments, the FW1, FW2, FW2', FW3 and FW4 regions of the Type II VNAR domains have naturally occurring VNAR sequences or altered VNAR sequences with amino acid substitutions, insertions or deletions (typically, but not limited to, no more than 1-10 amino acids changes, insertions or deletions) provided that such alterations maintain the overall primary and tertiary structure of the Type II VNAR, and provided that such VNAR domains have combinations of CDR1, HV2, HV4, and CDR3 regions recited in the preceding two paragraphs. In some embodiments, the FW1, FW2, FW2', FW3 and FW4 regions of the Type II VNAR domains have a sequence for those regions as set forth in Tables 3 and 4 (in any independent combination), and, again, provided that such VNAR domains have combinations of CDR1, HV2, HV4, and CDR3 regions recited in the preceding two paragraphs.

In some embodiments, these further moieties comprise any one of VNAR domains 25, 46, 61, 68, 105, 106, 115, 119, 132, or 135 (SEQ ID NOS. 25, 46, 61, 68, 105, 106, 115, 119, 132, or 135).

In some embodiments, the VNAR domains of any of the moieties of the disclosure can optionally have a His-Tag (or other convenient tag for purification purposes). In some cases, such tags are removable.

In an aspect, any of the moieties of the disclosure further comprise at least one heterologous agent operably linked thereto to thereby form a conjugate. Such heterologous agents, include but are not limited to, one or more of a small molecule diagnostic or therapeutic; a DNA, RNA, or hybrid DNA-RNA; a traceable marker; a radioactive agent; an antibody; a single chain variable domain; or an immunoglobulin fragment.

In some embodiments the heterologous agent is an immunoglobulin fragment and is operably linked to the VNAR domain to form a fusion protein. In an embodiment, the immunoglobulin fragment is a human Fc domain. The human Fc domain can be from any immunoglobulin isotype. In preferred embodiment, the isotype is an IgG, and more preferably IgG1. Fusion proteins are generally monospecific but can be bispecific.

In yet another aspect of the invention, any of the VNAR domains described herein can form all or part of the variable domain of a single variable domain antibody, a bi- or tri-functional VNAR, a conventional antibody, or any fragment or fusion protein of said antibody as well as variable domains with antibody-like backbones. Such constructs can be made by methods known to those of skill in the art.

Examples of single variable domain antibodies include, but are not limited to, a shark or other cartilaginous fish antibodies, camelid antibodies and nanobodies. Examples of conventional antibodies (and their fragments) include, but are not limited to, immunoglobins having both heavy and light chains, such as IgM's, IgA's, IgG's, IgE's, single chain Fv's, Fab fragments, or any fragment or fusion protein of such antibodies or fragments.

In embodiments, any of the VNAR domains disclosed herein can be fused to an Fc domain of a conventional antibody to form a VNAR-Fc conjugate. Such fusions can be made at the N terminus or the C terminus of the Fc domain. In some embodiments, the Fc domain is a mammalian Fc domain, including primate Fc domains. More particularly, the Fc domain is a human Fc domain (hFc), a cynomolgus macaque Fc domain (cFc) or a murine Fc domain.

Most preferably the Fc domain is an hFc domain. In some embodiments, the Fc domain is from an IgG, and preferably from IgG1. Such fusions are also referred to herein as VNAR antibodies. Methods of making fusion proteins are well known in the art.

Further, non-limiting examples of antibody-like backbones that may be used according to the disclosure include monospecific and bispecific backbones, such as multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H$1 domains, bivalent F(ab')2 fragments, Fd fragments consisting of the heavy chain and $C_H$1 domains, dimeric $C_H$2 domain fragments ($C_H$2D), Fc antigen binding domains (Fcabs), single chain Fv-$C_H$3 minibodies, bispecific minibodies, isolated complementary determining region 3 (CDR3) fragments, constrained FR3-CDR3-FR4 polypeptides, SMIP domains, and any genetically manipulated counterparts of the foregoing that S1 binding function (see e.g., Weiner L, Cell 148: 1081-4 (2012); Ahmad Z et al., Clin Dev Immunol 2012: 980250 (2012) for reviews).

VNAR Antibodies

In a further aspect, this disclosure provides VNAR antibodies which comprise an S1-specific binding moiety of the disclosure in which its VNAR domain is fused to a human Fc domain (hFc). When such fusion proteins are expressed, due to the nature of the Fc domain, two chains can associate to form a dimer and thus produce a bispecific molecule, herein referred to as a bispecific VNAR antibody.

The VNAR antibodies of the disclosure are suitable for use in humans, particularly for providing passive immunity against SARS-CoV-2, and variants thereof, and for treating and ameliorating COVID-19 disease and associated symptoms.

In some embodiments, the VNAR antibodies are capable of blocking the interaction and/or binding of the SARS-CoV-2 spike protein with the ACE2 receptor. In some embodiments, the VNAR antibodies are capable of blocking the interaction and/or binding of mutant SARS-CoV-2 spike protein with the ACE2 receptor. In some embodiments the mutant spike protein has a single mutation, including the E484K or N501Y mutation. In some embodiments, the mutant spike protein is a quadruple mutant of S1 containing K417N, E484K, N501Y and D614G mutations. These spike mutations are referenced relative to the amino acid sequence of the spike protein from the Wuhan strain, for example, the E484K mutant has the amino acid glutamic acid (E) found at position 484 of the spike protein replaced with the amino acid lysine (K). Similarly, for the N501Y mutation, the amino acid aspartic acid (N) found at position 501 is replaced with tyrosine (Y), and so on for the quadruple mutant and other mutants.

In some embodiments, the VNAR antibodies are capable of neutralizing viral infection, including but not limited to the Wuhan strain and mutants thereof, including the mutants single E484K or N501Y mutation as well as a quadruple mutant of S1 protein containing K417N, E484K, N501Y and D614G mutations.

Methods of making Fc fusion proteins are well known in the art. In some embodiments, the VNAR domain is operably linked via a linker peptide to the C-terminus and/or N-terminus of the Fc domain, and preferably at the N-terminus. In some embodiments, the Fc domain is from an IgG, and preferably from IgG1 but other human Fc domain isotype are contemplated.

Accordingly, preferred embodiments of the VNAR antibody, include but are not limited to S1-specific binding moieties having a Type II VNAR domain represented by the formula, from N to C terminus, FW1-CDR1-FW2-HV2-FW2'-HV4-FW3-CDR3-FW4, wherein the CDR1 peptide has an amino acid sequence of DSICALSS (SEQ ID NO: 150) and the CDR3 peptide has an amino acid sequence of VHMEDMNVRDYGGFWGEDV (SEQ ID NO: 154) (from VNAR 25);

the CDR1 peptide has the amino acid sequence of DSICALSS (SEQ ID NO: 150) and the CDR3 peptide has an amino acid sequence of VNLRSVLPCGWPDV (SEQ ID NO: 155) (from VNAR 46);

the CDR1 peptide has an amino acid sequence of DSICALSS (SEQ ID NO: 150) and the CDR3 peptide has an amino acid sequence of VENLPGSGSCLRYYLSDV (SEQ ID NO: 156) (from VNAR 61;

the CDR1 peptide has an amino acid sequence DSNCALPS (SEQ ID NO: 151) and the CDR3 peptide has an amino acid sequence of VREWACEDDGRVWGWEDV (SEQ ID NO: 157) (from VNAR 68);

the CDR1 peptide has an amino acid sequence of DSICALSS (SEQ ID NO: 150) and the CDR3 peptide has an amino acid sequence of VARTSGCEVYTYTGDV (SEQ ID NO: 158) (from VNAR 105 or 106);

the CDR1 peptide has an amino acid sequence of DSVCALSS (SEQ ID NO: 152) and the CDR3 peptide has an amino acid sequence of VKNPSGCGVWYSQEDL (SEQ ID NO: 159) (from VNAR 115);

the CDR1 peptide has an amino acid sequence of DSICALSS (SEQ ID NO: 150) and the CDR3 peptide has an amino acid sequence of SEFKSGCGVFYELTDV (SEQ ID NO: 160) (from VNAR 119);

the CDR1 peptide has an amino acid sequence of DSNCALSS (SEQ ID NO: 153) and the CDR3 peptide has an amino acid sequence of MVFKSVCEDNPYQYGL (SEQ ID NO: 161) (from VNAR 132); or the CDR1 peptide has an amino acid sequence of DSICALSS (SEQ ID NO: 150) and the CDR3 peptide has an amino acid sequence of IWAHSGCEVITHAMDL (SEQ ID NO: 162) (from VNAR 135).

For some embodiments of the VNAR antibodies, HV2 is TNEENISKG, TNEESISKG, RKEESISKG, or TNEENILTG (SEQ ID NOS. 163-166, respectively). For some embodiments of the VNAR antibodies, HV4 is SGSKS or RGSKS (SEQ ID NOS. 167-168, respectively). Additionally, in some embodiments, the VNAR domain comprises the CDR1 and CDR3 pair together with any one of the HV2s, with any one of the HV4s, or with both of any one of the HV2s and an HV4s.

For the foregoing VNAR domains, the FW1, FW2, FW2', FW3 and FW4 regions can have naturally occurring VNAR sequences or altered VNAR sequences with amino acid substitutions, insertions or deletions (typically, but not limited to, no more than 1-10 amino acids changes, insertions or deletions) provided that such alterations maintain the overall primary and tertiary structure of a Type II VNAR domain, and provided that such VNAR domains have combinations of CDR1, HV2, HV4, and CDR3 regions recited in the preceding two paragraphs. In some embodiments, the FW1, FW2, FW2', FW3 and FW4 regions of the Type II VNAR domains have a sequence for those regions as set forth in Tables 3 and 4 (in any independent combination), and, again, provided that such VNAR domains have combinations of CDR1, HV2, HV4, and CDR3 regions recited in the preceding two paragraphs.

In some embodiments of the VNAR antibody, the VNAR domain is any one of VNAR domains 25, 46, 61, 68, 105, 106, 115, 119, 132, or 135 (SEQ ID NOS. 25, 46, 61, 68, 105, 106, 115, 119, 132, or 135). In an embodiment, a VNAR antibody is capable of neutralizing infection of SARS-CoV-2

Additional Conjugates

The moieties, VNAR domains (VNAR polypeptides) and VNAR antibodies disclosed herein may optionally be conjugated (e.g., using linkers such as chemical linkers and/or linker peptides which are not usually associated with the domains being associated) to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like. In certain embodiments, the pharmaceutically active moieties comprise at least one scFv molecule that is operably linked via a linker peptide to the C-terminus and/or N-terminus of an Fc region.

In certain embodiments, The moieties, VNAR domains (VNAR polypeptides) and VNAR antibodies disclosed herein are multispecific, i.e., have at least one binding site that binds to a first molecule or epitope of a molecule (i.e., the S1 fragment) and one or more other binding sites that bind to at least one heterologous molecule or to an epitope of either S1, another SARS-CoV-2 protein or another molecule. Multispecific binding molecules of the disclosure may comprise at least two binding sites, three binding sites, four binding sites or more.

Nucleic Acid Sequences That Encode an S1-Fragment-Specific Binding Moiety

In one aspect, the invention provides an isolated nucleic acid which encodes an S1-fragment-specific binding moiety, conjugate, or VNAR antibody disclosed herein, or a fragment or derivative thereof. The invention also provides an isolated nucleic acid molecule comprising a sequence that hybridizes under stringent conditions to a nucleic acid sequence which encodes a moiety, conjugate, or VNAR antibody of the disclosure, or a fragment or derivative thereof, or the antisense or complement of any such sequence.

In another aspect, the invention provides an isolated nucleic acid molecule encoding a fusion protein comprising at least two segments, wherein one of the segments comprises a moiety or VNAR domain disclosed herein. In certain embodiments, a second segment comprises a heterologous signal polypeptide, a heterologous binding moiety, an immunoglobulin fragment such as a Fc domain, or a detectable marker.

A further aspect includes isolated nucleic acid molecules that encode moieties, conjugates, or VNAR antibodies of the disclosure or biologically active portions thereof. Also included are nucleic acid fragments sufficient for use as hybridization probes to identify S1-fragment binding moieties encoding nucleic acids and fragments for use as polymerase chain reaction (PCR) primers for the amplification or mutation of nucleic acid molecules encoding VNAR domains disclosed herein.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the disclosure may be single-, double-, or triple-stranded. A nucleic acid molecule of the present disclosure may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the disclosure may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a moiety, conjugate, or VNAR antibody of the disclosure may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the disclosure include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. A percent identity for any candidate nucleic acid or polypeptide relative to a reference nucleic acid or polypeptide may be determined by aligning a reference sequence to one or more test sequences using, for example, the computer program ClustalW (version 1.83, default parameters), which enable nucleic acid or polypeptide sequence alignments across their entire lengths (global alignment) or across a specified length. The number of identical matches in such a ClustalW alignment is divided by the length of the reference sequence and multiplied by 100.

Also included are nucleic acid molecules capable of hybridizing to the complement of a sequence encoding the proteins of the disclosure under stringent or moderately stringent conditions. See e.g. Ausubel, et al., CURRENT PROTOCOLS IN MOLECULAR BIOLOGY, John Wiley & Sons, New York, N.Y., 1993, and below. An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing an S1-Fragment-Specific Binding Moiety

The moieties, conjugates, and VNAR antibodies of the disclosure may be manufactured by standard synthetic methods, by use of recombinant expression systems, or by any other suitable method. Thus, these entities may be synthesized in a number of ways, including, e.g., methods comprising: (1) synthesizing a polypeptide or polypeptide component thereof using standard solid-phase or liquid-phase methodology, either stepwise or by fragment assembly, and isolating and purifying the final peptide compound product; (2) expressing a nucleic acid construct that encodes the polypeptide or polypeptide component thereof in a host cell and recovering the expression product from the host cell or host cell culture; or (3) cell-free in vitro expression of a nucleic acid construct encoding the polypeptide or polypeptide component thereof, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a moiety, conjugate, or VNAR antibody of the disclosure by means of solid-phase or liquid-phase peptide synthesis. Such molecules may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present disclosure also relates to methods for producing a moiety, conjugate, or VNAR antibody of the disclosure according to above recited methods; a nucleic acid molecule encoding part or all of such polypeptides, a vector comprising at least one nucleic acid of the disclosure, expression vectors comprising at least one nucleic acid of the disclosure capable of producing a moiety, conjugate, or VNAR antibody of the disclosure when introduced into a host cell, and a host cell comprising a nucleic acid molecule, vector or expression vector of the disclosure invention.

The moieties, conjugates, and VNAR antibodies of the disclosure may be prepared using recombinant techniques well known in the art. In general, methods for producing such polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available and suitable for use.

Expression vectors capable of directing transient or stable expression of genes and having promoters operably linked to such genes are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce moieties, conjugates, and VNAR antibodies of the disclosure. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, *Arabidopsis*, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a moiety, conjugate, or VNAR antibody of the present disclosure can be accomplished using standard techniques known in the art. Mammalian cells are preferred host cells for expression of polypeptides. Particularly useful mammalian cells include, inter alia, HEK 293, NSO, DG-44, and CHO cells, but any other suitable host cell may be used according to the invention. Preferably, the moieties, conjugates, or VNAR antibodies of the disclosure are secreted into the medium in which the host cells are cultured, from which the moieties, conjugates, or VNAR antibodies of the disclosure may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a S1-binding moiety, conjugate, or VNAR antibody of the disclosure.

Methods of Treatment

In an aspect, the disclosure provides a method of passive immunization against SARS-CoV-2, and variants thereof, which comprises administering a pharmaceutical composition of the disclosure to a subject in need thereof.

In another aspect, the disclosure provides a method of preventing or treating COVID-19 which comprises administering a pharmaceutical composition of the disclosure to a mammal or a subject for a time and in an amount effect to treat or prevent COVID-19.

Such compositions are described in more detail below but include pharmaceutical compositions comprising at least one S1-specific binding moiety, conjugate or VNAR antibody of the disclosure. In embodiments, such compositions can also have, independently, two, three, four, five or more moieties, conjugates or VNAR antibodies of the disclosure.

In accordance with the foregoing, the moieties, conjugates, and VNAR antibodies of the disclosure can be used the preparation of a medicament to for passive immunization against SARS-CoV-2 and viral variants (mutants) thereof or to treat or prevent COVID-19 in a mammalian subject in need thereof.

In embodiments of these methods, the subject or mammal has tested positive for SARS-CoV-2. In embodiments of these methods, the subject or mammal has suspected exposure to SARS-CoV-2 and/or tested negative for SARS-CoV-2. In some embodiments of these methods, the composition is preferably administered intravenously, subcutaneously, intramuscularly, intranasally or by inhalation.

Pharmaceutical Compositions. Administration and Dosing

A further aspect relates to pharmaceutical compositions comprising at least one moiety, conjugate, or VNAR antibody of the disclosure. In embodiments, such compositions can also have, independently, two, three, four, five or more of such moieties, conjugates or VNAR antibodies. The moieties, conjugates and VNAR antibodies may be present as a pharmaceutically acceptable salt or solvate, together with a pharmaceutically acceptable carrier, excipient or vehicle. Certain embodiments of the pharmaceutical compositions of the invention are described in further detail below.

The moieties, conjugates and VNAR antibodies of the present disclosure (and for convenience may also be referred to as compounds), or salts thereof, may be formulated as pharmaceutical compositions prepared for storage or administration, which typically comprise a therapeutically effective amount of a compound of the disclosure, or a salt thereof, in a pharmaceutically acceptable carrier.

The therapeutically effective amount of a moiety, conjugate or VNAR antibody of the present disclosure will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention and may be confirmed by clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically-acceptable salt" refers to the salt of the compounds. As used herein a pharmaceutically-acceptable salt retains qualitatively a desired biological activity of the parent compound without imparting any undesired effects relative to the compound. Salts include pharmaceutically acceptable salts such as acid addition salts and basic salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and di-carboxylic acids, phenyl-substituted alkanoic acids, hydroxy alkanoic acids, aromatic acids, aliphatic and aromatic sulfonic acids and the like. Examples of basic salts include salts where the cation is selected from alkali metals, such as sodium and potassium, alkaline earth metals such as calcium and magnesium, and ammonium ions $^+N(R^3)_3(R^4)$, where $R^3$ and R independently designate optionally substituted $C_{1-6}$alkyl, optionally substituted $C_{2-6}$alkenyl, optionally substituted aryl, or optionally substituted heteroaryl, and more specifically, the organic amines, such as N, N'-dibenzylethylenediamine, N-methylglucamine, chloroprocaine, choline, diethanolamine, ethylenediamine, procaine and the like. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one moiety, conjugate or VNAR antibody of the present disclosure, or a combination of different such or a combination of different such moieties, conjugates or VNAR antibodies, and at least one pharmaceutically acceptable carrier.

Pharmaceutical compositions of the invention may be administered alone or in combination with one or more other therapeutic or diagnostic agents. A combination therapy may include a moiety, conjugate or VNAR antibody of the present disclosure combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the conjugate of the invention may be coated in a material or materials intended to protect the compound from the action of acids and other natural inactivating conditions to which the active conjugate may encounter when administered to a subject by a particular route of administration.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

Pharmaceutical compositions of the disclosure may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active conjugate of the invention. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a conjugate of the invention in the required amount in an appropriate solvent with one or a combination of ingredients described above, as required, followed by sterilization microfiltration.

Dispersions may be prepared by incorporating the active compound into a sterile vehicle that contains dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a moiety, conjugate or VNAR antibody of the present disclosure is administered by, e.g., intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a moiety, conjugate or VNAR antibody of the present disclosure, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. The moieties, conjugates or VNAR antibodies of the present disclosure will typically be administered on multiple occasions. Intervals between single dosages can be, for example, 2-5 days, weekly, monthly, every two or three months, every six months, or yearly.

In certain embodiments, two or more moieties, conjugates or VNAR antibodies of the present disclosure with different binding properties may be administered simultaneously or sequentially, in which case the dosage of each administered compound may be adjusted to fall within the ranges described herein.

In certain embodiments, a moiety, conjugate or VNAR antibody of the present disclosure may be administered as a sustained release formulation, in which case less frequent administration is required. Dosage and frequency vary depending on the half-life of the conjugate in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the moiety, conjugate or VNAR antibody of the present disclosure alone or in combination with one or more other active ingredients in the pharmaceutical compositions may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular conjugate or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Therapeutic compounds or compositions of the invention may be administered with one or more of a variety of medical devices known in the art. For example, in one embodiment, a therapeutic conjugate of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

EXAMPLES

The examples presented herein represent certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1. OSX6 Phage Library Generation

The OSX6 library was designed based on natural diversity found in the VNAR scaffold that occurs during the nurse shark immune response. Nurse sharks were immunized with a variety of immunogens and blood samples were collected pre- and post-immunization at different time points from 6 animals in total producing 30 individual immune repertoire libraries that were subsequently analyzed by next-generation sequencing (NGS). The most common type II VNAR N-termini were identified and overlapping oligonucleotides encoding selected N-terminal fragments covering residues 1-84 with canonical cysteines in positions 22, 29 and 83 were synthesized containing residue substitutions depicted in Table 1. The CDR1, HV2 and HV4 regions (bolded) cover positions 26-33, 44-52 and 61-65, respectively. The library was generated by enzymatic ligation of 1068 different N-terminal fragments-encoding oligonucleotides with approximately 1×10⁶ of C-terminal fragments-encoding oligonucleotides containing the CDR3 that were synthesized following residue representation instructions outlined in Table 2. The CDR3 fragment covers residues 85-100 with a canonical cysteine in position 91.

The CDR3 region within C-terminal fragment was designed based on NGS analysis of the immune repertoire libraries, which had the most common lengths for CDR3 as 15, 16 and 17 residues with canonical cysteine located approximately in the middle of CDR3 (Table 2). For the OSX6 library, the amino acid representation in each position for positions 85-100 of the C-terminal fragments was as follows:

X(4)[Y/L/D/S/G][D/V/W/Y/G]C[W/E/Y/D/G/][Y/L/D/V/L]X(5)[D/G][V/L].

Figure 1:
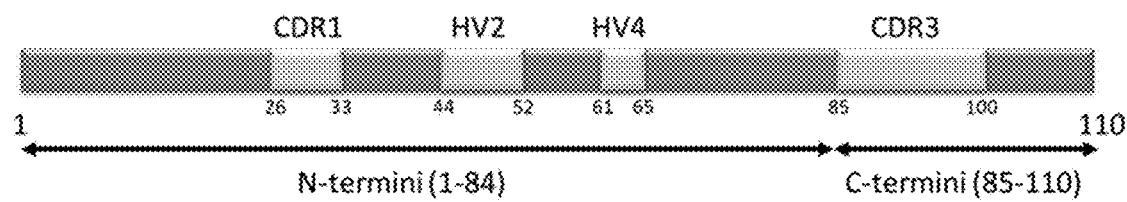
FIG. 1. Schematic representation of VNAR domain variable regions. Variable regions include CDR1 (26-33), HV2 (44-52), HV4 (61-65) and CDR3 (85-100). The OSX6 phage library was generated by random assembly of 1068 synthesized N-terminal fragments designed as provided in Table 1 with approximately $1 \times 10^6$ C-termini fragments designed as provided in Table 2.

In addition, the randomized C-terminal fragments were designed to exclude potentially detrimental motifs such as: glycosylation (NxS NxT, where x is not P), asparagine deamidation (NG, NS, NT, NH), aspartate isomerization (DG, DS, DT, DD), lysine glycation (LE, LD, LL), integrin binding αVβ3 (ROD, RYD, KGD, NGR), integrin binding α4β1 (LDV), integrin binding α2β1 (DGE), CD11c/CD18 binding (GRP), fragmentation (DP, DQ) and hydrophobicity (FF, FW, WW, WF). A schematic of VNAR domain structure is shown in FIG. 1, with the N- and C-terminal fragments indicated below the domain.

After ligation, the final OSX6 library size and diversity was approximately 1×10⁹. The full OSX6 library was cloned into the expression vector phagemid pOsD2, a modified version of pSEX81 (Progen) in which a 6×His tag (SEQ ID NO: 169), a FLAG tag, and an amber stop codon were inserted between the VNAR domain (inserted into SfiI sites) and the full-length PIII protein of the M13 phage as described in U.S. Pat. No. 10,479,990.

Overall, the OSX6 phage library has a framework as well as a CDR3 loop closely resembling the natural repertoire of VNAR domains found in nurse sharks. The framework diversity included modifications to the germline sequence that spread across the whole VNAR scaffold and were not limited to CDR1, HV2, HV4 and CDR3. Such a design, without being bound to a theory, should increase stability, expression yields and developability, thus increasing the success rate for the discovery of functional antibodies despite reduced diversity in CDR3 loop. In addition, the direct synthesis of the fragments used for generation of the OSX6 library, rather than the use of the degenerate NNK codon method, assured a high level of accuracy and nearly exact match between theoretical and achieved design. The direct synthesis also allowed the removal of know liability motifs including glycosylation, asparagine deamidation, aspartate isomerization, lysine glycation, integrin binding, CD11c/CD18 binding, fragmentation and hydrophobicity patches that further improved developability characteristics of VNAR domains isolated from the OSX6 library.

TABLE 1

Amino Acid Residues For N-Terminal VNAR Fragments

| #residue position | Allowed Amino Acids |
|---|---|
| 1 | A                                            T |
| 2 | R      V |
| 3 | V |
| 4 | D |
| 5 | H      Q |
| 6 | T |
| 7 | P |
| 8 | D E    H I K L    P Q R S T V |
| 9 | E      I K L        R S T V |
| 10 | E        I   L          S T V |
| 11 | G I K L    R   T V |
| 12 | E        K      Q R T |
| 13 | D E G   K L N P Q R V |
| 14 | E          L    P Q R S T |
| 15 | D G R |
| 16 | D E G K S |
| 17 | E L S |
| 18 | L T V |
| 19 | I L R S T |
| 20 | F I L T V |
| 21 | D F I K N R S T Y |
| 22 | C |
| 23 | D E F G I L N T V Y |
| 24 | D E G I L P Q R S V |
| 25 | D E G I L N P Q R S T V |
| 26 | D E G H I L N Q T V Y |
| 27 | D E F G I K L N P R S T V W Y |
| 28 | D E F G H I K L N P Q R S T V Y |
| 29 | C |
| 30 | D E F G I K L P Q R S T V |
| 31 | D E F G I K L P R S T V W Y |
| 32 | D E F G H I K L P Q R S T V W Y |
| 33 | D E F G H I K L N P R S T V W Y |
| 34 | G I K L N P R S T V W |
| 35 | D E F G H I L N R S T W Y |
| 36 | F W Y |
| 37 | D E F G H I K L N R S T V W Y |

TABLE 1-continued

Amino Acid Residues For N-Terminal VNAR Fragments

| #residue position | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 38 |  |  |  |  | F |  | H | I |  | L |  |  |  | Q | R | S |  |  | W | Y |
| 39 |  |  |  | E |  | G |  | I | K | L |  | N |  | Q | R | S | T | V |  | Y |
| 40 |  |  | D | E | F | G | H | I | K | L |  | N | P | Q | R | S | T | V |  |  |
| 41 |  |  |  | E | F | G |  |  | K | L |  |  | P | Q |  | S | T | V | W | Y |
| 42 |  |  | D | E | F | G |  |  |  |  |  |  | P |  | R |  | T | V |  |  |
| 43 |  |  | D | E | F | G |  |  | K | L |  |  | P |  | R | S | T | V | W | Y |
| 44 |  |  | D | E |  | G |  | I | K | L |  |  | P | Q | R | S | T | V |  |  |
| 45 |  |  | D | E | F | G | H | I | K | L |  | N | P | Q | R | S | T | V |  | Y |
| 46 |  |  | D | E |  |  |  |  | K | L |  |  | P | Q | R |  |  |  | W | Y |
| 47 |  |  | D | E |  | G |  |  | K | L |  |  |  | Q | R |  | T | V | W | Y |
| 48 |  |  | D | E |  | G |  | I | K | L |  | N | P |  | R | S | T | V |  |  |
| 49 |  |  |  |  |  |  |  | I |  | L |  |  |  |  | R |  | T | V |  |  |
| 50 |  |  | D | E | F | G |  | I | K | L |  | N | P |  | R | S | T |  | W | Y |
| 51 |  |  |  | E |  | G | H | I | K | L |  | N | P | Q | R | S | T | V |  |  |
| 52 |  |  | D | E | F | G | H | I |  |  |  |  |  |  | R | S | T | V |  | Y |
| 53 |  |  |  |  |  | G |  |  |  | L |  | N |  |  | R | S | T |  |  | Y |
| 54 |  |  |  |  |  |  |  |  |  | L |  |  |  | Q | R |  |  |  |  |  |
| 55 |  |  | D |  | F |  | H |  |  | L |  | N |  |  |  | S | T | V |  | Y |
| 56 |  |  |  |  | F | G |  | I | K | L |  |  |  |  | R | S | T | V |  |  |
| 57 |  |  |  | E |  | G |  | I | K |  |  |  |  | Q | R |  |  | V |  |  |
| 58 |  |  |  | E |  |  |  | I | K |  |  | N |  |  | R | S | T |  |  |  |
| 59 |  |  |  | E | F | G | H | I | K | L |  | N |  |  | R | S | T | V |  | Y |
| 60 |  |  | D |  |  | G | H | I | K | L |  | N | P |  | R | S | T | V |  | Y |
| 61 |  |  |  |  | F | G |  | I | K | L |  |  |  | Q | R | S | T | V |  | Y |
| 62 |  |  | D | E | F | G |  |  | K | L |  |  | P | Q | R | S |  | V |  |  |
| 63 |  |  |  | E | F | G |  |  | K | L |  |  |  |  | R | S | T | V |  |  |
| 64 |  |  |  | E |  |  |  | I | K | L |  | N |  | Q | R | S | T |  |  |  |
| 65 |  |  |  |  | F |  | H |  |  | L |  |  | P |  |  | S | T | V |  | Y |
| 66 |  |  |  |  | F | G |  | I |  | L |  |  |  |  |  | S |  | V | W |  |
| 67 |  |  |  |  | F |  |  |  |  | L |  |  | P |  | R | S | T |  | W | Y |
| 68 |  |  |  |  | F |  |  |  |  | L |  |  |  |  |  |  |  |  |  |  |
| 69 |  |  |  |  |  | G |  | I | K | L |  |  |  |  | R | S | T |  |  |  |
| 70 |  |  |  |  | F |  |  | I |  |  |  |  |  |  |  |  |  | V |  |  |
| 71 |  |  |  |  |  |  | H |  | K |  |  | N |  |  |  | S | T |  |  | Y |
| 72 |  |  | D | E | F | G | H |  |  |  |  | N |  |  |  | S |  | V |  | Y |
| 73 |  |  |  |  |  |  |  | I |  | L |  |  |  |  |  |  |  | V |  |  |
| 74 |  |  | D |  |  | G | H | I | K | L |  | N |  | Q | R | S | T | V |  |  |
| 75 |  |  | D | E | F | G | H | I |  | L |  | N |  |  | R | S | T | V |  | Y |
| 76 |  |  |  | E |  | G |  |  | K | L |  |  |  | Q | R | S | T | V |  |  |
| 77 |  |  | D |  |  | G | H |  |  |  |  | N |  |  |  |  |  |  |  |  |
| 78 |  |  |  |  |  |  |  |  | K |  |  |  |  |  | R | S | T |  |  |  |
| 79 |  |  | D |  |  | G |  |  |  |  |  |  |  |  |  |  |  | V |  |  |
| 80 |  |  |  | E | F | G |  | I | K | L |  |  |  |  | R | S | T | V | W |  |
| 81 |  |  |  |  | F |  |  |  |  |  |  |  |  |  |  |  |  |  | W | Y |
| 82 |  |  |  |  |  | G |  |  | K | L |  |  |  | Q | R | S | T | V |  |  |
| 83 |  | C |  |  |  |  |  |  |  |  |  |  |  |  |  |  |  |  |  |  |
| 84 |  |  | D | E | F | G | H | I | K | L |  | N | P | Q | R | S | T | V | W | Y |

TABLE 2

Amino Acid Residues For C-Terminal VNAR Fragments

| #residue position | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 85 | A |  | D | E | F | G | H | I | K | L | M | N | P | Q | R | S | T | V | W | Y |
| 86 | A |  | D | E | F | G | H | I | K | L | M | N | P | Q | R | S | T | V | W | Y |
| 87 | A |  | D | E | F | G | H | I | K | L | M | N | P | Q | R | S | T | V | W | Y |
| 88 | A |  | D | E | F | G | H | I | K | L | M | N | P | Q | R | S | T | V | W | Y |
| 89 |  |  | D |  |  | G |  |  |  | L |  |  |  |  |  | S |  |  |  | Y |
| 90 |  |  | D |  |  | G |  |  |  |  |  |  |  |  |  |  |  | V | W | Y |
| 91 |  | C |  |  |  |  |  |  |  |  |  |  |  |  |  |  |  |  |  |  |
| 92 |  |  | D | E |  | G |  |  |  |  |  |  |  |  |  |  |  |  | W | Y |
| 93 |  |  | D |  |  |  |  |  |  | L |  |  |  |  |  |  |  | V |  | Y |
| 94 | A |  | D | E | F | G | H | I | K | L | M | N | P | Q | R | S | T | V | W | Y |
| 95 | A |  | D | E | F | G | H | I | K | L | M | N | P | Q | R | S | T | V | W | Y |
| 96 | A |  | D | E | F | G | H | I | K | L | M | N | P | Q | R | S | T | V | W | Y |
| 97 | A |  | D | E | F | G | H | I | K | L | M | N | P | Q | R | S | T | V | W | Y |
| 98 | A |  | D | E | F | G | H | I | K | L | M | N | P | Q | R | S | T | V | W | Y |
| 99 |  |  | D |  |  | G |  |  |  |  |  |  |  |  |  |  |  |  |  |  |
| 100 |  |  |  |  |  |  |  |  |  | L |  |  |  |  |  |  |  | V |  |  |
| 101 |  |  |  |  |  |  |  |  |  |  |  |  |  |  |  |  |  |  |  | Y |

TABLE 2-continued

Amino Acid Residues For C-Terminal VNAR Fragments

| #residue position | Allowed amino acids |
|---|---|
| 102 | G |
| 103 | D G |
| 104 | G |
| 105 | T |
| 106 | A V |
| 107 | V |
| 108 | T |
| 109 | V |
| 110 | N |

Example 2. Phage Display Selection to Identify VNARs to S1 and S1-RBD

Overview. The phage selection process was performed with two different Type II VNAR semi-synthetic libraries, the OSX3 library described in U.S. Pat. No. 10,479,990, and the OSX6 library prepared as described in Example 1. The OSX3 library contains approximately $1.6 \times 10^{10}$ unique sequences with CDR3 lengths from 11 to 18 amino acids and a flexible position for the canonical cysteine in the CDR3 loop. The OSX6 library contains a single length CDR3 of 14 amino acid residues with a centrally fixed canonical cysteine within approximately $10^{-3}$ framework variants identified from naïve and immune repertoire libraries by NGS.

Expression and Purification of S1, S1-RBD and ACE2. SARS-CoV-2 spike protein (Accession: YP 009724390.1) S1 domain (amino acids 16-685) and S1-RBD domain (amino acids 319-541) (FIG. 2) were synthesized and cloned into the pFUSE expression vector (InvivoGen). Both constructs contained AVI and 6xHis tags (SEQ ID NO: 169) at the C-terminal end separated by G4S linkers (SEQ ID NO: 170). ACE2 (UnitProt entry: Q9BYF1) ectodomain (amino acids 18-740) was synthesized with FLAG and 6xHis tags (SEQ ID NO: 169) at the C-terminal end separated by G4S linkers (SEQ ID NO: 170) before cloning into the pFUSE vector. S1, S1-RBD and ACE2 recombinant proteins were expressed in Expi293 cells for 5 days following transient transfection using Expifectamine 293 Transfection Kit (Thermo Fisher Scientific). Cell cultures were centrifuged at 4500 g for 40 min, supernatants were collected and filtered on 0.45 µm membranes before being loaded on a HisTrap Excel column (Cytiva). After extensive washing, the proteins were eluted with 500 mM imidazole, concentrated and buffer exchanged to PBS pH 7.4 using HiPrep 26/10 desalting columns. The quality of the purified proteins was assessed by sodium dodecyl sulfate polyacrylamide gel electrophoresis (SDS-PAGE) and analytical size exclusion chromatography (SEC) using a Superdex 200 Increase 10/300 GL analytical column (Cytiva).

Phage selections. Phage selection was performed against the S1-RBD domain (Trenzyme) and S1 subunit of SARS-CoV-2 spike protein, which were biotinylated using EZ-Link Sulfo-NHS-Biotin reagent (Pierce). PEG/NaCl precipitated phage libraries blocked in 5% BSA in PBS were deselected with streptavidin magnetic beads prior to bio-panning against biotinylated S1 or S1-RBD. Phage bound to biotinylated target protein were captured by streptavidin coupled Dynabeads (Thermo Fisher Scientific), washed and eluted in 100 nM triethylamine. Eluted phages were adjusted to neutral pH and propagated in TG1 E. coli. M13KO7 helper phage was used to induce phage production for subsequent rounds of selection. The amount of antigen used in each subsequent selection round was 100, 50, and 25 nM for round 1, 2 and 3, respectively.

Phage ELISA. Individual clones were picked from agar plates and grown at 37° C. with shaking in a 96-well block in 2YT media supplemented with 2% glucose and 100 µg/ml ampicillin until visible growth occurred. The cultures were super-infected with M13K07 helper phage (New England Biolab) for 1 hr and the media was replaced with 2YT media supplemented with 100 µg/ml ampicillin and 50 µg/ml kanamycin. After 16 hr at 30° C., supernatants were collected by centrifugation and blocked in a final concentration of 2.5% milk in PBS with 0.1% Tween-20 (PBST) for 1 hr at room temperature (RT). High binding, 96 well microplates (Greiner) were coated with 100 µl (5 µg/ml) of purified S1 or S1-RBD or commercial human serum albumin (HSA; Sigma-Aldrich) and incubated overnight at 4° C. Plates were blocked with 2.5% milk in PBST for 1 hr at RT. Blocked phage supernatants were transferred to blocked microplates and incubated for 1 hr followed by washing with PBST on a plate washer (BioTek). Anti-M13-HRP antibody (Sino Biological) was used for detection at 1:4000 dilution in blocking buffer. The reaction was developed with 1-Step Ultra TMB-ELISA Substrate Solution (Thermo Fisher Scientific), stopped with 1% HCl and absorbance was measured at 450 nm on VarioSkan plate reader (Thermo Fisher Scientific).

Results. Three rounds of selection with the OSX3 and OSX6 libraries produced 149 unique VNAR clones as identified by DNA sequencing. The VNX3 library produced 60 and 40 clones from selection with S1-RBD and S1, respectively (Table 3). The OSX6 library produced 34 and 15 clones from selection with S1-RBD and S1, respectively (Table 4). The SEQ ID NO. is also used as the name for the VNAR clone or VNAR domain having that sequence. The CDR1, HV2, HV4 and CDR3 sequences of VNARs identified from the OSX3 and OSX6 libraries, respectively are also listed in Tables 5 and 6.

The specific binding of all 149 clones to either S1 or S1-RBD was confirmed by phage ELISA. The lower number of unique clones obtained from OSX6 in comparison to OSX3 library was likely a consequence of lower CDR3 diversity in the OSX6 library.

TABLE 3

VNAR Domains from the OSX3 Type II VNAR library

| SEQ ID NO | Sequence | VNAR Type | Select. Antigen |
|---|---|---|---|
| 1 | ARVDQTPRSVTKETGESLTINCVLRDNNCALSTTYWYRKKSGSTNEESISKGGRYVETVNSGSKSFSLRINDLTVEDSGTYRCKVRRVPHNCFPGDVIDWDVYGDGTAVTVNA | II | S1-RBD |
| 2 | ARVDQTPQTITKETGESLTINCVLRDSNCALSNLYWYRKKSGSTNEESISKGGRYVETVNSGSKSFSLRINDLVVEDSGTYRCNVMAWFGEECLEDYPDVYGDGTAVTVNA | II | S1-RBD |
| 3 | ARVDQTPQTITKETGESLTINCVLRDSNCALSSTYWYRKKSGSTNEENISKGGRYVETVNSGSKSFSLKINDLTVEDSGTYRCNVQTSWRRNCDARVDVYGDGTAVTVNA | II | S1-RBD |
| 4 | ARVDQTPQTITKETGESLTINCVLRDSNCALSSTYWYRKKSGSTNEENISKGGRYVETVNSGSKSFSLRINDLTVEDSGTYRCKVVALDPVMGTSCGRAGWDVYGGGTVVTVNA | II | S1-RBD |
| 5 | ARVDQTPQTITKETGESLTINCVLRDSNCALPSTYWYRKKSGSTNEESISKGGRYVETVNSGSKSFSLRINDLTVKDSGTYRCKVWQHECAGDYLLGLAGDVYGDGTAVTVNA | II | S1-RBD |
| 6 | ARVDQTPQTITKETGESLTINCVLRDSNCALPSTYWYRKKSGSTNEENISKGGRYVETVNSGSKSFSLRINDLTVEDSGTYRCNVLWLVGCHPQGDVYGDGTAVTVNA | II | S1-RBD |
| 7 | ARVDQTPQTITKETGESLTINCVLRDSNCALPSTYWYRKKSGSTNEESISKGGRYVETVNSGSKSFSLRINDLTVEDSGTYRCKVESQWTGRENRCVWVIADVYGDGTAVTVNA | II | S1-RBD |
| 8 | ARVDQTPQTITKETGESLTINCVLRDSNCALSSTYWYRKKSGSTNEENISKGGRYVETVNSGSKSFSLRINDLTVEDSGTYRCKVVALDPVMRTSCGRAGWDVYGGGTVVTVNA | II | S1-RBD |
| 9 | ARVDQTPRSVTKETGESLTINCVLRDSICALSSTHWYRKKSGSTNEESISKGGRYVETVNSGSKSFSLKINDLTVEDSGTYRCNVSFYPNSWCWNRQKDVYGGGTAVTVNA | II | S1-RBD |
| 10 | ARVDQTPQTITKETGESLTINCVLRDSNCALPSTYWYRKKSGSTNEESISKGGRYVETVNSGSKSFSLRINDLTVKDSGTYRCKVHEIVSAVCGFTQVKDVYGGGTVVTVNA | II | S1-RBD |
| 11 | ARVDQTPQTITKETGESLTINCVLRDSNCALSSTYWYRKKSGSTNEESISKGGRYVETVNSGSKSFSLRINDLTVEDSGTYRCKVFAVRPPMMHLCSRGQSDVYGGGTVVTVNA | II | S1-RBD |
| 12 | ARVDQTPRSVTKETGESLTINCVLRDASYALGSTYWYRKKSGSTNEENISKGGRYVETVNSGSKSFSLKINDLTVEDSGTYRCNVLVWSNGTVGMDVYGGGTVVTVNA | II | S1-RBD |

TABLE 3-continued

VNAR Domains from the OSX3 Type II VNAR library

| SEQ ID NO | Sequence | VNAR Type | Select. Antigen |
|---|---|---|---|
| 13 | ARVDQTPQTITKETGESLTINCVLRDSNCDLSRTYWYRKKSGSTN EESISKGGRYVETVNSGSKSFSLRINDLVVEDSGTYRCKVAPGWA GMWGRAACDVYGGGTVVTVNA | II | S1-RBD |
| 14 | ARVDQTPQTITKETGESLTINCVLRDSNCALPSTYWYRKKSGSTN EESISKGGRYVETVNSGSKSFSLRINDLTVKDSGTYRCKVSRYVL ERHSVCFHSLADVYGGGTVVTVNA | II | S1-RBD |
| 15 | ARVDQTPQTITKETGESLTINCVLRDSNCALSSTYWYRKKSGSTN EESISKGGRYVETVNSGSKSFSLRINDLTVEDSGTYRCKVASVDV NPSPQGPVQVVYGGGTVVTVNA | II | S1-RBD |
| 16 | ARVDQTPQTITKETGESLTINCVLRDSNCALPSTYWYRKKSGSTN EESISKGGRYVETVNSGSKSFSLRINDLTVKDSGTYRCKVHENLY SHCQFSLPTDVYGGGTVVTVNA | II | S1-RBD |
| 17 | ARVDQTPQTITKETGESLTINCVLRDNNCALSTTYWYRKKSDSTN EESISKGGRYVETVNSGSKSFSLRINDLTVEDSGTYRCNVFAYYP QYCNVLAQDVYGGGTVVTVNA | II | S1-RBD |
| 18 | ARVDQTPQTITKETGESLTINCVLRDSNCDLSRTYWYRKKSGSTN EESISKGGRYVETVNSGSKSFSLRINDLTVEDSGTYRCKVPIFGW VGFCDLTWDDVYGDGTAVTVNA | II | S1-RBD |
| 19 | ARVDQTPQTITKETGESLTINCVLRDSNCALSNLYWYRKKSGSTN EESISLGGRYVETVNSGSKSFSLRINDLTVEDSGTYRCKVKLVHA VGGEGCSGALIDVYGGGTAVTVNA | II | S1-RBD |
| 20 | ARVDQTPQTITKETGESLTINCVLRDSICALSSTHWYRKKSGSTN EARISKGGRYVETVNSGSKSFSLRINDLTVEDSGTYRCNVQVHPQ AACGQHLDVYGGGTAVTVNA | II | S1-RBD |
| 21 | ARVDQTPQTITKETGESLTINCVLRDSNCALSSTYWYRKKSDSTN EESISKGGRYVETVNSGSKSFSLRINDLTVEDSGTYRCKVFQYCE EDCWGIWEWDVYGGGTAVTVNA | II | S1-RBD |
| 22 | ARVDQTPQTITKETGESLTINCVLRDSNCALPSTYWYRKKSGSTN EESISKGGRYVETVNSGSKSFSLRINDLTVEDSGTYRCNVEGFLG SCDSMWWDDVYGDGTAVTVNA | II | S1-RBD |
| 23 | ARVDQTPQTITKETGESLTINCVLRDSICALSSTHWYRKKSGSTN EARISKGGRYVETVNSGSKSFSLRINDLTVEDSGTYRCNVQVHPQ AACGQQLDVYGGGTAVTVNA | II | S1-RBD |
| 24 | ARVDQTPRSVTKETGESLTINCVLRDSICALSSTHWYRKKSGSTN EESISKGGRYVETVNSGSKSFSLRINDLTVEDSGTYRCNVVSDCG YSTYDVYGGGTAVTVNA | II | S1-RBD |

TABLE 3-continued

VNAR Domains from the OSX3 Type II VNAR library

| SEQ ID NO | Sequence | VNAR Type | Select. Antigen |
|---|---|---|---|
| 25 | ARVDQTPQTITKETGESLTINCVLRDSICALSSTHWYRKKSGSTN EENISKGGRYVETVNSGSKSFSLKINDLTVEDSGTYRCKVHMEDM NVRDYGGFWGEDVYGGGTVVTVNA | II | S1-RBD |
| 26 | ARVDQTPQTITKETGESLTINCVLRDSICALSSTHWYRKKSGSTN EESISKGGRYVETVNSGSKSFSLRINDLTVEDSGTYRCNVSRGLP GGGGAEWCDVYGGGTVVTVNA | II | S1-RBD |
| 27 | ARVDQTPQTITKETGESLTINCVLRDSNCALSSTLWYRTKSGSRN EESISKGGRYVETVNSGSKSFSLRINDLTVEDSGTYRCKVNVHVD YYSYCTGFDVDVYGGGTAVTVNA | II | S1-RBD |
| 28 | ARVDQTPQTITKETGESLTINCVLRDSNCALSNLYWYRKKSGSTN EESISLGGRYVETVNSGSKSFSLRINDLTVEDSGTYRCKVQNVFW NVCQFHRERDVYGGGTVVTVNA | II | S1-RBD |
| 29 | ARVDQTPQTITKETGESLTINCVLRDSNCDLSRTYWYRKKSGSTN EESISKGGRYVETVNSGSKSFSLRINDLTVKDSGTYRCKVWREPR VCRAALSNGLDVYGGGTAVTVNA | II | S1-RBD |
| 30 | ARVDQTPQTITKETGESLTINCVLRDSNCELSSTYWYRKKSGSTN EARISKGGRYVETVNSGSKSFSLRINDLTVEDSGTYRCNVLAVVE SDGSFMSEDVYGGGTAVTVNA | II | S1-RBD |
| 31 | ARVDQTPQTITKETGESLTINCVLRDSNCALSNLYWYRKKSGSTN EESISLGGRYVETVNSGSKSFSLRINDLTVEDSGTYRCNVPLSFC PWHFDVYGGGTVVTVNA | II | S1-RBD |
| 32 | ARVDQTPQTITKETGESLTINCVLRDSNCALSSTYWYRKKSDSTN EESISKGGRYVETVNSGSKSFSLRINDLTVEDSGTYRCNVRFNCY DHCGDVYGGGTAVTVNA | II | S1-RBD |
| 33 | ARVDQTPQTITKETGESLTINCVLRDSNCALSSTYWYRKKSGSTN EESISKGGRYVETVNSGSKSFSLRINDLTVEDSGTYRCKVFVHDV NVNPGCHPGDVYGGGTAVTVNA | II | S1-RBD |
| 34 | ARVDQTPQTVTKETGESLTINCVLRDSNCALSSTYWYRKKSGSTN EESISLGGRYVETVNSGSKSFSLRINDLTVEDSGTYRCNVRSALG LDGYACWVDVYGGGTVVTVNA | II | S1-RBD |
| 35 | ARVDQTPQTITKETGESLTINCVLRDSNCALSSTYWYRKKSGSTN EENISKGGRYVETVNSGSKSFSLRINDLTVEDSGTYRCKVATIDS LGLGCGMWQGYDVYGGGTVVTVNA | II | S1-RBD |
| 36 | ARVDQTPRSVTKETGESLTINCVLRDNNCALSTTYWYRKKSGSTN EENISKGGRYVETVNSGSKSFSLKINDLVVEDSGTYRCNVSCTFV GYGMLEDVYGGGTAVTVNA | II | S1-RBD |

TABLE 3-continued

VNAR Domains from the OSX3 Type II VNAR library

| SEQ ID NO | Sequence | VNAR Type | Select. Antigen |
|---|---|---|---|
| 37 | ARVDQTPQTITKETGESLTINCVLRDSNCALPSTYWYRKKSGSTN EESISKGGRYVETVNSGSKSFSLRINDLTVEDSGTYRCKVRLESD GWDGAWGWEDVYGDGTAVTVNA | II | S1-RBD |
| 38 | ARVDQTPRSVTKETGESLTINCVLRDSICALSSTHWYRKKSGSTN EESISKGGRYVETVNSGSKSFSLRINDLTVEDSGTYRCKVFTTLN DICHWMWSKDVYGDGTAVTVNA | II | S1-RBD |
| 39 | ARVDQTPQTITKETGESLTINCVLRDSNCALSSTLWYRTKSGSRN EARISKGGRYVETVNSGSKSFSLKINDLTVEDSGTYRCNVLCVQS LRCEFTSEDVYGGGTVVTVNA | II | S1-RBD |
| 40 | ARVDQTPQTITKETGESLTINCVLRDSNCALSSTYWYRKKSGSTN EESISKGGRYVETVNSGSKSFSLRINDLTVEDSGTYRCNVLLMDN YGALRDVYGGGTAVTVNA | II | S1-RBD |
| 41 | ARVDQTPQTITKETGESLTINCVLRDSNCALSSTYWYRKKSGSTN EESISKGGRYVETVNSGSKSFSLRINDLTVEDSGTYRCKVGSYYI LNGGAWRSRADVYGGGTAVTVNA | II | S1-RBD |
| 42 | ARVDQTPQTITKETGESLTINCVLRDSNCALPSTYWYRKKSGSTN EESISKGGRYVETVNSGSKSFSLRINDLTVKDSGTYRCKVRRLPH LCQVETISVWDVYGDGTAVTVNA | II | S1-RBD |
| 43 | ARVDQTPQTITKETGESLTINCVLRDSNCDLSRTYWYRKKSGSTN EESISKGGRYVETVNSGSKSFSLRINDLTVEDSGTYRCNVWQIDD YGHRADVYGGGTAVTVNA | II | S1-RBD |
| 44 | ARVDQTPQTITKETGESLTINCVLRDSNCALSNLYWYRKKSGSTN EESISLGGRYVETVNSGSKSFSLRINDLTVKDSGTYRCNVRTVPL WNDCDVFEDVYGGGTAVTVNA | II | S1-RBD |
| 45 | ARVDQTPQTITKETGESLTINCVLRDSNCALPSTYWYRKKSGSTN EESISKGGRYVETVNSGSKSFSLRINDLVVEDSGTYRCNVVSLFS QGSSFFWDVYGGGTAVTVNA | II | S1-RBD |
| 46 | ARVDQTPRSVTKETGESLTINCVLRDSICALSSTHWYRKKSGSTN EESISKGGRYVETVNSGSKSFSLRINDLTVEDSGTYRCNVNLRSV LPCGWPDVYGDGTAVTVNA | II | S1-RBD |
| 47 | ARVDQTPQTITKETGESLTINCVLRDSNCALSSTYWYRKKSGSTN EESISKGGRYVETVNSGSKSFSLKINDLTVEDSGTYRCKVFQHLA LGYDAMCHVGDVYGGGTAVTVNA | II | S1-RBD |
| 48 | ARVDQTPRSVTKETGESLTINCVLRDSICALSSTHWYRKKSGSTN EESISKGGRYVETVNSGSKSFSLRINDLTVEDSGTYRCNVLEVFC FYGNQGTDVYGDGTAVTVNA | II | S1-RBD |

TABLE 3-continued

VNAR Domains from the OSX3 Type II VNAR library

| SEQ ID NO | Sequence | VNAR Type | Select. Antigen |
|---|---|---|---|
| 49 | ARVDQTPQTITKETGESLTINCVLRDSNCALSSTYWYRKKSDSTN EESISKGGRYVETVNSGSKSFSLRINDLTVEDSGTYRCNVWDLIS MECWWADVYGDGTAVTVNA | II | S1-RBD |
| 50 | ARVDQTPQTITKETGESLTINCVLRDSNCALSSTYWYRKKSGSTN EESISKGGRYVETVNSGSKSFSLRINDLTVKDSGTYRCKVTVLPH VCPDMEPLFVDVYGDGTAVTVNA | II | S1-RBD |
| 51 | ARVDQTPQTVTKETGESLTINCVLRDSNCALSNLYWYRKKSGSTN EESISLGGRYVETVNSGSKSFSLRINDLTVEDSGTYRCNVQFIDY NCGWDVYGGGTVVTVNA | II | S1-RBD |
| 52 | ARVDQTPQTITKETGESLTINCVLRDSNCDLSRTYWYRKKSGSTN EESISKGGRYVETVNSGSKSFSLRINDLTVEDSGTYRCKVISALS WFNDSYQACWVDVYGGGTVVTVNA | II | S1-RBD |
| 53 | ARVDQTPRSVTKETGESLTINCVLRDSICALSSTHWYRKKSGSTN EESISKGGRYVETVNSGSKSFSLKINDLTVEDSGTYRCNVQTSWR RVCDVGMDVYGDGTAVTVNA | II | S1-RBD |
| 54 | ARVDQTPQTITKETGESLTINCVLRDSICALSSTHWYRKKSGSTN EESISKGGRYVETVNSGSKSFSLRINDLTVEDSGTYRCKVGPKVC FRFYGDRSGFDDVYGGGTAVTVNA | II | S1-RBD |
| 55 | ARVDQTPQTITKETGESLTINCVLRDSNCALSSTYWYRKKSGSTN EESISKGGRYVETVNSGSKSFSLRINDLTVEDSGTYRCNVLLQDG YGALNDVYGGGTAVTVNA | II | S1-RBD |
| 56 | ARVDQTPQTITKETGESLTINCVLRDSNCELSSTYWYRKKSGSTN EARISKGGRYVETVNSGSKSFSLRINDLTVEDSGTYRCKVGSLWV KSGGDSWGRRDDVYGGGTVVTVNA | II | S1-RBD |
| 57 | ARVDQTPQTITKETGESLTINCVLRDSNCALSNLYWYRKKSGSTN EESISKGGRYVETVNSGSKSFSLRINDLTVKDSGTYRCKVRRLGC DLDQMFKSWDVYGGGTVVTVNA | II | S1-RBD |
| 58 | ARVDQTPQTITKETGESLTINCVLRDSNCALSSTYWYRKKSGSTN EESISKGGRYVETVNSGSKSFSLRINDLTVEDSGTYRCNVEGFLG SCDSMWWDDVYGDGTAVTVNA | II | S1-RBD |
| 59 | ARVDQTPQTITKETGESLTINCVLRDSNCALSNLYWYRKKSGSTN EESISLGGRYVETVNSGSKSFSLRINDLTVEDSGTYRCKVSVLCL DYYFLGLKLDVYGDGTVVTVNA | II | S1-RBD |
| 60 | ARVDQTPQTVTKETGESLTINCVLRDSNCALSSTLWYRTKSGSRN EESISKGGRYVETVNSGSKSFSLRINDLTVEDSGTYRCNVNELFG SDGNVASDVYGGGTVVTVNA | II | S1-RBD |

TABLE 3-continued

VNAR Domains from the OSX3 Type II VNAR library

| SEQ ID NO | Sequence | VNAR Type | Select. Antigen |
|---|---|---|---|
| 61 | ARVDQTPQTITKETGESLTINCVLRDSICALSSTHWYRKKSGSTN EESISKGGRYVETVNSGSKSFSLKINDLTVEDSGTYRCKVENLPG SGSCLRYYLSDVYGGGTVVTVNA | II | S1 |
| 62 | ARVDQTPQTITKETGESLTINCVLRDSNCALSSTYWYRKKSGSTN EESISKGGRYVETVNSGSKSFSLRINDLTVEDSGTYRCKVVAQGQ LGAIMDVYGGGTVVTVNA | II | S1 |
| 63 | ARVDQTPQTITKETGESLTINCVLRDSNCALSSTYWYRKKSGSTN EESISKGGRYVETVNSGSKSFSLRINDLTVEDSGTYRCKVATSWG GDYSQRYVGSDVYGGGTVVTVNA | II | S1 |
| 64 | ARVDQTPQTITKETGESLTINCVLRDSICALSSTHWYRKKSGSTN EESISKGGRYVETVNSGSKSFSLRINDLTVEDSGTYRCNVIETFP TYGCLGHDVYGGGTVVTVNA | II | S1 |
| 65 | ARVDQTPQTITKETGESLTINCVLRDSNCALSSTYWYRKKSGSTN EENISKGGRYVETVNSGSKSFSLRINDLTVEDSGTYRCNVFAGLP GFCKVLEEDVYGDGTAVTVNA | II | S1 |
| 66 | ARVDQTPQTITKETGESLTINCVLRDSNCALPSTYWYRKKSGSTN EESISKGGRYVETVNSGSKSFSLRINDLTVEDSGTYRCKVWCNAD KGDSKVCCLRDVYGGGTAVTVNA | II | S1 |
| 67 | ARVDQTPQTITKETGESLTINCVLRDSNCALSSTYWYRKKSGSTN EESISKGGRYVETVNSGSKSFSLRINDLTVEDSGTYRCNVFCGNY CCLRDVYGDGTAVTVNA | II | S1 |
| 68 | ARVDQTPQTITKETGESLTINCVLRDSNCALPSTYWYRKKSGSTN EESISKGGRYVETVNSGSKSFSLKINDLTVEDSGTYRCKVREWAC EDDGRVWGWEDVYGDGTAVTVNA | II | S1 |
| 69 | ARVDQTPQTITKETGESLTINCVLRDSICALSSTHWYRKKSGSTN EESISKGGRYVETVNSGSKSFSLKINDLTVEDSGTYRCNVSGWSG YGCLLRDVYGGGTAVTVNA | II | S1 |
| 70 | ARVDQTPQTITKETGESLTINCVLRDSNCALSSTYWYRKKSGSTN EESISKGGRYVETVNSGSKSFSLRINDLTVEDSGTYRCKVYTLWD YCTSADSLAGDVYGGGTAVTVNA | II | S1 |
| 71 | ARVDQTPQTITKETGESLTINCVLRDSNCALPSTYWYRKKSGSTN EESISKGGRYVETVNSGSKSFSLKINDLTVEDSGTYRCKVKEMHV DRVRVLCGDAELDVYGDGTTVTVNA | II | S1 |
| 72 | ARVDQTPRSVTKETGESLTINCVLRDSICALSSTHWYRTKSGSRN EESISKGGRYVETVNSGSKSFSLKINDLTVEDSGTYRCNVGDPFG RYGCLSSDVYGGGTVVTVNA | II | S1 |

TABLE 3-continued

VNAR Domains from the OSX3 Type II VNAR library

| SEQ ID NO | Sequence | VNAR Type | Select. Antigen |
|---|---|---|---|
| 73 | ARVDQTPRSVTKETGESLTINCVLRDSICALSSTHWYRKKSGSTN EESISKGGRYVETVNSGSKSFSLRINDLTVEDSGTYRCNVSGWGG FGCLRVDVYGGGTVVTVNA | II | S1 |
| 74 | ARVDQTPQTITKETGESLTINCVLRDSNCALSSTYWYRKKSGSTN EESISKGGRYVETVNSGSKSFSLRINDLTVEDSGTYRCKVWSHDP YGGACFPPGSRDVYGGGTVVTVNA | II | S1 |
| 75 | ARVDQTPQTITKETGESLTINCVLRDSNCALSSTYWYRKKSGSTN EESISKGGRYVETVNSGSKSFSLRINDLTVEDSGTYRCNVKAMDW YYGHWCGDVYGGGTAVTVNA | II | S1 |
| 76 | ARVDQTPRSVTKETGESLTINCVLRDSNCALSNLYWYRKKSGSTN EESISLGGRYVETVNSGSKSFSLRINDLTVEDSGTYRCNVVSRFY GLCANDRFDVYGDGTAVTVNA | II | S1 |
| 77 | ARVDQTPQTITKETGESLTINCVLRDSNCALSSTYWYRKKSGSTN EESISKGGRYVETVNSGSKSFSLRINDLTVKDSGTYRCKVRMEYE GAGPSGGWVDVYGGGTVVTVNA | II | S1 |
| 78 | ARVDQTPQTITKETGESLTINCVLRDSNCALSNLYWYRKKSGSTN EESISKGGRYVETVNSGSKSFSLKINDLTVEDSGTYRCNVRCISS LCSYWMGDVYGGGTVVTVNA | II | S1 |
| 79 | ARVDQTPRSVTKETGESLTINCVLRDSICALSSTHWYRKKSGSTN EESISKGGRYVETVNSGSKSFSLRINDLTVEDSGTYRCKVASTHN ACIQLTMRSRDVYGGGTAVTVNA | II | S1 |
| 80 | ARVDQTPQTITKETGESLTINCVLRDSNCALSSTYWYRKKSGSTN EESISKGGRYVETVNSGSKSFSLRINDLTVEDSGTYRCNVRSLVS FDGYACWADVYGGGTVVTVNA | II | S1 |
| 81 | ARVDQTPQTITKETGESLTINCVLRDSNCALSSTYWYRKKSGSTN EESISKGGRYVETVNSGSKSFSLRINDLTVEDSGTYRCKVWRHEC AYDYSGPGCHDVYGGGTAVTVNA | II | S1 |
| 82 | ARVDQTPQTITKETGESLTINCVLRDSNCALSNLYWYRKKSGSTN EESISLGGRYVETVNSGSKSFSLRINDLTVEDSGTYRCNVFCTTR LSCYAMFVDVYGDGTAVTVNA | II | S1 |
| 83 | ARVDQTPQTITKETGESLTINCVLRDSNCALSSTYWYRKKSGSTN EESISKGGRYVETVNSGSKSFSLRINDLTVEDSGTYRCKVFLHVA RSGMMCMDQLGDVYGGGTAVTVNA | II | S1 |
| 84 | ARVDQTPQTITKETGESLTINCVLRDSNCALSSTYWYRKKSGSTN EESISKGGRYVETVNSGSKSFSLRINDLTVEDSGTYRCKVLSLDA KYGGFCWIEGADVYGDGTAVTVNA | II | S1 |

TABLE 3-continued

VNAR Domains from the OSX3 Type II VNAR library

| SEQ ID NO | Sequence | VNAR Type | Select. Antigen |
|---|---|---|---|
| 85 | ARVDQTPQTITKETGESLTINCVLRDSNCDLSRTYWYRKKSGSTN EESISKGGRYVETVNSGSKSFSLRINDLVVEDSGTYRCKVFVLNL EYGTICGSSSGDVYGDGTAVTVNA | II | S1 |
| 86 | ARVDQTPQTITKETGESLTINCVLRDSNCALSNLYWYRKKSGSTN EESISLGGRYVETVNSGSKSFSLRINDLTVEDSGTYRCKVKPTEM KWGYGCGGRHWDVYGGGTVVTVNA | II | S1 |
| 87 | ARVDQTPQTITKETGESLTINCVLRDSNCALSSTYWYRKKSGSTN EENISKGGRYVETVNSGSKSFSLRINDLTVEDSGTYRCKVFSHED GNWCGGGDRARDVYGGGTAVTVNA | II | S1 |
| 88 | ARVDQTPQTVTKETGESLTINCVLRDSNCALSSTLWYRTKSGSTN EESISLGGRYVETVNSGSKSFSLRINDLTVEDSGTYRCNVISRFY GICQLGADVYGGGTAVTVNA | II | S1 |
| 89 | ARVDQTPRSVTKETGESLTINCVLRDSICALSSTHWYRKKSGSTN EESISKGGRYVETVNSGSKSFSLRINDLTVEDSGTYRCKVTQFDC ANGYLSAVEADVYGGGTAVTVNA | II | S1 |
| 90 | ARVDQTPQTITKETGESLTINCVLRDSNCALPSTYWYRKKSGSTN EESISKGGRYVETVNSGSKSFSLKINDLTVEDSGTYRCNVYGRDG YCVMADVYGDGTAVTVNA | II | S1 |
| 91 | ARVDQTPQTITKETGESLTINCVLRDSNCALSSTYWYRKKSGSTN EESISKGGRYVETVNSGSKSFSLRINDLTVEDSGTYRCKVWGADD YGSGSDVYGGGTVVTVNA | II | S1 |
| 92 | ARVDQTPQTITKETGESLTINCVLRDSNCELSSTYWYRKKSGSTN EESISKGGRYVETVNSGSKSFSLRINDLTVEDSGTYRCNVLAQDV DYGGLSDVYGGGTAVTVNA | II | S1 |
| 93 | ARVDQTPQTITKETGESLTINCVLRDSNCALPSTYWYRKKSGSTN EESISKGGRYVETVNSGSKSFSLRINDLTVKDSGTYRCNVFNHAT GLCQLWDVYGDGTAVTVNA | II | S1 |
| 94 | ARVDQTPQTITKETGESLTINCVLRDSICALSSTHWYRKKSGSTN EESISKGGRYVETVNSGSKSFSLRINDLTVEDSGTYRCKVVGLYR SVCLSATGADVYGGGTAVTVNA | II | S1 |
| 95 | ARVDQTPQTITKETGESLTINCVLRDSNCALHSTYWYRKKSGSTN EESISKGGRYVETVNSGSKSFSLRINDLTVKDSGTYRCNVIARYY GLCDLDDVYGDGTAVTVNA | II | S1 |
| 96 | ARVDQTPQTITKETGESLTINCVLRDSNCALPSTYWYRKKSGSTN EESISKGGRYVETVNSGSKSFSLRINDLTVEDSGTYRCKVFCSAG LGCYAQFASDVYGDGTAVTVNA | II | S1 |

TABLE 3-continued

VNAR Domains from the OSX3 Type II VNAR library

| SEQ ID NO | Sequence | VNAR Type | Select. Antigen |
|---|---|---|---|
| 97 | ARVDQTPRSVTKETGESLTINCVLRDSICALSSTHWYRKKSGSTN EESISLGGRYVETVNSGSKSFSLRINDLTVEDSGTYRCNVRQLLC GGGPGSDVYGDGTAVTVNA | II | S1 |
| 98 | ARVDQTPQTITKETGESLTINCVLRDSNCDLSRTYWYRKKSGSTN EESISKGGRYVETVNSGSKSFSLKINDLTVEDSGTYRCKVIGYVA NDDYGLRVIDDVYGGGTAVTVNA | II | S1 |
| 99 | ARVDQTPQTITKETGESLTINCVLRDSICALSSTHWYRKKSGSTN EESISKGGRYVETVNSGSKSFSLRINDLTVEDSGTYRCNVLLYGL FPCSSVDVYGGGTAVTVNA | II | S1 |
| 100 | ARVDQTPQTITKETGESLTINCVLRDSNCALSNLYWYRKKSGSTN EESISLGGRYVETVNSGSKSFSLRINDLTVEDSGTYRCKVRRLSH MCLTVSGLSWDVYGGGTAVTVNA | II | S1 |

TABLE 4

VNAR Domains from the OSX6 Type II VNAR library

| SEQ ID NO | Sequence | VNAR Type | Select. Antigen |
|---|---|---|---|
| 101 | ARVDQTPQAITKETGESLTINCVLRDSNCPLSNTYWYRKNSGSTN EERLSNDYRTVETVNSASNSFSLRINDLTVEDTGTYRCSARMYYC DLGHWAPDLYGGGTAVTVNA | II | S1-RBD |
| 102 | ARVDQTPQTITKETGESLTINCVLRDNICTASNTYWYRKKSGSEN EESISKGGRYVETVNSGSKSFSLRINDLTFEDSGTYRCKAIFQSG CGVYHRYTGVYGGGTVVTVNA | II | S1-RBD |
| 103 | ARVDQTPQTITKETGESLTIKCVLQNSICALSSTYWYWKKSGSIN EEEISKGGRYVETINSESKSFSLRINDLTVEDSGTYRCAIVRQSG CEVATFKADVYGGGTVVTVNA | II | S1-RBD |
| 104 | ARVDQTPQTITKETGESLTINCVLRDSVCALSSTYWYRKKSGSTN EESISKGGRYVETINSGSKSFSLRINDLAVEDSGTYRCKSEFKSG CGVFYELTDVYGGGTAVTVNA | II | S1-RBD |
| 105 | ARVDQTPQTITKETGESVTINCVLRDSICALSSTYWYRKKSGSTN EESISKGGRYVETVNSGSKSFSLRINDLTVEDSGTYRCKVARTSG CEVYTYTGDVYGGGTVVTVNA | II | S1-RBD |
| 106 | ARVDQTPQTITKETGESLTINCVLRDSICALSSTYWYRKKSGSRK EESISKGGRYVETVNSGSKSFSLRINDLTIEDSGTYQCKVARTSG CEVYTYTGDVYGGGTVVTVNA | II | S1-RBD |

TABLE 4-continued

VNAR Domains from the OSX6 Type II VNAR library

| SEQ ID NO | Sequence | VNAR Type | Select. Antigen |
|---|---|---|---|
| 107 | ARVDQTPQTITKETGGSVTINCVLLYSDCPLSSTYWYHKKSGSTN EERIRNENRYVETVNSGSKSFSLTINDLTVEDSGTYRCKYGSIDV CYLTNNERDVYGGGTVVTVNA | II | S1-RBD |
| 108 | ARVDQTPQTITKETGESVTINCVLRDSICALSSTYWYRKKSGSTN EESISKGGRYVETVNSGSKSFSLRINDLTVEDSGTYRCAIVRQSG CWVSLHEEDVYGGGTVVTVNA | II | S1-RBD |
| 109 | ARVDQTPQTITKLTGESLTINCVLRDTYCALSNTNWYHKKSGSTH EESISKGGRYVETLNTDSKSFSLRITDLTIEDSGLYRCKTWPVSV CYLTNNERDLYGGGTAVTVNA | II | S1-RBD |
| 110 | ARVDQTPQTITKGTGESLTINCVLRDSRCRLSSTDWYRKKSGSTN EESISKGGRYVETVDSGSKSFSLRINDLTVEDSGTYRCKHRTPYV CGLHSQHPDLYGGGTVVTVNA | II | S1-RBD |
| 111 | ARVDQTPQTITKETGESLTINCVLRDSNCALSSTFWYRKKSGSTN EESISKGGRYVETVNSGSKSFSLRINDLTVEDSGTYRCKIRVVDV CWLEHGTWDVYGGGTAVTVNA | II | S1-RBD |
| 112 | ARVDQTPQTITKETGESLTIKCVARDAHCALDRTYWYRKKSGTTI EESIPIHGRYVETVNSGGKSFSLRVNDLSVEDSGTYRCKIKSFSD CDLGHWAPDLYGGGTAVTVNA | II | S1-RBD |
| 113 | ARVDQTPQTITKETGESLTINCVLRDSNCALSSTYWYRKKSGSLN EESISKGGRYVETVNSGSKSFSLRINDLTVEDSGTYRCNVFRGYD CDVMDVFGGVYGGGTVVTVNA | II | S1-RBD |
| 114 | ARVDQTPQTITKETGESLTINCVLRDSNCVLGSTFWHRTQSGSTN LESIFSGGRYVETVNSGSKSFSLRINDLTVEDSGTYQCNIFVNYD CEDAKYWQGLYGGGTAVTVNA | II | S1-RBD |
| 115 | ARVDQTPQTITKETGESLTINCVLRDSVCALSSTYWYRKKSGSTN EESISKGGRYVETVNSGSKSFSLRINDLTVEDSGTYRCNVKNPSG CGVWYSQEDLYGGGTVVTVNA | II | S1-RBD |
| 116 | ARVDQTPQTITKETGESLTINCVLRDRDCALSSTYWYRKKSGSTN EESISKGGRYVETVNSGSKSFSLRINDLTVEDSGTYRCKAIILYG CELTSDWSDLYGGGTAVTVNA | II | S1-RBD |
| 117 | ARVDQTPQTITKAPGESLTINCVLRDSNCALSSTYWYRKKSGSTN EEGISKGGRYVETVNSGSKSFSLRINDLIVEDSGTYRCKLRTHSD CEDNFVEWGLYGGGTVVTVNA | II | S1-RBD |
| 118 | ARVDQTPQTITKETGESLTINCVLRDSDCALSSTYWYRKKSGSTN EESISKGGRYVETVNSGSKSFSLRINDLTVEDSGTYRCKTWTLYD CDYRWGNQDLYGGGTAVTVNA | II | S1-RBD |

TABLE 4-continued

VNAR Domains from the OSX6 Type II VNAR library

| SEQ ID NO | Sequence | VNAR Type | Select. Antigen |
|---|---|---|---|
| 119 | ARVDQTPQTITKETGESLTINCVLRDSICALSSTYWYRKKSGSTN EESISKGGRYVETVNSGSKSFSLRINDLTVEDSGTYRCKSEFKSG CGVFYELTDVYGGGTVVTVNA | II | S1-RBD |
| 120 | ARVDQTPQTITKETGESLTINCVLRDSNCALSSTYWYRKKSGSTF EESISKGGRYVETVNSGSKSFSLRINDLTVEDSGTYRCAGKVFYD CELYWGMTDVYGGGTVVTVNA | II | S1-RBD |
| 121 | ARVDQTPQTITKETGESLTINCVLRDSICALSSTYWYRKKSGSTN EESISKGGRYVETVNSGSKSFSLRINDLTVEDSGTYRCAIVRQSG CEVHLYQRDLYGGGTAVTVNA | II | S1-RBD |
| 122 | ARVDQTPQTITKETGESLTINCVLRDSNCAVSSTYQYRKKSGSTN EESISKGGRYVETVNSGSKSFSLRINDLTVEDSGTYRCNINLAYY CYLNFEFRDVYGGGTAVTVNA | II | S1-RBD |
| 123 | ARVDQTPQTITKETGESLTIKCVARDAHCALDRTYWYRKKSGTTI EESIPIHGRYVETVNSGGKSFSLRVNDLSVEDSGTYRCKMKRFSD CELGLFIEDVYGGGTVVTVNA | II | S1-RBD |
| 124 | ARVDQTPQTITKLTGESLTINCVLRDTYCALSNTNWYHKKSGSTH EESISKGGRYVETLNTDSKSFSLRITDLTIEDSGLYRCKLHMIGD CELPQNWEDLYGGGTAVTVNA | II | S1-RBD |
| 125 | ARVDQTPQTITKETGESLTINCVLRDSNCALSSAYWYRKKSGSTN EESISKGGRYVETVNSGSKSFSLRINDLTVEDSGTYRCNLQLWDV CGDNWERIGVYGGGTAVTVNA | II | S1-RBD |
| 126 | ARVDQTPQTITKETGESLTINCVLRDNICTASNTYWYRKKSGSEN EESISKGGRYVETVNSGSKSFSLRINDLTFEDSGTYRCKSQSVSG CGVWANEFDVYGGGTAVTVNA | II | S1-RBD |
| 127 | ARVDQTPQTITKLTGESLTINCVLRDTYCALSNTNWYHKKSGSTH EESISKGGRYVETLNTDSKSFSLRITDLTIEDSGLYRCKVARTSG CYVWAWDNDVYGGGTAVTVNA | II | S1-RBD |
| 128 | ARVDQTPQTITKETGESLTINCVIRDSNCALSSTYWYRKKSGSTN EESISKGGRYVETVNSGSKSFSLRINDLTVEDSGTYRCKYWPNYY CELDFGERDLYGGGTAVTVNA | II | S1-RBD |
| 129 | ARVDQTPQTITKETGESLTINCVLRDSNCALSSTYWYRKKSGSTN EEGISKGGRYVETVNSGSKSFSLRINDLTVEDSGTYRCKMNVWYD CGDKGPERGLYGGGTAVTVNA | II | S1-RBD |
| 130 | ARVDQTPQTITKDAGESLTINCVLRDSVCALSSTYWYRKKSGSTN EESISKGGRYVETVAAGTKSFSLRINDLRVEDSGTYRCAIVRQSG CWVYWYETGVYGGGTVVTVNA | II | S1-RBD |

TABLE 4-continued

VNAR Domains from the OSX6 Type II VNAR library

| SEQ ID NO | Sequence | VNAR Type | Select. Antigen |
|---|---|---|---|
| 131 | ARVDQTPQTITKETGESLTINCVLRDSNCALSSTYWYRKKSGSTN EEGISKGGRYVETVNSGSKSFSLRINDLTVEDSGTYRCSYYPQDY CDYFGNYRDLYGGGTVVTVNA | II | S1-RBD |
| 132 | ARVDQTPQTITKETGESLTINCVLRDSNCALSSTNWYRKKTPSTN EENILTGGRYVETVNRGSKSFSLHINDLTIEDSGTYGCNMVFKSV CEDNPYQYGLYGGGTAVTVNA | II | S1-RBD |
| 133 | ARVDQTPQTITKETGESLTIKCVLQNSICALSSTYWYWKKSGSIN EEEISKGGRYVETINSESKSFSLRINDLTVEDSGTYRCAIVRQSG CWVTTSEVDLYGGGTAVTVNA | II | S1-RBD |
| 134 | ARVDQTPQTITKETGESATINCELQNSFCRLSTTYWYRKKSGSTV EETISKGGRYVETVARGSKSFSLRINDLTVEDSGTYRCKIEYLGY CGLWNKFYGLYGGGTVVTVNA | II | S1-RBD |
| 135 | ARVDQTPQTITKETGESLTINCVLRDSICALSSTYWYRKKSGSTN EESISKGGRYVETVNSGSKSFSLRINDLTVEDSGTYRCVIWAHSG CEVITHAMDLYGGGTAVTVNA | II | S1 |
| 136 | ARVDQTPQTITKETGESLTINCVLRDSNCALSSTYWYRKKSGSTN EEGISKGGRYVETVNSGSKSFSLRINDLTVEDSGTYRCKTLYWSY CDLRTGIHDLYGGGTAVTVNA | II | S1 |
| 137 | ARVDQTPQTITKETGESLTINCVLRDSHCALSSTYWYRKKSGSTN EESISKGGRYVETVNSGSKSFSLRINDLTVEDSGTYRCRWVGRLY CGDNEWMQDLYGGGTAVTVNA | II | S1 |
| 138 | ARVDQTPQTITKETGESLTINCVLRDSNCALWSTYWYRKKSGSTN EESISKGGRYVETVNSGSKSFSLRINDLTVEDSGTYRCKMREPLD CGLPNWMYGLYGGGTAVTVNA | II | S1 |
| 139 | ARVDQTPQTITKETGESLTINCVLRDSNCALSSTYWYRKKSGSSY EESISKGGRYVETVNSGSKSFSLRINDLTVEDSGTYRCKTRRIDV CEVKYEFGDVYGGGTAVTVNA | II | S1 |
| 140 | ARVDQTPQAITKETGESLTINCALRDTNCALPGTYWYRKKSGSTN EESISKGGRYVETVNSGSKSFSLRINDLTVEDSGTYRCKVARTSG CWVYWYETGVYGGGTAVTVNA | II | S1 |
| 141 | ARVDQTPQTITKETGESLTINCVLRDSNCALSSTYWYRKKSGSSY EESISKGGRYVETVNSGSKSFSLRINDLTVEDSGTYRCKNRQMDV CWLEHGTWDVYGGGTAVTVNA | II | S1 |
| 142 | ARVDQTPQTITKETGESLTINCVVRDSNCPLAATYWYRKKSASTN EESISKGGRYVETVNSGSKSFSLRINDLTVEDSGTYQCRIRSTDV CYDAMQETGLYGGGTVVTVNA | II | S1 |

TABLE 4-continued

VNAR Domains from the OSX6 Type II VNAR library

| SEQ ID NO | Sequence | VNAR Type | Select. Antigen |
|---|---|---|---|
| 143 | ARVDQTPQTITKLTGESLTINCVLRDTYCALSNTNWYHKKSGSTH EESISKGGRYVETLNTDSKSFSLRITDLTIEDSGLYRCKAKGWGD CYYKWTVNDVYGGGTVVTVNA | II | S1 |
| 144 | ARVDQTPQTLTKETGESLTINCVLRGANCAFDRTYWYRKKSGSTR EESISKGGRYVETVNSGSKSFSLTINDLTIEDSGTYRCAKRWISG CDVPVLAPDLYGGGTAVTVNA | II | S1 |
| 145 | ARVDQTPQTITKETGESLTINCVLRDSNCALSSTYWYRKKSGSTH EESISKGGRYVETVNSGSKSFSLRINDLTVEDSGTYRCKIRQVLD CGYFTGDWDLYGGGTAVTVNA | II | S1 |
| 146 | ARVDQTPQTITKETGESLTINCVLRDSNCDLSTTHWYRKKSDSTN EESISKGGRYVETVSSGSKSFSLRINDLTIEDSGTYRCNKYEFGD CDLTNKWMDVYGGGTAVTVNA | II | S1 |
| 147 | ARVDQTPQTITKETGESLTINCVLVDSNCAESSTYWYRKKSGSTN EESISKGGRYVETVNSGSKSFSLRINDLTVEDSGTYRCKAWEGSW CWVQFLQPGLYGGGTAVTVNA | II | S1 |
| 148 | ARVDQTPQSITKQTGESLTINCVLGDSQCPVEETWWYRKKTGSTN EERISKRGRYVETINSGGKSFSLRINDLTVEDSGTYTCKTDFGGV CWDIWHPPGLYGGGTVVTVNA | II | S1 |
| 149 | ARVDQTPQTITKLTGESLTINCVLRDTYCALSNTNWYHKKSGSTH EESISKGGRYVETLNTDSKSFSLRITDLTIEDSGLYRCKTLSFYV CDLFLWGGDVYGGGTVVTVNA | II | S1 |

TABLE 5

The CDR1, HV2, HV4 and CDR3 sequences for the VNARs from the OSX3 library

| SEQ ID NO: | CDR1 | HV2 | HV4 | CDR3 | CDR3 residue positions |
|---|---|---|---|---|---|
| 1 | DNNCALST | TNEESISKG | SGSKS | VRRVPHNCFPGDVIDWDV | 85-102 |
| 2 | DSNCALSN | TNEESISKG | SGSKS | VMAWFGEECLEDYPDV | 85-100 |
| 3 | DSNCALSS | TNEENISKG | SGSKS | VQTSWRRNCDARVDV | 85-99 |
| 4 | DSNCALSS | TNEENISKG | SGSKS | VVALDPVMGTSCGRAGWDV | 85-103 |
| 5 | DSNCALPS | TNEESISKG | SGSKS | VWQHECAGDYLLGLAGDV | 85-102 |
| 6 | DSNCALPS | TNEENISKG | SGSKS | VLWLVGCHPQGDV | 85-97 |
| 7 | DSNCALPS | TNEESISKG | SGSKS | VESQWTGRENRCVWVIADV | 85-103 |
| 8 | DSNCALSS | TNEENISKG | SGSKS | VVALDPVMRTSCGRAGWDV | 85-103 |
| 9 | DSICALSS | TNEENISKG | SGSKS | VSFYPNSWCWNRQKDV | 85-100 |
| 10 | DSNCALPS | TNEESISKG | SGSKS | VHEIVSAVCGFTQVKDV | 85-101 |
| 11 | DSNCALSS | TNEESISKG | SGSKS | VFAVRPPMMHLCSRGQSDV | 85-103 |

TABLE 5 -continued

The CDR1, HV2, HV4 and CDR3 sequences for the VNARs from the OSX3 library

| SEQ ID NO: | CDR1 | HV2 | HV4 | CDR3 | CDR3 residue positions |
|---|---|---|---|---|---|
| 12 | DASYALGS | TNEENISKG | SGSKS | VLVWSNGTVGMDV | 85-97 |
| 13 | DSNCDLSR | TNEESISKG | SGSKS | VAPGWAGMWGRAACDV | 85-100 |
| 14 | DSNCALPS | TNEESISKG | SGSKS | VSRYVLERHSVCFHSLADV | 85-103 |
| 15 | DSNCALSS | TNEESISKG | SGSKS | VASVDVNPSPQGPVQVV | 85-101 |
| 16 | DSNCALPS | TNEESISKG | SGSKS | VHENLYSHCQFSLPTDV | 85-101 |
| 17 | DNNCALST | TNEESISKG | SGSKS | VFAYYPQYCNVLAQDV | 85-100 |
| 18 | DSNCDLSR | TNEESISKG | SGSKS | VPIFGWVGFCDLTWDDV | 85-101 |
| 19 | DSNCALSN | TNEESISLG | SGSKS | VKLVHAVGGEGCSGALIDV | 85-103 |
| 20 | DSICALSS | TNEARISKG | SGSKS | VQVHPQAACGQHLDV | 85-99 |
| 21 | DSNCALSS | TNEESISKG | SGSKS | VFQYCEEDCWGIWEWDV | 85-101 |
| 22 | DSNCALPS | TNEESISKG | SGSKS | VEGFLGSCDSMWWDDV | 85-100 |
| 23 | DSICALSS | TNEARISKG | SGSKS | VQVHPQAACGQQLDV | 85-99 |
| 24 | DSICALSS | TNEESISKG | SGSKS | VVSDCGYSTYDV | 85-96 |
| 25 | DSICALSS | TNEENISKG | SGSKS | VHMEDMNVRDYGGFWGEDV | 85-103 |
| 26 | DSICALSS | TNEESISKG | SGSKS | VSRGLPGGGAEWCDV | 85-100 |
| 27 | DSNCALSS | RNEESISKG | SGSKS | VNVHVDYYSYCTGFDVDV | 85-102 |
| 28 | DSNCALSN | TNEESISLG | SGSKS | VQNVFWNVCQFHRERDV | 85-101 |
| 29 | DSNCDLSR | TNEESISKG | SGSKS | VWREPRVCRAALSNGLDV | 85-102 |
| 30 | DSNCELSS | TNEARISKG | SGSKS | VLAVVESDGSFMSEDV | 85-100 |
| 31 | DSNCALSN | TNEESISLG | SGSKS | VPLSFCPWHFDV | 85-96 |
| 32 | DSNCALSS | TNEESISKG | SGSKS | VRFNCYDHCGDV | 85-96 |
| 33 | DSNCALSS | TNEESISKG | SGSKS | VFVHDVNVNPGCHPGDV | 85-101 |
| 34 | DSNCALSS | TNEESISLG | SGSKS | VRSALGLDGYACWVDV | 85-100 |
| 35 | DSNCALSS | TNEENISKG | SGSKS | VATIDSLGLGCGMWQGYDV | 85-103 |
| 36 | DNNCALST | TNEENISKG | SGSKS | VSCTFVGYGMLEDV | 85-98 |
| 37 | DSNCALPS | TNEESISKG | SGSKS | VRLESDGWDGAWGWEDV | 85-101 |
| 38 | DSICALSS | TNEESISKG | SGSKS | VFTTLNDICHWMWSKDV | 85-101 |
| 39 | DSNCALSS | RNEARISKG | SGSKS | VLCVQSLRCEFTSEDV | 85-100 |
| 40 | DSNCALSS | TNEESISKG | SGSKS | VLLMDNYGALRDV | 85-97 |
| 41 | DSNCALSS | TNEESISKG | SGSKS | VGSYYILNGGAWRSRADV | 85-102 |
| 42 | DSNCALPS | TNEESISKG | SGSKS | VRRLPHLCQVETIVWDVS | 85-102 |
| 43 | DSNCDLSR | TNEESISKG | SGSKS | VWQIDDYGHRADV | 85-97 |
| 44 | DSNCALSN | TNEESISLG | SGSKS | VRTVPLWNDCDVFEDV | 85-100 |
| 45 | DSNCALPS | TNEESISKG | SGSKS | VVSLFSQGSSFFWDV | 85-99 |
| 46 | DSICALSS | TNEESISKG | SGSKS | VNLRSVLPCGWPDV | 85-98 |
| 47 | DSNCALSS | TNEESISKG | SGSKS | VFQHLALGYDAMCHVGDV | 85-102 |
| 48 | DSICALSS | TNEESISKG | SGSKS | VLEVFCFYGNQGTDV | 85-99 |

TABLE 5 -continued

The CDR1, HV2, HV4 and CDR3 sequences for the VNARs from the OSX3 library

| SEQ ID NO: | CDR1 | HV2 | HV4 | CDR3 | CDR3 residue positions |
|---|---|---|---|---|---|
| 49 | DSNCALSS | TNEESISKG | SGSKS | VWDLISMECWWADV | 85-98 |
| 50 | DSNCALSS | TNEESISKG | SGSKS | VTVLPHVCPDMEPLFVDV | 85-102 |
| 51 | DSNCALSN | TNEESISLG | SGSKS | VQFIDYNCGWDV | 85-96 |
| 52 | DSNCDLSR | TNEESISKG | SGSKS | VISALSWFNDSYQACWVDV | 85-103 |
| 53 | DSICALSS | TNEESISKG | SGSKS | VQTSWRRVCDVGMDV | 85-99 |
| 54 | DSICALSS | TNEESISKG | SGSKS | VGPKVCFRFYGDRSGFDDV | 85-103 |
| 55 | DSNCALSS | TNEESISKG | SGSKS | VLLQDGYGALNDV | 85-97 |
| 56 | DSNCELSS | TNEARISKG | SGSKS | VGSLWVKSGGDSWGRRDDV | 85-103 |
| 57 | DSNCALSN | TNEESISKG | SGSKS | VRRLGCDLDQMFKSWDV | 85-101 |
| 58 | DSNCALSS | TNEESISKG | SGSKS | VEGFLGSCDSMWWDDV | 85-100 |
| 59 | DSNCALSN | TNEESISLG | SGSKS | VSVLCLDYYFLGLKLDV | 85-101 |
| 60 | DSNCALSS | RNEESISKG | SGSKS | VNELFGSDGNVASDV | 85-99 |
| 61 | DSICALSS | TNEESISKG | SGSKS | VENLPGSGSCLRYYLSDV | 85-102 |
| 62 | DSNCALSS | TNEESISKG | SGSKS | VVAQGQLGAIMDV | 85-97 |
| 63 | DSNCALSS | TNEESISKG | SGSKS | VATSWGGDYSQRYVGSDV | 85-102 |
| 64 | DSICALSS | TNEESISKG | SGSKS | VIETFPTYGCLGHDV | 85-99 |
| 65 | DSNCALSS | TNEENISKG | SGSKS | VFAGLPGFCKVLEEDV | 85-100 |
| 66 | DSNCALPS | TNEESISKG | SGSKS | VWCNADKGDSKVCCLRDV | 85-102 |
| 67 | DSNCALSS | TNEESISKG | SGSKS | VFCGNYCCLRDV | 85-96 |
| 68 | DSNCALPS | TNEESISKG | SGSKS | VREWACEDDGRVWGWEDV | 85-102 |
| 69 | DSICALSS | TNEESISKG | SGSKS | VSGWSGYGCLLRDV | 85-98 |
| 70 | DSNCALSS | TNEESISKG | SGSKS | VYTLWDYCTSADSLAGDV | 85-102 |
| 71 | DSNCALPS | TNEESISKG | SGSKS | VKEMHVDRVRVLCGDAELDV | 85-104 |
| 72 | DSICALSS | RNEESISKG | SGSKS | VGDPFGRYGCLSSDV | 85-99 |
| 73 | DSICALSS | TNEESISKG | SGSKS | VSGWGGFGCLRVDV | 85-98 |
| 74 | DSNCALSS | TNEESISKG | SGSKS | VWSHDPYGGACFPPGSRDV | 85-103 |
| 75 | DSNCALSS | TNEESISKG | SGSKS | VKAMDWYYGHWCGDV | 85-99 |
| 76 | DSNCALSN | TNEESISLG | SGSKS | VVSRFYGLCANDRFDV | 85-100 |
| 77 | DSNCALSS | TNEESISKG | SGSKS | VRMEYEGAGPSGGWVDV | 85-101 |
| 78 | DSNCALSN | TNEESISLG | SGSKS | VRCISSLCSYWMGDV | 85-99 |
| 79 | DSICALSS | TNEESISKG | SGSKS | VASTHNACIQLTMRSRDV | 85-102 |
| 80 | DSNCALSS | TNEESISKG | SGSKS | VRSLVSFDGYACWADV | 85-100 |
| 81 | DSNCALSS | TNEESISKG | SGSKS | VWRHECAYDYSGPGCHDV | 85-102 |
| 82 | DSNCALSN | TNEESISLG | SGSKS | VFCTTRLSCYAMFVDV | 85-100 |
| 83 | DSNCALSS | TNEESISKG | SGSKS | VFLHVARSGMMCMDQLGDV | 85-103 |
| 84 | DSNCALSS | TNEESISKG | SGSKS | VLSLDAKYGGFCWIEGADV | 85-103 |
| 85 | DSNCDLSR | TNEESISKG | SGSKS | VFVLNLEYGTICGSSSGDV | 85-103 |

TABLE 5 -continued

The CDR1, HV2, HV4 and CDR3 sequences for the VNARs from the OSX3 library

| SEQ ID NO: | CDR1 | HV2 | HV4 | CDR3 | CDR3 residue positions |
|---|---|---|---|---|---|
| 86 | DSNCALSN | TNEESISLG | SGSKS | VKPIEMKWGYGCGGRHWDV | 85-103 |
| 87 | DSNCALSS | TNEENISKG | SGSKS | VFSHEDGNWCGGGDRARDV | 85-103 |
| 88 | DSNCALSS | TNEESISLG | SGSKS | VISRFYGICQLGADV | 85-99 |
| 89 | DSICALSS | TNEESISKG | SGSKS | VTQFDCANGYLSAVEADV | 85-102 |
| 90 | DSNCALPS | TNEESISKG | SGSKS | VYGRDGYCVMADV | 85-97 |
| 91 | DSNCALSS | TNEESISKG | SGSKS | VWGADDYGSGSDV | 85-97 |
| 92 | DSNCELSS | TNEESISKG | SGSKS | VLAQDVDYGGLSDV | 85-98 |
| 93 | DSNCALPS | TNEESISKG | SGSKS | VFNHATGLCQLWDV | 85-98 |
| 94 | DSICALSS | TNEESISKG | SGSKS | VVGLYRSVCLSATGADV | 85-101 |
| 95 | DSNCALHS | TNEESISKG | SGSKS | VIARYYGLCDLDDV | 85-98 |
| 96 | DSNCALPS | TNEESISKG | SGSKS | VFCSAGLGCYAQFASDV | 85-101 |
| 97 | DSICALSS | TNEESISLG | SGSKS | VRQLLCGGGPGSDV | 85-98 |
| 98 | DSNCDLSR | TNEESISKG | SGSKS | VIGYVANDDYGLRVIDDV | 85-102 |
| 99 | DSICALSS | TNEESISKG | SGSKS | VLLYGLFPCSSVDV | 85-98 |
| 100 | DSNCALSN | TNEESISLG | SGSKS | VRRLSHMCLTVSGLSWDV | 85-102 |

Sequences in Table 5 are residues of the SEQ ID NO in the left column as follows: CDR1 is residues 26-33, HV2 is residues 44-52, HV4 is residues 61-65, and CDR3 is the residues listed in the far-right column.

TABLE 6

The CDR1, HV2, HV4 and CDR3 sequences for the VNARs from the OSX6 library

| SEQ ID NO: | CDR1 | HV2 | HV4 | CDR3 | CDR3 residue positions |
|---|---|---|---|---|---|
| 101 | DSNCPLSN | TNEERLSND | SASNS | ARMYYCDLGHWAPDL | 85-99 |
| 102 | DNICTASN | ENEESISKG | SGSKS | AIFQSGCGVYHRYTGV | 85-100 |
| 103 | NSICALSS | INEEEISKG | SESKS | IVRQSGCEVATFKADV | 85-100 |
| 104 | DSVCALSS | TNEESISKG | SGSKS | SEFKSGCGVFYELTDV | 85-100 |
| 105 | DSICALSS | TNEESISKG | SGSKS | VARTSGCEVYTYTGDV | 85-100 |
| 106 | DSICALSS | RKEESISKG | SGSKS | VARTSGCEVYTYTGDV | 85-100 |
| 107 | YSDCPLSS | TNEERIRNE | SGSKS | YGSIDVCYLTNNERDV | 85-100 |
| 108 | DSICALSS | TNEESISKG | SGSKS | IVRQSGCWVSLHEEDV | 85-100 |
| 109 | DTYCALSN | THEESISKG | TDSKS | TWPVSVCYLTNNERDL | 85-100 |
| 110 | DSRCRLSS | TNEESISKG | SGSKS | HRTPYVCGLHSQHPDL | 85-100 |
| 111 | DSNCALSS | TNEESISKG | SGSKS | IRVVDVCWLEHGTWDV | 85-100 |
| 112 | DAHCALDR | TIEESIPIH | SGGKS | IKSFSDCDLGHWAPDL | 85-100 |
| 113 | DSNCALSS | LNEESISKG | SGSKS | VFRGYDCDVMDVFGGV | 85-100 |
| 114 | DSNCVLGS | TNLESIFSG | SGSKS | IFVNYDCEDAKYWQGL | 85-100 |
| 115 | DSVCALSS | TNEESISKG | SGSKS | VKNPSGCGVWYSQEDL | 85-100 |

TABLE 6-continued

The CDR1, HV2, HV4 and CDR3 sequences for the VNARs from the OSX6 library

| SEQ ID NO: | CDR1 | HV2 | HV4 | CDR3 | CDR3 residue positions |
|---|---|---|---|---|---|
| 116 | DRDCALSS | TNEESISKG | SGSKS | AIILYGCELTSDWSDL | 85-100 |
| 117 | DSNCALSS | TNEEGISKG | SGSKS | LRTHSDCEDNFVEWGL | 85-100 |
| 118 | DSDCALSS | TNEESISKG | SGSKS | TWTLYDCDYRWGNQDL | 85-100 |
| 119 | DSICALSS | TNEESISKG | SGSKS | SEFKSGCGVFYELTDV | 85-100 |
| 120 | DSNCALSS | TFEESISKG | SGSKS | GKVFYDCELYWGMTDV | 85-100 |
| 121 | DSICALSS | TNEESISKG | SGSKS | IVRQSGCEVHLYQRDL | 85-100 |
| 122 | DSNCAVSS | TNEESISKG | SGSKS | INLAYYCYLNFEFRDV | 85-100 |
| 123 | DAHCALDR | TIEESIPIH | SGGKS | MKRFSDCELGLFIEDV | 85-100 |
| 124 | DTYCALSN | THEESISKG | TDSKS | LHMIGDCELPQNWEDL | 85-100 |
| 125 | DSNCALSS | TNEESISKG | SGSKS | LQLWDVCGDNWERIGV | 85-100 |
| 126 | DNICTASN | ENEESISKG | SGSKS | SQSVSGCGVWANEFDV | 85-100 |
| 127 | DTYCALSN | THEESISKG | TDSKS | VARTSGCYVWAWDNDV | 85-100 |
| 128 | DSNCALSS | TNEESISKG | SGSKS | YWPNYYCELDFGERDL | 85-100 |
| 129 | DSNCALSS | TNEEGISKG | SGSKS | MNVWYDCGDKGPERGL | 85-100 |
| 130 | DSVCALSS | TNEESISKG | AGTKS | IVRQSGCWVYWYETGV | 85-100 |
| 131 | DSNCALSS | TNEEGISKG | SGSKS | YYPQDYCDYFGNYRDL | 85-100 |
| 132 | DSNCALSS | TNEENILTG | RGSKS | MVFKSVCEDNPYQYGL | 85-100 |
| 133 | NSICALSS | INEEEISKG | SESKS | IVRQSGCWVTTSEVDL | 85-100 |
| 134 | NSFCRLST | TVEETISKG | RGSKS | IEYLGYCGLWNKFYGL | 85-100 |
| 135 | DSICALSS | TNEESISKG | SGSKS | IWAHSGCEVITHAMDL | 85-100 |
| 136 | DSNCALSS | TNEEGISKG | SGSKS | TLYWSYCDLRTGIHDL | 85-100 |
| 137 | DSHCALSS | TNEESISKG | SGSKS | WVGRLYCGDNEWMQDL | 85-100 |
| 138 | DSNCALWS | TNEESISKG | SGSKS | MREPLDCGLPNWMYGL | 85-100 |
| 139 | DSNCALSS | SYEESISKG | SGSKS | TRRIDVCEVKYEFGDV | 85-100 |
| 140 | DTNCALPG | TNEESISKG | SGSKS | VARTSGCWVYWYETGV | 85-100 |
| 141 | DSNCALSS | SYEESISKG | SGSKS | NRQMDVCWLEHGTWDV | 85-100 |
| 142 | DSNCPLAA | TNEESISKG | SGSKS | IRSTDVCYDAMQETGL | 85-100 |
| 143 | DTYCALSN | THEESISKG | TDSKS | AKGWGDCYYKWTVNDV | 85-100 |
| 144 | GANCAFDR | TREESISKG | SGSKS | KRWISGCDVPVLAPDL | 85-100 |
| 145 | DSNCALSS | THEESISKG | SGSKS | IRQVLDCGYFTGDWDL | 85-100 |
| 146 | DSNCDLST | TNEESISKG | SGSKS | KYEFGDCDLTNKWMDV | 85-100 |
| 147 | DSNCAESS | TNEESISKG | SGSKS | AWEGSWCWVQFLQPGL | 85-100 |
| 148 | DSQCPVEE | TNEERISKR | SGGKS | TDFGGVCWDIWHPPGL | 85-100 |
| 149 | DTYCALSN | THEESISKG | TDSKS | TLSFYVCDLFLWGGDV | 85-100 |

Sequences in Table 6 are residues of the SEQ ID NO in the left column as follows: CDR1 is residues 26-33, HV2 is residues 44-52, HV4 is residues 61-65, and CDR3 is the residues listed in the far-right column.

For Table 5 and Table 6 above, the amino acid sequence for CDR1 is found at amino acids 26-33 of the indicated SEQ ID NO. for that domain; for HV2 at amino acids 44-52; for HV4 sequence at amino acids 61-65; and for CDR3 sequence, it begins at amino acid 85 and continues the length of the particular CDR3 (typically 11-20 amino acids, as shown).

Example 3. Binding Activity of VNAR-hFc Fusions (VNAR Antibodies)

VNAR-Fc formatting. The VNAR clones that showed specific binding to the antigen in phage ELISAs from Example 2 were identified by Sanger sequencing and cloned into the pFUSE expression vector containing the IgG1 human Fc (hFc) domain to produce VNAR human Fc fusions (VNAR-hFc). The final constructs are bivalent antibodies with the VNAR domain fused to the N-terminus of the hFc domain; these fusions are also referred to herein interchangeably as VNAR antibodies.

Expi293 cells were transiently transfected with a VNAR-hFc following the manufacturer protocol at small scale (0.5 ml). Crude supernatants were tested for binding to S1 and S1-RBD proteins by ELISA. Binding to either S1 or S1-RBD was confirmed for a total of 57 VNAR antibodies (Table 7). This data is also shown graphically in FIGS. 3-6 in which

Figure 3:
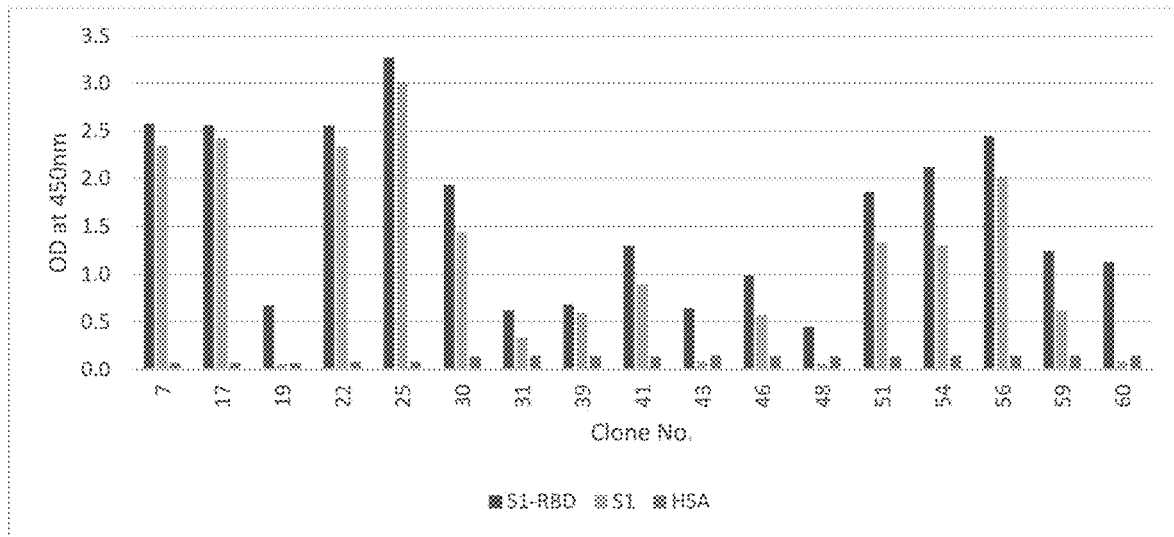
FIG. 3. VNAR Binding to Spike Protein Domains. The bar graph depicts antigen binding of VNAR clones isolated from the OSX3 phage library by selection against recombinant S1-RBD protein and reformatted as VNAR-hFc fusions (VNAR antibodies). VNAR antibody binding was determined by ELISA against (a) S1-RBD, (b) S1 and (c) human serum albumin (HSA) as a control, from left to right, respectively. Only clones that showed binding to either S1-RBD or S1 at an OD>0.3 (~3 fold over blank) are presented on the graph.
Figure 4:
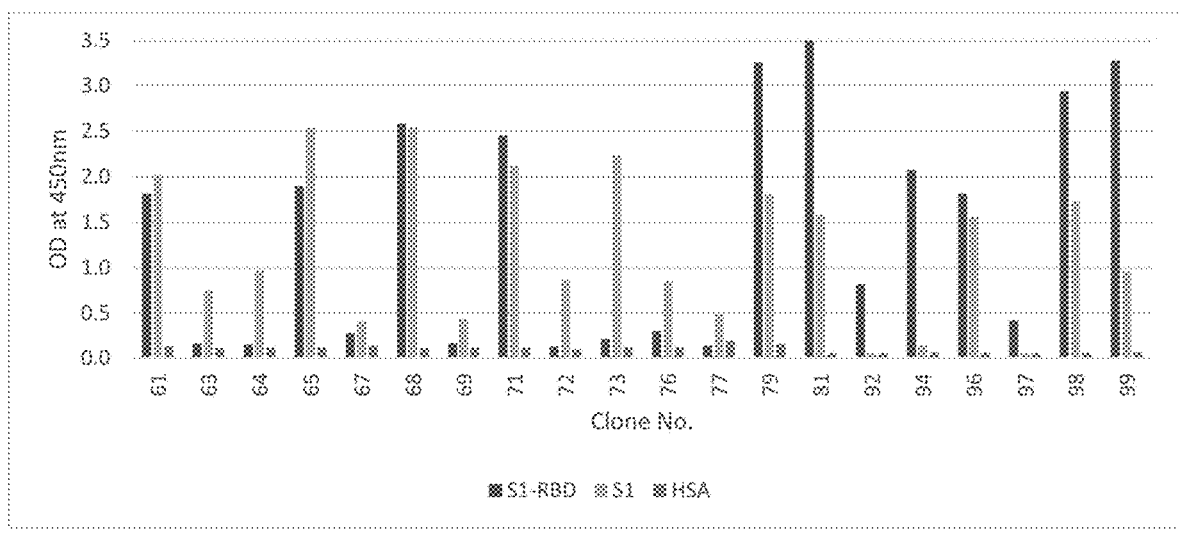
FIG. 4. VNAR Binding to Spike Protein Domains. The bar graph depicts antigen binding of VNAR clones isolated from the OSX3 phage library by selection against recombinant S1 protein and reformatted as VNAR-hFc fusions (VNAR antibodies). VNAR antibody binding was determined by ELISA against (a) S1-RBD, (b) S1 and (c) human serum albumin (HSA) as a control, from left to right, respectively. Only clones that showed binding to either S1-RBD or S1 at an OD>0.3 (~3 fold over blank) are presented on the graph.
Figure 5:
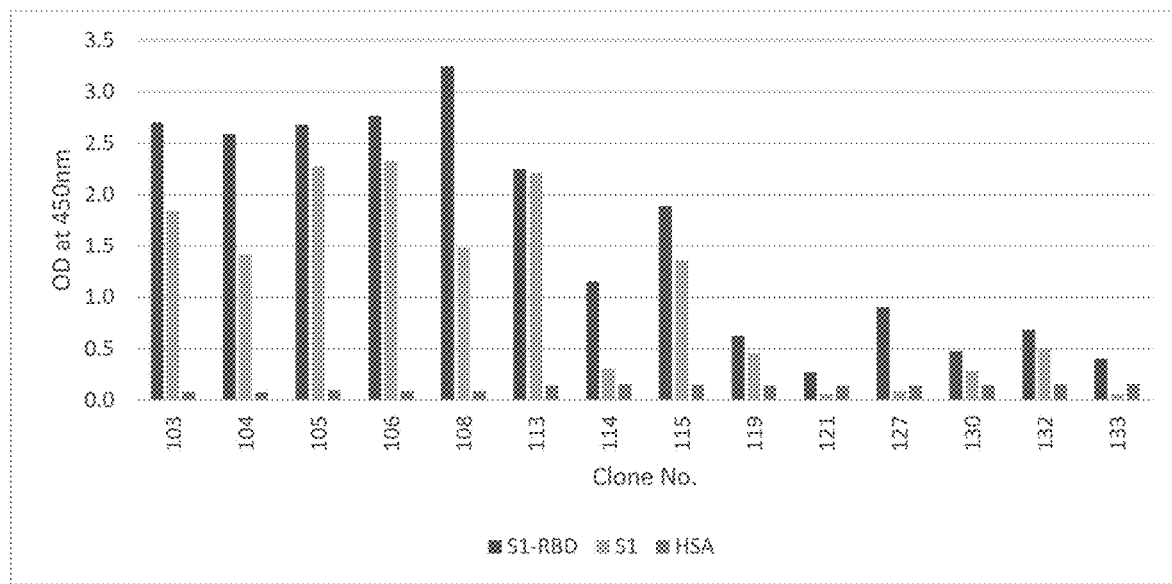
FIG. 5. VNAR Binding to Spike Protein Domains. The bar graph depicts antigen binding of VNAR clones isolated from the OSX6 phage library by selection against recombinant S1-RBD protein and reformatted as VNAR-hFc fusions (VNAR antibodies). VNAR antibody binding was determined by ELISA against (a) S1-RBD, (b) S1 and (c) human serum albumin (HSA) as a control, from left to right, respectively. Only clones that showed binding to either S1-RBD or S1 at an OD>0.3 (~3 fold over blank) are presented on the graph.
Figure 6:
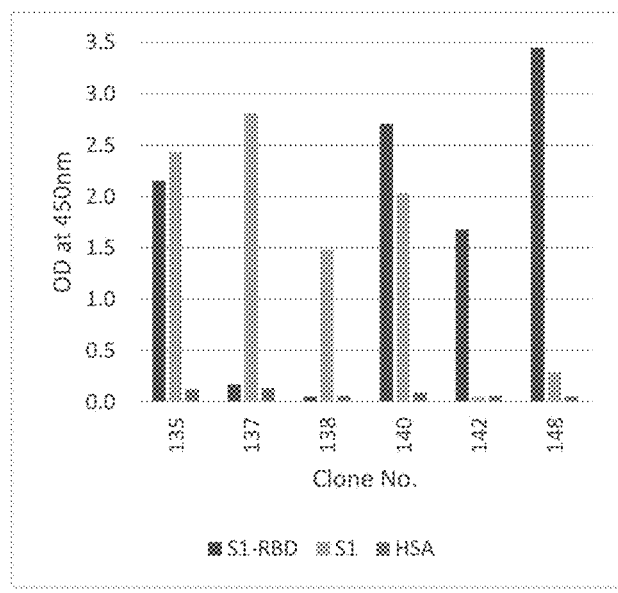
FIG. 6. VNAR Binding to Spike Protein Domains. The bar graph depicts antigen binding of VNAR clones isolated from the OSX6 phage library by selection against recombinant S1 protein and reformatted as VNAR-hFc fusions (VNAR antibodies). VNAR antibody binding was determined by ELISA against (a) S1-RBD, (b) S1 and (c) human serum albumin (HSA) as a control, from left to right, respectively. Only clones that showed binding to either S1-RBD or S1 at an OD>0.3 (~3 fold over blank) are presented on the graph.

- FIG. 3 shows antigen binding of VNAR antibodies selected against S1-RBD isolated from the OSX3 phage library;
- FIG. 4 shows antigen binding of VNAR antibodies selected against S1 protein isolated from the OSX3 phage library;
- FIG. 5 shows antigen binding of VNAR antibodies selected against S1-RBD isolated from the OSX6 phage library; and
- FIG. 6 shows antigen binding of VNAR antibodies selected against S1 protein isolated from the OSX6 phage library.

Only clones that showed binding by ELISA to either S1-RBD or S1 are presented on the bar graphs, measured as OD>0.3 (or about 3-fold over blank). The OD450 values are listed in Table 7 and those OD values>0.3 are in bolded.

The larger OSX3 library produced 37 VNAR antibodies (with 17 from the S1-RBD and 20 from the S1 selection), whereas 20 antibodies came from OSX6 library (with 14 from the S1-RBD and 6 from the S1 selection).

The VNAR antibodies that specifically bound to either S1 or S1-RBD were expressed at a larger scale (50 ml) and purified to measure their binding potency by ELISA. For larger scale production, after 5 days growth, the transiently-transfected cell cultures were centrifuged at 2,000 rpm for 10 min, supernatants were filtered using 0.22 μm membrane filters and loaded onto HiTrap MabSelect SuRe columns (Cytiva) pre-equilibrated against PBS, pH 7.4. Protein A-bound antibodies were eluted with 0.1 M glycine, pH 3.5 and the buffer exchanged to PBS, pH 7.4 using HiPrep 26/10 desalting column (Cytiva). Purity of the purified protein samples was determined by analytical SEC and SDS-PAGE.

To determine the binding $EC_{50}$ of the selected VNAR antibodies, high binding 96 well microplates (Greiner) were coated overnight at 4° C. with 100 μl of S1, S1-RBD or HSA at 5 μg/ml or S1-RBD E484K or S1-RBD N501Y at 1 μg/ml. Plates were blocked for 1 hr at RT with 5% bovine serum albumin (BSA) in PBS before a 1 hr incubation with serially diluted VNAR-hFc antibodies or ACE2. The plates were washed, and binding was detected with an anti-human IgG (Fc specific) (1:5000 dilution, Sigma-Aldrich, A0170) or anti-FLAG (1:1000 dilution, Sigma-Aldrich, A8592) HRP-conjugated antibodies for VNAR-hFc antibodies or ACE2, respectively. The signal was developed with 1-Step™ Ultra TMB-ELISA substrate solution (Thermo Fisher Scientific) and the reaction was stopped with 1% HCl. Absorbance measured at 450 nm and $EC_{50}$ values were calculated by 4-parametric non-linear regression using GraphPad Prism 8.0.

Figure 2:
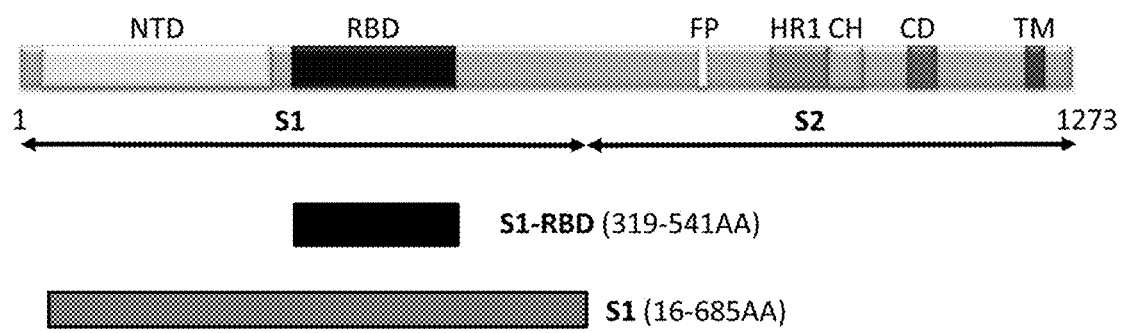
FIG. 2. Schematic representation of SARS-CoV-2 spike protein and its domains. The S1 and S2 fragments are indicated. Protein domains illustrated are: N-terminal domain (NTD), receptor-binding domain (RBD), fusion peptide (FP), heptad repeat 1 (HR1), central helix (CH), connector domain (CD), and transmembrane domain (TM). The S1-RBD recombinant protein contains only the RBD domain, whereas the S1 recombinant protein contains both the NTD and RBD domains.
Figure 7:
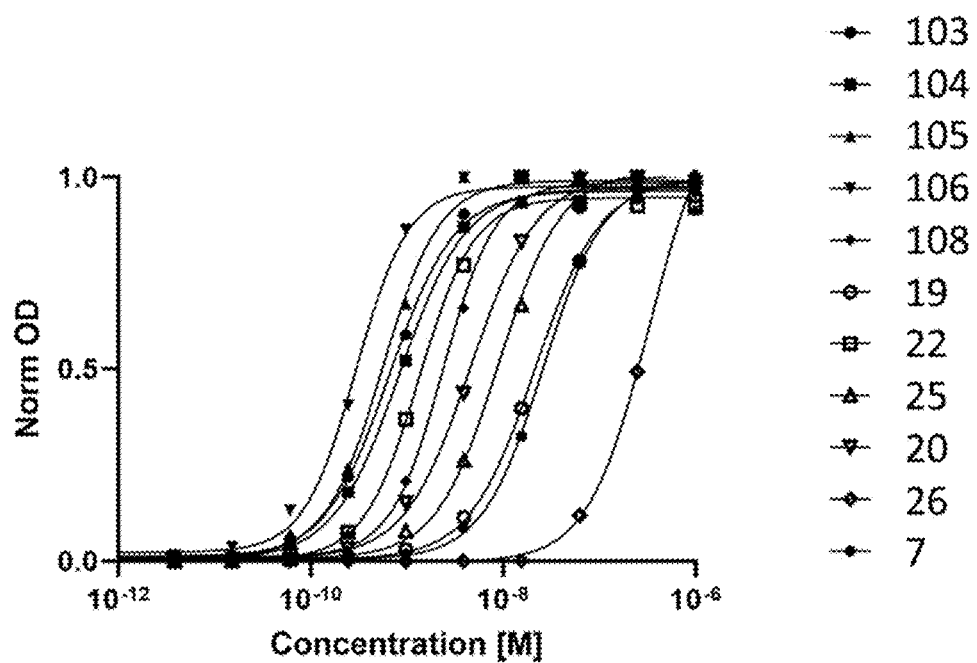
FIG. 7. $EC_{50}$ binding curves of VNAR antibodies to S1-RBD for VNARs selected against S1-RBD. Binding was assessed by ELISA with serial dilutions of diluted VNAR antibody and immobilized recombinant S1-RBD protein. For the simplicity, the binding curves for eleven VNAR antibodies are shown (VNAR antibodies 7, 19, 20, 22, 25, 26, 103, 104, 105, 106, and 108). Calculated $EC_{50}$ values for all tested VNAR antibodies are presented in Table 8.
Figure 8:
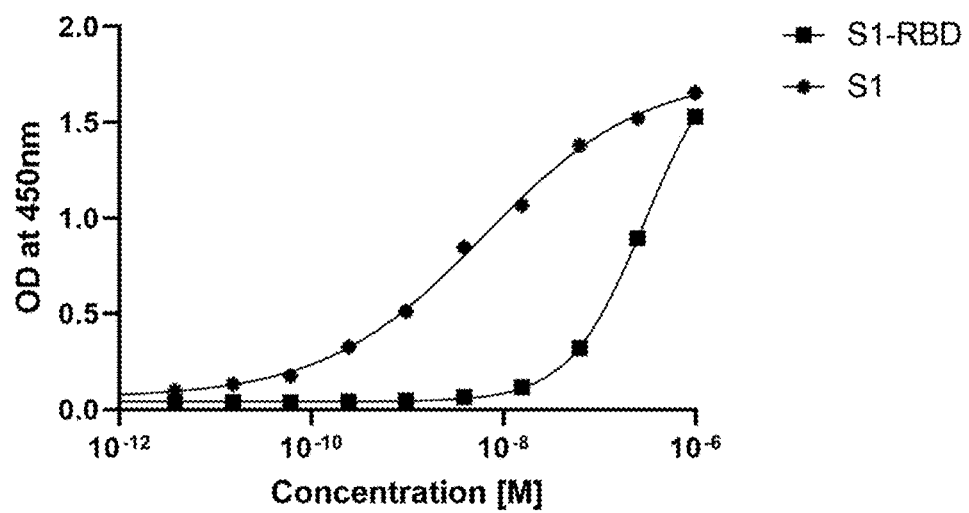
FIG. 8. $EC_{50}$ binding curves of VNAR antibody 137 to recombinant S1-RBD and S1. Binding was assessed by ELISA with serially-diluted VNAR antibody and immobilized recombinant S1-RBD or S1 proteins. VNAR antibody 137 is an example of a specific binder to the NTD domain present in the S1 construct which does not bind RBD domain. Its calculated $EC_{50}$ value is provided in Table 9.

The $EC_{50}$ values were determined for thirty VNAR antibodies (16 from OSX3 and 14 from OSX6) and showed a binding potency for S1-RBD in the low nM range (Table 8; FIG. 7). None of the clones selected against S1-RBD regardless of library origin showed a binding $EC_{50}$>3E-08 M (Table 8). In addition, eleven VNAR antibodies (9 from OSX3 and 2 from OSX6) selected against S1 were assessed. Of those, six VNAR antibodies (4 from OSX3 and 2 from OSX6) bound to either S1 or S1-RBD with high potency (Table 9; FIG. 8). One VNAR antibody (derived from clone 137) may interact with NTD domain since it was specific for S1 but did not bind to the S1-RBD (FIGS. 2 and 8).

TABLE 7

VNAR Antibody Binding to S1-RBD or S1 by ELISA (Values are OD450)

| VNAR Ab | S1-RBD | S1 | HSA | Sel. Antigen | Library |
|---|---|---|---|---|---|
| 7 | 2.6 | 2.4 | 0.1 | S1-RBD | OSX3 |
| 17 | 2.6 | 2.4 | 0.1 | S1-RBD | OSX3 |
| 19 | 0.7 | 0.1 | 0.1 | S1-RBD | OSX3 |
| 22 | 2.6 | 2.3 | 0.1 | S1-RBD | OSX3 |
| 25 | 3.3 | 3.0 | 0.1 | S1-RBD | OSX3 |
| 30 | 1.9 | 1.4 | 0.1 | S1-RBD | OSX3 |
| 31 | 0.6 | 0.3 | 0.2 | S1-RBD | OSX3 |
| 39 | 0.7 | 0.6 | 0.1 | S1-RBD | OSX3 |
| 41 | 1.3 | 0.9 | 0.1 | S1-RBD | OSX3 |
| 43 | 0.6 | 0.1 | 0.2 | S1-RBD | OSX3 |
| 46 | 1.0 | 0.6 | 0.1 | S1-RBD | OSX3 |
| 48 | 0.4 | 0.1 | 0.1 | S1-RBD | OSX3 |
| 51 | 1.9 | 1.3 | 0.1 | S1-RBD | OSX3 |
| 54 | 2.1 | 1.3 | 0.2 | S1-RBD | OSX3 |
| 56 | 2.4 | 2.0 | 0.1 | S1-RBD | OSX3 |
| 59 | 1.2 | 0.6 | 0.2 | S1-RBD | OSX3 |
| 60 | 1.1 | 0.1 | 0.2 | S1-RBD | OSX3 |
| 61 | 1.8 | 2.0 | 0.1 | S1 | OSX3 |
| 63 | 0.2 | 0.8 | 0.1 | S1 | OSX3 |
| 64 | 0.2 | 1.0 | 0.1 | S1 | OSX3 |
| 65 | 1.9 | 2.5 | 0.1 | S1 | OSX3 |
| 67 | 0.3 | 0.4 | 0.1 | S1 | OSX3 |
| 68 | 2.6 | 2.5 | 0.1 | S1 | OSX3 |
| 69 | 0.2 | 0.4 | 0.1 | S1 | OSX3 |
| 71 | 2.5 | 2.1 | 0.1 | S1 | OSX3 |
| 72 | 0.1 | 0.9 | 0.1 | S1 | OSX3 |
| 73 | 0.2 | 2.2 | 0.1 | S1 | OSX3 |
| 76 | 0.3 | 0.9 | 0.1 | S1 | OSX3 |
| 77 | 0.1 | 0.5 | 0.2 | S1 | OSX3 |
| 79 | 3.3 | 1.8 | 0.2 | S1 | OSX3 |
| 81 | 3.7 | 1.6 | 0.1 | S1 | OSX3 |
| 92 | 0.8 | 0.1 | 0.1 | S1 | OSX3 |
| 94 | 2.1 | 0.1 | 0.1 | S1 | OSX3 |
| 96 | 1.8 | 1.6 | 0.1 | S1 | OSX3 |
| 97 | 0.4 | 0.0 | 0.1 | S1 | OSX3 |
| 98 | 2.9 | 1.7 | 0.1 | S1 | OSX3 |
| 99 | 3.3 | 1.0 | 0.1 | S1 | OSX3 |
| 103 | 2.7 | 1.8 | 0.1 | S1-RBD | OSX6 |
| 104 | 2.6 | 1.4 | 0.1 | S1-RBD | OSX6 |
| 105 | 2.7 | 2.3 | 0.1 | S1-RBD | OSX6 |
| 106 | 2.8 | 2.3 | 0.1 | S1-RBD | OSX6 |
| 108 | 3.2 | 1.5 | 0.1 | S1-RBD | OSX6 |
| 113 | 2.2 | 2.2 | 0.1 | S1-RBD | OSX6 |
| 114 | 1.2 | 0.3 | 0.2 | S1-RBD | OSX6 |
| 115 | 1.9 | 1.4 | 0.1 | S1-RBD | OSX6 |
| 119 | 0.6 | 0.5 | 0.1 | S1-RBD | OSX6 |

TABLE 7-continued

VNAR Antibody Binding to S1-RBD or S1 by ELISA
(Values are OD450)

| VNAR Ab | S1-RBD | S1 | HSA | Sel. Antigen | Library |
|---|---|---|---|---|---|
| 121 | 0.3 | 0.1 | 0.1 | S1-RBD | OSX6 |
| 127 | 0.9 | 0.1 | 0.1 | S1-RBD | OSX6 |
| 130 | 0.5 | 0.3 | 0.1 | S1-RBD | OSX6 |
| 132 | 0.7 | 0.5 | 0.2 | S1-RBD | OSX6 |
| 133 | 0.4 | 0.1 | 0.2 | S1-RBD | OSX6 |
| 135 | 2.2 | 2.4 | 0.1 | S1 | OSX6 |
| 137 | 0.2 | 2.8 | 0.1 | S1 | OSX6 |
| 138 | 0.1 | 1.5 | 0.1 | S1 | OSX6 |
| 140 | 2.7 | 2.0 | 0.1 | S1 | OSX6 |
| 142 | 1.7 | 0.1 | 0.1 | S1 | OSX6 |
| 148 | 3.4 | 0.3 | 0.1 | S1 | OSX6 |

TABLE 8

Binding $EC_{50}$ values for VNAR antibodies to
S1-RBD selected against S1-RBD

| VNAR Ab | Sel. Antigen | Library | $EC_{50}$ S1-RBD [M] |
|---|---|---|---|
| 7 | S1-RBD | OSX3 | 2.6E−08 |
| 19 | S1-RBD | OSX3 | 2.1E−08 |
| 22 | S1-RBD | OSX3 | 1.3E−09 |
| 25 | S1-RBD | OSX3 | 9.0E−09 |
| 30 | S1-RBD | OSX3 | 7.0E−10 |
| 31 | S1-RBD | OSX3 | 3.3E−09 |
| 39 | S1-RBD | OSX3 | 1.8E−09 |
| 41 | S1-RBD | OSX3 | 1.9E−09 |
| 43 | S1-RBD | OSX3 | 3.3E−09 |
| 46 | S1-RBD | OSX3 | 1.4E−09 |
| 48 | S1-RBD | OSX3 | 2.9E−09 |
| 51 | S1-RBD | OSX3 | 4.2E−10 |
| 54 | S1-RBD | OSX3 | 8.2E−10 |
| 56 | S1-RBD | OSX3 | 1.1E−09 |
| 59 | S1-RBD | OSX3 | 1.1E−09 |
| 60 | S1-RBD | OSX3 | 2.2E−09 |
| 103 | S1-RBD | OSX6 | 6.6E−10 |
| 104 | S1-RBD | OSX6 | 8.4E−10 |
| 105 | S1-RBD | OSX6 | 5.6E−10 |
| 106 | S1-RBD | OSX6 | 3.0E−10 |
| 108 | S1-RBD | OSX6 | 2.4E−09 |
| 113 | S1-RBD | OSX6 | <1E−09 |
| 114 | S1-RBD | OSX6 | <1E−09 |
| 115 | S1-RBD | OSX6 | <1E−09 |
| 119 | S1-RBD | OSX6 | <1E−09 |
| 121 | S1-RBD | OSX6 | 7.2E−09 |
| 127 | S1-RBD | OSX6 | 3.4E−09 |
| 130 | S1-RBD | OSX6 | 1.2E−09 |
| 132 | S1-RBD | OSX6 | 1.3E−09 |
| 133 | S1-RBD | OSX6 | 3.8E−09 |

TABLE 9

Binding $EC_{50}$ values of VNAR antibodies to
S1-RBD and S1 selected using S1

| VNAR Ab | Sel. Antigen | Library | $EC_{50}$ S1-RBD [M] | $EC_{50}$ S1 [M] |
|---|---|---|---|---|
| 61 | S1 | OSX3 | 3.6E−10 | 7.2E−10 |
| 63 | S1 | OSX3 | >1E−07 | >1E−07 |
| 64 | S1 | OSX3 | >1E−07 | >1E−07 |
| 65 | S1 | OSX3 | 3.2E−09 | 3.3E−09 |
| 68 | S1 | OSX3 | 5.2E−10 | 8.5E−09 |
| 71 | S1 | OSX3 | 9.1E−09 | >1E−07 |
| 72 | S1 | OSX3 | >1E−07 | >1E−07 |
| 73 | S1 | OSX3 | >1E−07 | >1E−07 |
| 76 | S1 | OSX3 | >1E−07 | >1E−07 |
| 135 | S1 | OSX6 | 4.2E−10 | 4.6E−10 |
| 137 | S1 | OSX6 | >1E−07 | 6.3E−09 |

Example 5. Blocking Activity of VNAR Antibodies

VNAR antibodies with a high binding potency to S1-RBD were further tested in a competition assay. The $IC_{50}$ values were determined by ELISA as described in Example 4 except that serial dilutions of the VNAR-hFc fusions were premixed with 1.4 nM of purified ACE2 (see Example 1) prior to incubation on the coated microtiter plates. ACE2 binding was measured with an anti-FLAG HRP conjugated antibody (Sigma-Aldrich, A8592) diluted 1:1000.

Figure 9:
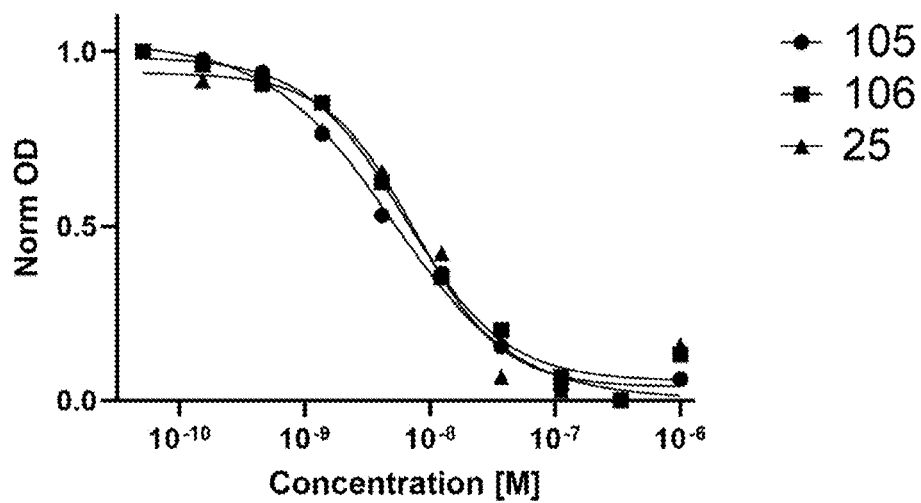
FIG. 9. $IC_{50}$ curves of three VNAR antibodies (25,105 and 106) that block the interaction of S1-RBD with ACE2 protein. ACE2 at a fixed concentration was premixed with serially-diluted VNAR antibodies before incubation with S1-RBD immobilized on ELISA plates, followed by washing. ACE2 binding was detected by anti-FLAG HRP conjugated antibody. Data presented as normalized OD at 450 nm. The calculated $IC_{50}$ values for the tested VNAR antibodies are presented in Table 10.

The $IC_{50}$ values for the twenty VNAR antibodies tested (7 from OSX3 and 13 from OSX6) ranged from 6.40E−07 to 4.98E−09 M (Table 10). FIG. 9 shows the inhibition binding curve of VNAR antibodies 105 (solid circles), 106 (solid squares) and 25 (solid triangles) for ACE2 binding to S1-RBD. The most potent blocking VNAR antibodies from the ELISA-based competition assay were further evaluated in a cell-based blocking assay.

Cell-based blocking was assessed by flow cytometry. Expi293 cells were transiently transfected with ACE2 cloned into the pCMV3-C-GFPSpark expression vector (Sino Biological). Cells were incubated at 37° C. in 8% $CO_2$ shaking at 350 RPM for 48 hr, The collected cells were blocked in 2% BSA in PBS for 30 min at 4° C. and then transferred to a 96-well V-shaped microplate (Greiner) at a density of 100,000 cells per well. S1 protein was biotinylated at the AVI-tag using the BirA biotin-protein ligase kit (Avidity Biosciences) and premixed at 5 nM with serial dilutions of VNAR antibodies for 1 hr at 4° C. Binding of S1 to ACE2 transfected cells was measured with an Alexa Fluor-647-conjugated streptavidin (Invitrogen, S21374) diluted 1:500 using a CytoFLEX flow cytometer (Beckman Coulter). Data presented as normalized median fluorescence intensity (MFI) was used to determine $IC_{50}$ by 4-parametric non-linear regression analysis using GraphPad Prism 8.0.

Figure 10:
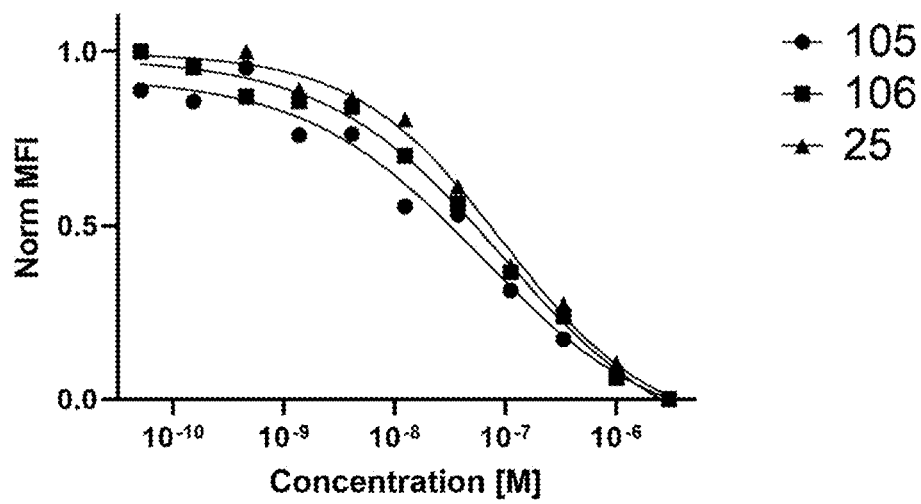
FIG. 10. $IC_{50}$ curves of three VNAR antibodies (25,105 and 106) that block binding of S1 to cells overexpressing ACE2. Expi293 cells transiently expressing ACE2 were used for the assay. S1 was premixed with serially-diluted VNAR antibodies before incubation with the cells. Binding was measured by flow cytometry and the data presented as normalized median fluorescence intensity (MFI) of the transfected cell population. Calculated $IC_{50}$ values for the tested VNAR antibodies are presented in Table 11.

The binding of S1 or S1-RBD to cells transiently transfected with ACE2 showed that a total of fifteen VNAR antibodies (6 from OSX3 and 9 from OSX6) blocked the interaction between S1 or S1-RBD and ACE2 expressed on the cell surface (blocking $IC_{50}$ values in Table 11). FIG. 10 shows the inhibition binding curves of VNAR antibodies 105 (solid circles), 106 (solid squares) and 25 (solid triangles) for S1 on cells which overexpress ACE2.

TABLE 10

ELISA $IC_{50}$ Values of VNAR Antibody
Block of S1-RBD-ACE2 Interactions

| VNAR Ab | $IC_{50}$ [M] | Library |
|---|---|---|
| 22 | 4.33E−07 | OSX3 |
| 25 | 7.52E−09 | OSX3 |
| 39 | 6.55E−08 | OSX3 |
| 46 | 2.22E−08 | OSX3 |
| 54 | 1.07E−07 | OSX3 |
| 61 | <1E−08 | OSX3 |
| 68 | 1.53E−07 | OSX3 |

TABLE 10-continued

ELISA IC$_{50}$ Values of VNAR Antibody Block of S1-RBD-ACE2 Interactions

| VNAR Ab | IC$_{50}$ [M] | Library |
|---|---|---|
| 103 | 1.03E−07 | OSX6 |
| 104 | 1.82E−07 | OSX6 |
| 105 | 4.98E−09 | OSX6 |
| 106 | 6.36E−09 | OSX6 |
| 108 | 6.40E−07 | OSX6 |
| 115 | 7.68E−09 | OSX6 |
| 119 | 1.15E−08 | OSX6 |
| 121 | 2.26E−07 | OSX6 |
| 127 | 8.06E−08 | OSX6 |
| 130 | 4.09E−08 | OSX6 |
| 132 | 1.45E−08 | OSX6 |
| 133 | 1.40E−07 | OSX6 |
| 135 | <1E−08 | OSX6 |

TABLE 11

Cell-based IC$_{50}$ values for VNAR Antibody Block of S1-RBD-ACE2 or S1-ACE2 Interactions

| VNAR Ab | S1-RBD:ACE2 Block IC$_{50}$ [M] | S1:ACE2 Block IC$_{50}$ [M] | Library |
|---|---|---|---|
| 25 | 7.53E−08 | 9.62E−08 | OSX3 |
| 37 | 1.82E−07 | not measured | OSX3 |
| 39 | 2.86E−07 | not measured | OSX3 |
| 46 | 4.63E−07 | 7.75E−08 | OSX3 |
| 61 | 6.15E−07 | 1.89E−07 | OSX3 |
| 68 | 3.18E−07 | 8.32E−07 | OSX3 |
| 103 | 1.86E−07 | not measured | OSX6 |
| 104 | 3.52E−07 | not measured | OSX6 |
| 105 | 1.53E−07 | 5.98E−08 | OSX6 |
| 106 | 1.20E−08 | 9.46E−08 | OSX6 |
| 108 | 2.24E−07 | not measured | OSX6 |
| 115 | 1.77E−07 | 2.16E−07 | OSX6 |
| 119 | 9.95E−07 | 2.84E−07 | OSX6 |
| 132 | 2.16E−06 | 2.13E−07 | OSX6 |
| 135 | 7.92E−08 | 8.69E−08 | OSX6 |

Example 6. Activity of VNAR Antibodies Against Spike Variants

The ten VNAR antibodies (4 from OSX3 and 6 from OSX6) that blocked ACE2 with both S1 and S1-RBD interaction in cell-based assay (Table 11) were tested for binding to three spike protein variants containing mutations in emerging virus variants. These included two S1-RBD recombinant proteins with a single E484K or N501Y mutation as well as a quadruple mutant of S1 protein containing K417N, E484K, N501Y and D614G mutations.

Figure 11:
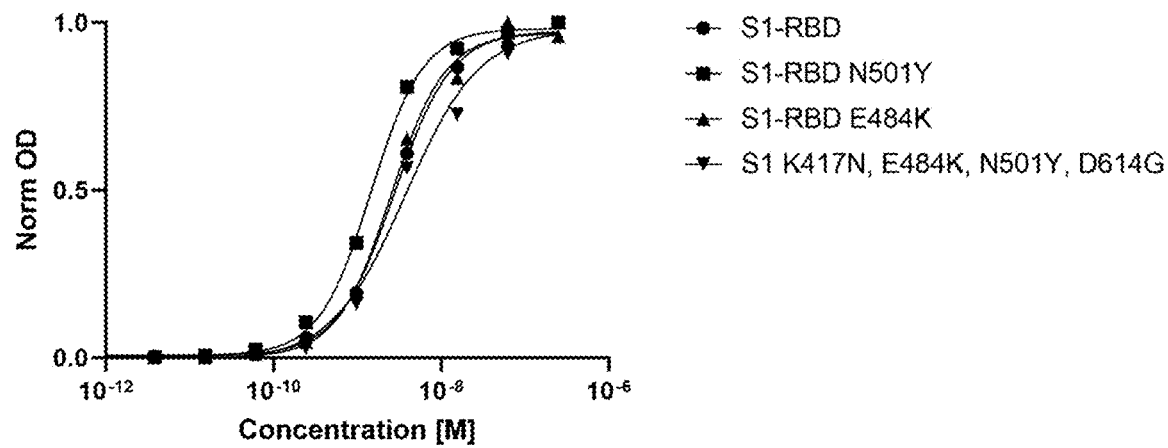
FIG. 11. ECs binding curves of S1 mutants to ACE2. The mutants included S1-RBD recombinant protein with a single E484K or N501Y mutation as well as quadruple mutant of S1 protein containing K417N, E484K, N501Y and D614G mutations. Binding to immobilized S1 mutants with serial dilutions of recombinant ACE2 ectodomain receptor was assessed by ELISA. Calculated $EC_{50}$ values are presented in Table 12.

ACE2 binding to Viral Variants. As shown in FIG. 11, the variants bound to the ACE2 receptor with similar EC$_{50}$ affinity compared to S1-RBD when measured by ELISA as described in Example 4 using immobilized S1 mutants with serially-diluted recombinant ACE2 receptor. Calculated EC$_{50}$ values for the S1 mutants are presented in Table 12.

VNAR antibody binding to Viral Variants. The ten VNAR antibodies were tested in an ELISA as described in Example 4 to determine EC$_{50}$ values using immobilized S1 mutants with serially-diluted VNAR antibodies followed by washes and ACE2 binding detection. Calculated EC$_{50}$ values for the S1 mutants are presented in Table 13.

Figure 12:
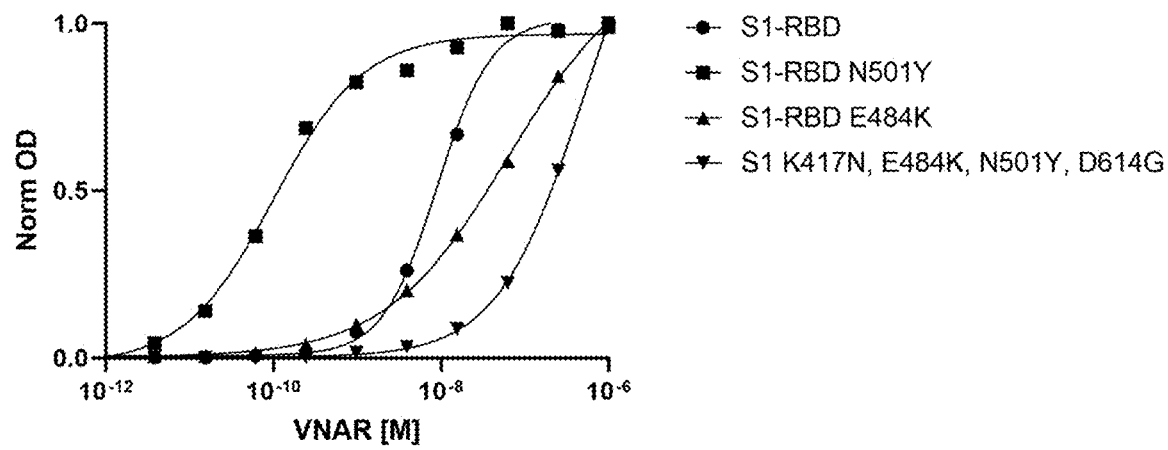
FIG. 12. ECs binding curves of VNAR antibody 25 to spike S1-RBD domain and mutants. Binding was assessed with serially-diluted VNAR antibody on immobilized recombinant spike proteins S1-RBD (circles), S1-RBD N501Y (squares), S1-RBD E484K (upright triangles) and S1 K417N, E484K, N501Y and D614G (inverted triangles).

All the tested VNAR antibodies retained binding to the S1-RBD N501Y mutant with similar EC$_{50}$ values (cf. Table 13) except for the antibody derived from VNAR clone 25 which showed a stronger EC$_{50}$ to S1-RBD N501Y whose binding curves are shown in FIG. 12. EC$_{50}$ binding affinities were reduced for S1-RBD E484K as well as for S1 K417N, E484K, N501Y, D614G in comparison to S1-RBD (Table 13) and as shown for VNAR antibody 25 in FIG. 12. Moreover, all the tested VNAR antibodies inhibited binding of S1-RBD N501Y to ACE2 with similar IC$_{50}$ potency when compared to S1-RBD (Table 14) and as shown for VNAR antibody 25 in FIG. 13. Antibodies derived from clones 25, 68 and 132 were also able to inhibit binding of S1-RBD E484K binding to ACE2 with the same IC$_{50}$. None of the tested VNAR antibodies were able to block binding of ACE2 and the S1 K417N, E484K, N501Y, D614G mutant (Table 14).

TABLE 12

EC$_{50}$ Binding Values of ACE2 to S1 Mutants

| | EC$_{50}$ [M] | | | |
|---|---|---|---|---|
| | S1-RBD | S1-RBD N501Y | S1-RBD E484K | S1 K417N, E484K, N501Y, D614G |
| ACE2 | 2.8E−09 | 1.5E−09 | 2.5E−09 | 3.8E−09 |

TABLE 13

EC$_{50}$ Binding Values of VNAR Antibodies to S1 Mutants

| | EC$_{50}$ [M] | | | |
|---|---|---|---|---|
| VNAR Ab | S1-RBD | S1-RBD N501Y | S1-RBD E484K | S1 K417N, E484K, N501Y, D614G |
| 25 | 8.9E−09 | 1.0E−10 | 6.3E−08 | >1E−06 |
| 46 | 1.4E−09 | 8.0E−09 | 3.2E−08 | 4.1E−08 |
| 61 | 3.2E−10 | 3.0E−10 | >1E−06 | >1E−06 |
| 68 | 4.9E−10 | 3.1E−09 | 3.1E−07 | >1E−06 |
| 105 | 5.5E−10 | 2.7E−10 | 1.6E−07 | 2.3E−07 |
| 106 | 2.9E−10 | 2.9E−10 | 6.4E−08 | 8.4E−08 |
| 115 | 6.0E−10 | 3.2E−09 | >1E−07 | >1E−06 |
| 119 | 5.2E−10 | 9.3E−10 | >1E−06 | >1E−06 |
| 132 | 1.7E−09 | 1.7E−09 | 2.7E−08 | >1E−06 |
| 135 | 3.9E−10 | 3.4E−10 | >1E−06 | >1E−06 |

TABLE 14

IC$_{50}$ Values of VNAR Antibody Blocking of S1 Mutants:ACE2 Interactions

| | IC$_{50}$ [M] | | | |
|---|---|---|---|---|
| VNAR Ab | S1-RBD | S1-RBD N501Y | S1-RBD E484K | S1 K417N, E484K, N501Y, D614G |
| 25 | 7.5E−09 | 2.8E−08 | 6.9E−09 | n.d. |
| 46 | 2.2E−08 | 5.0E−07 | n.d. | n.d. |
| 61 | 8.8E−09 | 4.4E−10 | n.d. | n.d. |
| 68 | 9.2E−08 | 2.3E−07 | 1E−08* | n.d. |
| 105 | 5.0E−09 | 6.5E−09 | n.d. | n.d. |
| 106 | 6.4E−09 | 6.9E−09 | n.d. | n.d. |
| 115 | 7.7E−09 | 2.7E−08 | n.d. | n.d. |
| 119 | 1.2E−08 | 1.5E−08 | n.d. | n.d. |
| 132 | 1.5E−09 | 9.9E−09 | 1.5E−08 | n.d. |
| 135 | 6.1E−09 | 1.2E−08 | n.d. | n.d. |

*approximated value due to poor fit to non-linear regression model;
n.d., not determined.

Example 7. Viral Neutralization by VNAR Antibodies

VNAR antibodies 25, 46, 61, 68, 105, 106, 115, 119, 132 and 135 which blocked ACE2 interaction with both the S1 and S1-RBD in cell-based assay were tested for viral blocking using the live SARS-CoV-2 Wuhan strain as described below. All studies with live virus were conducted in a certified BSL3 laboratory.

Vero CCL81 cells were seeded at a cell density of 100,000 cells per well in 48-well plates and incubated at 370 in serum free OptiPro SFM medium (Thermo Fisher Scientific) for 24 hr before infection. The SARS-CoV-2 Wuhan strain propagated in Vero CCL81 cells was preincubated with or without VNAR antibody for 10 min in OptiPro medium before incubation of the mix with prewashed Vero CCL81 cells for 1 hr at 37° C. Supernatants were transferred to Eppendorf tubes and inactivated with 560 µl of AVL buffer from QIAamp Viral RNA Mini Kit (Qiagen). The cells were washed and further incubated at 37° C. for 48 hr before supernatant was again harvested and the virus inactivated in AVL buffer. Cell death was assessed by phase microscopy at the end of the experiment.

Viral RNA was isolated from inactivated viral supernatants using the QIAamp Kit according to manufacturer's protocol. Briefly, 560 µl absolute ethanol was added and loaded onto columns. After washes with AW1 and AW2 buffers, RNA was collected using 40 µl of Ambion nuclease free water (Thermo Fisher Scientific). Total RNA (5 µl) was used for cDNA synthesis and qPCR was performed in one step using QuantiTect Probe RT-PCR (Qiagen) on a StepOnePlus System (Applied Biosystems). The qPCR primers (synthesized by Eurofins, Luxembourg) were as follows: N1 forward GAC CCC AAA ATC AGC GAA AT (SEQ ID NO. 171), N1 reverse TCT GGT TAC TGC CAG TTG AAT CTG (SEQ ID NO. 172), and N1 Probe FAM-ACC CCG CAT TAC GTT TGG TGG ACC-BHQ1 (SEQ ID NO. 173). To assess RNA quality, RNase P Primers were used: RP Forward AGA TTT GGA CCT GCG AGC G (SEQ ID NO. 174), RP Reverse GAG CGG CTG TCT CCA CAA GT (SEQ ID NO. 175), and RP Probe FAM—TTC TGA CCT GAA GGC TCT GCG CG-BHQ-1 (SEQ ID NO. 176). FAM is a dye label and BHQ1 is a quencher.

The qPCR primers were used at 0.4 µM with the probe at 0.2 µM and samples were incubated at 50° C. for 30 minutes, heated to 95° C. for 15 min, followed by 45 cycles of 95° C. for 3 seconds and 55° C. for 30 seconds. $C_t$ values obtained after 48 hr were subtracted from $C_t$ values at the time of infection and the data normalized between cells that were neither exposed to the virus nor treated with the antibodies set to 0% and untreated cells exposed to the virus set to 100%.

The assay was performed qualitatively using 5 µg/mL (65 nM), 10 µg/mL (130 nM) and 50 µg/mL (650 nM) of VNAR antibody. The ten S1-RBD binding VNAR antibodies were all able to prevent viral infection at 5 µg/mL (FIG. 14). Notably, the S1-NTD specific VNAR antibody 137 did not show any significant blocking activity until 50 µg/mL (FIG. 15). Hence, screening and selection of VNAR clones and VNAR antibodies against the S1-RBD domain using in vitro and cell-based assays can accurately predict inhibitory potential of the VNARs against the live virus.

Example 8. Cross-Completion Between VNAR Antibodies

Epitope binning. Pairwise competition ELISA was used to perform epitope binning. Individual VNAR-hFcs were used as primary antibodies at 50 nM concentration in 100 µl to coat high-binding 96-well microplates overnight at 4° C. After blocking with 5% BSA in PBS for 1 hr, 50 nM biotinylated S1-RBD alone or premixed with 500 nM secondary (competitor) VNAR-hFc was added to the plate pairwise. Binding of biotinylated S1-RBD to coated VNAR-hFc was detected by streptavidin-HRP (Merck Millipore, 18-152). The signal intensities were collected for each primary VNAR-hFc without competitor and compared to the signal when a competitor antibody was present. If the signal remained the same, it was defined as non-competitive, whereas if the signal was decreased by at least 20% it was defined as competitive.

Results. In epitope binning experiments, the ten VNAR antibodies that blocked the interaction of S1 and S1-RBD with ACE2 in the cell-based assay were tested against each other for binding to S1-RBD. The epitope binning ELISA allowed testing of each primary VNAR antibody against each secondary VNAR antibody for competition with S1-RBD and the results are shown in FIG. 16. Competition indicated an overlap in the epitope bin between the VNAR antibodies (black boxes) and the lack of competition suggested a unique bin (white boxes). Overall, two bins were identified, with 9 out of 10 VNAR antibodies (25, 46, 61, 105, 106, 115, 119, 132 and 135) showing a shared overlap bin with VNAR antibody 68 having a unique bin.

Example 9. Performance of the OSX6 Library

Overall, the antibody discovery campaigns identified numerous antibodies against SARS-CoV-2 spike protein with ability to block its interaction with ACE2 receptor and neutralize the virus. The comparison of the two phage libraries OSX3 and OSX6 indicated that the improved design of OSX6 library resulted in increased success rate in selection of functional antibodies. While the smaller size (approximately 1/10) and the lower CDR3 diversity of the OSX6 versus OSX3 library resulted in approximately a 50% reduction in number of unique hits (100 from OSX3 versus 49 from OSX6), the OSX6 library generated approximately 50% more blocking antibodies in the ELISA competition assay (13 vs 7, Table 10), the cell-based competition assay (9 vs 6, Table 11) and live virus neutralization assay (6 vs 4, FIG. 14). The lower attrition rate during the discovery, screening, and characterization of VNAR antibodies derived from the OSX6 library was a result of improvements in VNAR design, including, independently or in combination, providing optimized scaffolds for the VNAR domains and the improved CDR3 loops of the disclosure.

REFERENCES

Baum, A., D. Ajithdoss, R. Copin, A. Zhou, K. Lanza, N. Negron, M. Ni, Y. Wei, K. Mohammadi, B. Musser, G. S. Atwal, A. Oyejide, Y. Goez-Gazi, J. Dutton, E. Clemmons, H. M. Staples, C. Bartley, B. Klaffke, K. Alfson, M. Gazi, O. Gonzalez, E. Dick, Jr., R. Carrion, Jr., L. Pessaint, M. Porto, A. Cook, R. Brown, V. Ali, J. Greenhouse, T. Taylor, H. Andersen, M. G. Lewis, N. Stahl, A. J. Murphy, G. D. Yancopoulos and C. A. Kyratsous (2020). "REGN-COV2 antibodies prevent and treat SARS-CoV-2 infection in rhesus macaques and hamsters." *Science* 370(6520): 1110-1115.

Cao, Y., B. Su, X. Guo, W. Sun, Y. Deng, L. Bao, Q. Zhu, X. Zhang, Y. Zheng, C. Geng, X. Chai, R. He, X. Li, Q. Lv, H. Zhu, W. Deng, Y. Xu, Y. Wang, L. Qiao, Y. Tan, L. Song, G. Wang, X. Du, N. Gao, J. Liu, J. Xiao, X. D. Su, Z. Du, Y. Feng, C. Qin, C. Qin, R. Jin and X. S. Xie (2020). "Potent Neutralizing Antibodies against SARS-CoV-2 Identified by High-Throughput Single-Cell Sequencing of Convalescent Patients' B Cells." *Cells* 182(1): 73-84 e16.

Doud, M. B., S. E. Hensley and J. D. Bloom (2017). "Complete mapping of viral escape from neutralizing antibodies." *PLoS Pathog* 13(3): e1006271.

Doud, M. B., J. M. Lee and J. D. Bloom (2018). "How single mutations affect viral escape from broad and narrow antibodies to H1 influenza hemagglutinin." *Nat Commun* 9(1): 1386.

Jeyanathan, M., S. Afkhami, F. Smaill, M. S. Miller, B. D. Lichty and Z. Xing (2020). "Immunological considerations for COVID-19 vaccine strategies." *Nat Rev Immunol* 20(10): 615-632.

Konning, D., S. Zielonka, J. Grzeschik, M. Empting, B. Valldorf, S. Krah, C. Schroter, C. Sellmann, B. Hock and H. Kolmar (2017). "Camelid and shark single domain antibodies: structural features and therapeutic potential." *Curr Opin Struct Biol* 45: 10-16.

Korber, B., W. Fischer, S. Gnanakaran, H. Yoon, J. Theiler, W. Abfalterer, B. Foley, E. Giorgi, T. Bhattacharya, M. Parker, D. Partridge, C. Evans, T. de Silva, C. LaBranche and D. Montefiori (2020) "Spike mutation pipeline reveals the emergence of a more transmissible form of SARS-CoV-2." *bioRxiv*: 2020.2004.2029.069054.

Liu, L., P. Wang, M. S. Nair, J. Yu, M. Rapp, Q. Wang, Y. Luo, J. F. Chan, V. Sahi, A. Figueroa, X. V. Guo, G. Cerutti, J. Bimela, J. Gorman, T. Zhou, Z. Chen, K. Y. Yuen, P. D. Kwong, J. G. Sodroski, M. T. Yin, Z. Sheng, Y. Huang, L. Shapiro and D. D. Ho (2020). "Potent neutralizing antibodies against multiple epitopes on SARS-CoV-2 spike." *Nature* 584(7821): 450-456.

Stanfield, R. L., H. Dooley, M. F. Flajnik and I. A. Wilson (2004). "Crystal structure of a shark single-domain antibody V region in complex with lysozyme." *Science* 305(5691): 1770-1773.

Thyagarajan, B. and J. D. Bloom (2014). "The inherent mutational tolerance and antigenic evolvability of influenza hemagglutinin." *Elife* 3.

Watanabe, Y., J. D. Allen, D. Wrapp, J. S. McLellan and M. Crispin (2020). "Site-specific glycan analysis of the SARS-CoV-2 spike." *Science*: eabb9983.

Watanabe, Y., T. A. Bowden, I. A. Wilson and M. Crispin (2019). "Exploitation of glycosylation in enveloped virus pathobiology." *Biochimica et Biophysica Acta (BBA) -General Subjects* 1863(10): 1480-1497.

Yang, L., W. Liu, X. Yu, M. Wu, J. M. Reichert and M. Ho (2020). "COVID-19 antibody therapeutics tracker: a global online database of antibody therapeutics for the prevention and treatment of COVID-19." *Antib Ther* 3(3): 205-212.

---

We claim:

1. A coronavirus S1 fragment-binding moiety comprising a Type II VNAR domain
capable of specifically binding to an S1 fragment comprising amino acids 16-685 of a SARS-CoV-2 spike protein and wherein said moiety comprises any one of VNAR domains 25, 46, 61, 68, 105, 106, 115, 119, 132, or 135 (SEQ ID NOS. 25, 46, 61, 68, 105, 106, 115, 119, 132, or 135, respectively).

2. The moiety of claim 1 which further comprises at least one heterologous agent operably linked to said moiety to thereby form a conjugate.

3. The moiety of claim 2, wherein said agent is selected from the group consisting of one or more of a small molecule diagnostic or therapeutic; a DNA, RNA, or hybrid DNA-RNA; a traceable marker; a radioactive agent; an antibody; a single chain variable domain; or an immunoglobulin fragment.

4. The moiety of claim 3, wherein said agent is an immunoglobulin fragment and is operably linked to said VNAR domain to form a fusion protein.

5. A pharmaceutical composition comprising at least one moiety of claim 1 or a conjugate thereof.

6. The composition of claim 5, which comprises from two to five independent moieties or conjugates.

7. A method of passive immunization against SARS-CoV-2, or a variant thereof, which comprises administering a pharmaceutical composition of claim 5 to a subject in need thereof.

8. The method of claim 7, wherein said composition is administered intravenously, subcutaneously, intramuscularly, intranasally or by inhalation.

9. A method of treating or inhibiting the development of COVID-19 which comprises administering a pharmaceutical composition of claim 5 for a time and in an amount effect to treat or inhibit the development of COVID-19.

10. The method of claim 9, wherein said composition is administered intravenously, subcutaneously, intramuscularly, intranasally or by inhalation.

11. A VNAR antibody comprising the moiety of claim 1 fused to a human Fc domain, which upon expression can dimerize to form a bivalent VNAR antibody.

12. The VNAR antibody of claim 11, wherein said VNAR antibody is capable of neutralizing infection of SARS-CoV-2 or a variant thereof.

13. A pharmaceutical composition comprising at least one VNAR antibody of claim 11.

14. The composition of claim 13 which comprises from two to five VNAR antibodies.

15. A method of passive immunization against SARS-CoV-2 or a variant thereof which comprises administering a pharmaceutical composition of claim 13 to a subject in need thereof.

16. The method of claim 15, wherein said composition is administered intravenously, subcutaneously, intramuscularly, intranasally or by inhalation.

17. A method of treating or inhibiting the development of COVID-19 which comprises administering a pharmaceutical composition of claim 13 for a time and in an amount effect to treat or inhibit the development of COVID-19.

18. The method of claim 17, wherein said composition is administered intravenously, subcutaneously, intramuscularly, intranasally or by inhalation.

19. A coronavirus S1 fragment-binding moiety comprising a Type II VNAR domain capable of specifically binding to an S1 fragment comprising amino acids 16-685 of SARS-CoV-2 spike protein, wherein said VNAR domain comprises an amino acid sequence of any one of VNAR clones 1-149 (SEQ ID NOS.1-149, respectively).

20. The moiety of claim 19 which further comprises at least one heterologous agent operably linked to said moiety to thereby form a conjugate.

21. A nucleic acid encoding the moiety of claim 1 or a conjugate thereof.

22. A vector comprising a nucleic acid of claim 21 operably linked to a promoter to enable expression of said moiety or conjugate in a host cell.

23. A host cell comprising the vector of claim 22.

24. A nucleic acid encoding the VNAR antibody of claim 11.

25. A vector comprising a nucleic acid of claim 24 operably linked to a promoter to enable expression of said VNAR antibody in a host cell.

26. A host cell comprising the vector of claim 25.

\* \* \* \* \*

SEQUENCE LISTING

```
<160> NUMBER OF SEQ ID NOS: 176

<210> SEQ ID NO 1
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Arg Val Asp Gln Thr Pro Arg Ser Val Thr Lys Glu Thr Gly Glu
1               5                   10                  15

Ser Leu Thr Ile Asn Cys Val Leu Arg Asp Asn Asn Cys Ala Leu Ser
            20                  25                  30

Thr Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Arg Arg Val Pro His Asn Cys Phe Pro Gly Asp
                85                  90                  95

Val Ile Asp Trp Asp Val Tyr Gly Asp Gly Thr Ala Val Thr Val Asn
                100                 105                 110

Ala

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val Met Ala Trp Phe Gly Glu Cys Leu Glu Asp
                85                  90                  95

Tyr Pro Asp Val Tyr Gly Asp Gly Thr Ala Val Thr Val Asn Ala
            100                 105                 110
```

<210> SEQ ID NO 3
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Gln Thr Ser Trp Arg Arg Asn Cys Asp Ala Arg
                85                  90                  95

Val Asp Val Tyr Gly Asp Gly Thr Ala Val Thr Val Asn Ala
            100                 105                 110
```

<210> SEQ ID NO 4
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
```

```
                65                  70                  75                  80
Tyr Arg Cys Lys Val Ala Leu Asp Pro Val Met Gly Thr Ser Cys
                    85                  90                  95

Gly Arg Ala Gly Trp Asp Val Tyr Gly Gly Thr Val Thr Val
                100                 105                 110

Asn Ala

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Lys Asp Ser Gly Thr
65                  70                  75                  80

Tyr Arg Cys Lys Val Trp Gln His Glu Cys Ala Gly Asp Tyr Leu Leu
                85                  90                  95

Gly Leu Ala Gly Asp Val Tyr Gly Asp Gly Thr Ala Val Thr Val Asn
                100                 105                 110

Ala

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Leu Trp Leu Val Gly Cys His Pro Gln Gly Asp
                85                  90                  95

Val Tyr Gly Asp Gly Thr Ala Val Thr Val Asn Ala
                100                 105

<210> SEQ ID NO 7
<211> LENGTH: 114
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Glu Ser Gln Trp Thr Gly Arg Glu Asn Arg Cys
                85                  90                  95

Val Trp Val Ile Ala Asp Val Tyr Gly Asp Gly Thr Ala Val Thr Val
                100                 105                 110

Asn Ala

<210> SEQ ID NO 8
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Val Ala Leu Asp Pro Val Met Arg Thr Ser Cys
                85                  90                  95

Gly Arg Ala Gly Trp Asp Val Tyr Gly Gly Gly Thr Val Val Thr Val
                100                 105                 110

Asn Ala

<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Arg Val Asp Gln Thr Pro Arg Ser Val Thr Lys Glu Thr Gly Glu
1               5                   10                  15
```

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Ser Phe Tyr Pro Asn Ser Trp Cys Trp Asn Arg
                85                  90                  95

Gln Lys Asp Val Tyr Gly Gly Gly Thr Ala Val Thr Val Asn Ala
            100                 105                 110

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Lys Val His Glu Ile Val Ser Ala Val Cys Gly Phe Thr
                85                  90                  95

Gln Val Lys Asp Val Tyr Gly Gly Gly Thr Val Val Thr Val Asn Ala
            100                 105                 110

<210> SEQ ID NO 11
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Phe Ala Val Arg Pro Pro Met Met His Leu Cys
                85                  90                  95

Ser Arg Gly Gln Ser Asp Val Tyr Gly Gly Thr Ala Val Thr Val
            100                 105                 110

Asn Ala

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Leu Val Trp Ser Asn Gly Thr Val Gly Met Asp
                85                  90                  95

Val Tyr Gly Gly Gly Thr Val Val Thr Val Asn Ala
            100                 105

<210> SEQ ID NO 13
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Lys Val Ala Pro Gly Trp Ala Gly Met Trp Gly Arg Ala
                85                  90                  95

Ala Cys Asp Val Tyr Gly Gly Thr Val Val Thr Val Asn Ala
            100                 105                 110

<210> SEQ ID NO 14
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65              70                  75                  80

Tyr Arg Cys Lys Val Ser Arg Tyr Val Leu Glu Arg His Ser Val Cys
                85                  90                  95

Phe His Ser Leu Ala Asp Val Tyr Gly Gly Gly Thr Val Thr Val
                100                 105                 110

Asn Ala

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65              70                  75                  80

Tyr Arg Cys Lys Val Ala Ser Val Asp Val Asn Pro Ser Pro Gln Gly
                85                  90                  95

Pro Val Gln Val Val Tyr Gly Gly Thr Val Thr Val Asn Ala
                100                 105                 110

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

```
Ser Phe Ser Leu Arg Ile Asn Asp Leu Thr Val Lys Asp Ser Gly Thr
 65                  70                  75                  80

Tyr Arg Cys Lys Val His Glu Asn Leu Tyr Ser His Cys Gln Phe Ser
                 85                  90                  95

Leu Pro Thr Asp Val Tyr Gly Gly Gly Thr Val Val Thr Val Asn Ala
            100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Ala Arg Val Asp Gln Thr Pro Gln Thr Ile Thr Lys Glu Thr Gly Glu
  1               5                  10                  15

Ser Leu Thr Ile Asn Cys Val Leu Arg Asp Asn Asn Cys Ala Leu Ser
                 20                  25                  30

Thr Thr Tyr Trp Tyr Arg Lys Lys Ser Asp Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Phe Ala Tyr Tyr Pro Gln Tyr Cys Asn Val Leu
                 85                  90                  95

Ala Gln Asp Val Tyr Gly Gly Gly Thr Val Val Thr Val Asn Ala
            100                 105                 110
```

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Asn Cys Asp Leu Ser
                 20                  25                  30

Arg Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Pro Ile Phe Gly Trp Val Gly Phe Cys Asp Leu
                 85                  90                  95

Thr Trp Asp Asp Val Tyr Gly Asp Gly Thr Ala Val Thr Val Asn Ala
            100                 105                 110
```

<210> SEQ ID NO 19
<211> LENGTH: 114
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 19

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Lys Leu Val His Ala Val Gly Gly Glu Gly Cys
                85                  90                  95

Ser Gly Ala Leu Ile Asp Val Tyr Gly Gly Gly Thr Ala Val Thr Val
            100                 105                 110

Asn Ala

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Val His Pro Gln Ala Ala Cys Gly Gln His
                85                  90                  95

Leu Asp Val Tyr Gly Gly Gly Thr Ala Val Thr Val Asn Ala
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

```
Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Phe Gln Tyr Cys Glu Glu Asp Cys Trp Gly Ile
                 85                  90                  95

Trp Glu Trp Asp Val Tyr Gly Gly Thr Ala Val Thr Val Asn Ala
                100                 105                 110
```

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Pro
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Glu Gly Phe Leu Gly Ser Cys Asp Ser Met Trp
                 85                  90                  95

Trp Asp Asp Val Tyr Gly Asp Gly Thr Ala Val Thr Val Asn Ala
                100                 105                 110
```

<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Ile Cys Ala Leu Ser
                 20                  25                  30

Ser Thr His Trp Tyr Arg Lys Lys Ser Gly Ser Thr Asn Glu Ala Arg
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Gln Val His Pro Gln Ala Ala Cys Gly Gln Gln
                 85                  90                  95

Leu Asp Val Tyr Gly Gly Gly Thr Ala Val Thr Val Asn Ala
                100                 105                 110
```

<210> SEQ ID NO 24

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Val Ser Asp Cys Gly Tyr Ser Tyr Asp Val
                85                  90                  95

Tyr Gly Gly Gly Thr Ala Val Thr Val Asn Ala
            100                 105

<210> SEQ ID NO 25
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
50                  55                  60

Ser Phe Ser Leu Lys Ile Asn Asp Leu Thr Val Glu Asp Ser Gly Thr
65                  70                  75                  80

Tyr Arg Cys Lys Val His Met Glu Asp Met Asn Val Arg Asp Tyr Gly
                85                  90                  95

Gly Phe Trp Gly Glu Asp Val Tyr Gly Gly Thr Val Val Thr Val
            100                 105                 110

Asn Ala

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser

```
            20                  25                  30
Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Ser Arg Gly Leu Pro Gly Gly Gly Ala Glu
                85                  90                  95

Trp Cys Asp Val Tyr Gly Gly Gly Thr Val Thr Val Asn Ala
                100                 105                 110

<210> SEQ ID NO 27
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Asn Val His Val Asp Tyr Tyr Ser Tyr Cys Thr
                85                  90                  95

Gly Phe Asp Val Asp Val Tyr Gly Gly Gly Thr Ala Val Thr Val Asn
                100                 105                 110

Ala

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Gln Asn Val Phe Trp Asn Val Cys Gln Phe His
                85                  90                  95
```

Arg Glu Arg Asp Val Tyr Gly Gly Thr Val Val Thr Val Asn Ala
            100                 105                 110

<210> SEQ ID NO 29
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Lys Asp Ser Gly Thr
65                  70                  75                  80

Tyr Arg Cys Lys Val Trp Arg Glu Pro Arg Val Cys Arg Ala Ala Leu
                85                  90                  95

Ser Asn Gly Leu Asp Val Tyr Gly Gly Gly Thr Ala Val Thr Val Asn
            100                 105                 110

Ala

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30

Ser Thr Tyr Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Leu Ala Val Val Glu Ser Asp Gly Ser Phe Met
                85                  90                  95

Ser Glu Asp Val Tyr Gly Gly Gly Thr Ala Val Thr Val Asn Ala
            100                 105                 110

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Pro Leu Ser Phe Cys Pro Trp His Phe Asp Val
                85                  90                  95

Tyr Gly Gly Gly Thr Val Val Thr Val Asn Ala
            100                 105

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Arg Phe Asn Cys Tyr Asp His Cys Gly Asp Val
                85                  90                  95

Tyr Gly Gly Gly Thr Ala Val Thr Val Asn Ala
            100                 105

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr

```
                65                  70                  75                  80

Tyr Arg Cys Lys Val Phe Val His Asp Val Asn Val Asn Pro Gly Cys
                    85                  90                  95

His Pro Gly Asp Val Tyr Gly Gly Gly Thr Ala Val Thr Val Asn Ala
                100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Arg Ser Ala Leu Gly Leu Asp Gly Tyr Ala Cys
                85                  90                  95

Trp Val Asp Val Tyr Gly Gly Gly Thr Val Val Thr Val Asn Ala
                100                 105                 110

<210> SEQ ID NO 35
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Val Ala Thr Ile Asp Ser Leu Gly Leu Gly Cys Gly
                85                  90                  95

Met Trp Gln Gly Tyr Asp Val Tyr Gly Gly Gly Thr Val Val Thr Val
                100                 105                 110

Asn Ala

<210> SEQ ID NO 36
<211> LENGTH: 109
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 36

Ala Arg Val Asp Gln Thr Pro Arg Ser Val Thr Lys Glu Thr Gly Glu
1               5                   10                  15

Ser Leu Thr Ile Asn Cys Val Leu Arg Asp Asn Asn Cys Ala Leu Ser
            20                  25                  30

Thr Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Val Val Glu Asp Ser Gly Thr
65                  70                  75                  80

Tyr Arg Cys Asn Val Ser Cys Thr Phe Val Gly Tyr Gly Met Leu Glu
                85                  90                  95

Asp Val Tyr Gly Gly Gly Thr Ala Val Thr Val Asn Ala
            100                 105

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Arg Leu Glu Ser Asp Gly Trp Asp Gly Ala Trp
                85                  90                  95

Gly Trp Glu Asp Val Tyr Gly Asp Gly Thr Ala Val Thr Val Asn Ala
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45
```

```
Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Phe Thr Thr Leu Asn Asp Ile Cys His Trp Met
                 85                  90                  95

Trp Ser Lys Asp Val Tyr Gly Asp Gly Thr Ala Val Thr Val Asn Ala
                100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                 20                  25                  30

Ser Thr Leu Trp Tyr Arg Thr Lys Ser Gly Ser Arg Asn Glu Ala Arg
             35                  40                  45

Ile Ser Lys Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Asn Val Leu Cys Val Gln Ser Leu Arg Cys Glu Phe Thr
                 85                  90                  95

Ser Glu Asp Val Tyr Gly Gly Gly Thr Val Val Thr Val Asn Ala
                100                 105                 110

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Leu Leu Met Asp Asn Tyr Gly Ala Leu Arg Asp
                 85                  90                  95

Val Tyr Gly Gly Gly Thr Ala Val Thr Val Asn Ala
                100                 105

<210> SEQ ID NO 41
<211> LENGTH: 113
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Gly Ser Tyr Tyr Ile Leu Asn Gly Gly Ala Trp
                85                  90                  95

Arg Ser Arg Ala Asp Val Tyr Gly Gly Gly Thr Ala Val Thr Val Asn
            100                 105                 110

Ala

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Lys Val Arg Arg Leu Pro His Leu Cys Gln Val Glu Thr
                85                  90                  95

Ile Ser Val Trp Asp Val Tyr Gly Asp Gly Thr Ala Val Thr Val Asn
            100                 105                 110

Ala

<210> SEQ ID NO 43
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
65                  70                  75                  80

Tyr Arg Cys Asn Val Trp Gln Ile Asp Asp Tyr Gly His Arg Ala Asp
                85                  90                  95

Val Tyr Gly Gly Gly Thr Ala Val Thr Val Asn Ala
            100                 105

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
65                  70                  75                  80

Tyr Arg Cys Asn Val Arg Thr Val Pro Leu Trp Asn Asp Cys Asp Val
                85                  90                  95

Phe Glu Asp Val Tyr Gly Gly Gly Thr Ala Val Thr Val Asn Ala
            100                 105                 110

<210> SEQ ID NO 45
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Val Val Glu Asp Ser Gly Thr
65                  70                  75                  80

Tyr Arg Cys Asn Val Val Ser Leu Phe Ser Gln Gly Ser Ser Phe Phe
                85                  90                  95

```
Trp Asp Val Tyr Gly Gly Gly Thr Ala Val Thr Val Asn Ala
            100                 105                 110
```

<210> SEQ ID NO 46
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Asn Leu Arg Ser Val Leu Pro Cys Gly Trp Pro
                85                  90                  95

Asp Val Tyr Gly Asp Gly Thr Ala Val Thr Val Asn Ala
            100                 105
```

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Lys Val Phe Gln His Leu Ala Leu Gly Tyr Asp Ala Met
                85                  90                  95

Cys His Val Gly Asp Val Tyr Gly Gly Gly Thr Ala Val Thr Val Asn
            100                 105                 110

Ala
```

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

-continued

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Leu Glu Val Phe Cys Phe Tyr Gly Asn Gln Gly
                85                  90                  95

Thr Asp Val Tyr Gly Asp Gly Thr Ala Val Thr Val Asn Ala
            100                 105                 110

<210> SEQ ID NO 49
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Asp Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Trp Asp Leu Ile Ser Met Glu Cys Trp Trp Ala
                85                  90                  95

Asp Val Tyr Gly Asp Gly Thr Ala Val Thr Val Asn Ala
            100                 105

<210> SEQ ID NO 50
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Lys Asp Ser Gly Thr
65                  70                  75                  80

```
Tyr Arg Cys Lys Val Thr Val Leu Pro His Val Cys Pro Asp Met Glu
                85                  90                  95

Pro Leu Phe Val Asp Val Tyr Gly Asp Gly Thr Ala Val Thr Val Asn
            100                 105                 110

Ala

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Gln Phe Ile Asp Tyr Asn Cys Gly Trp Asp Val
                85                  90                  95

Tyr Gly Gly Gly Thr Val Val Thr Val Asn Ala
            100                 105

<210> SEQ ID NO 52
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Val Ile Ser Ala Leu Ser Trp Phe Asn Asp Ser Tyr
                85                  90                  95

Gln Ala Cys Trp Val Asp Val Tyr Gly Gly Gly Thr Val Val Thr Val
            100                 105                 110

Asn Ala

<210> SEQ ID NO 53
<211> LENGTH: 110
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 53

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Gln Thr Ser Trp Arg Arg Val Cys Asp Val Gly
                85                  90                  95

Met Asp Val Tyr Gly Asp Gly Thr Ala Val Thr Val Asn Ala
            100                 105                 110

<210> SEQ ID NO 54
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Gly Pro Lys Val Cys Phe Arg Phe Tyr Gly Asp
                85                  90                  95

Arg Ser Gly Phe Asp Asp Val Tyr Gly Gly Thr Ala Val Thr Val
            100                 105                 110

Asn Ala

<210> SEQ ID NO 55
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

```
Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Leu Leu Gln Asp Gly Tyr Gly Ala Leu Asn Asp
                85                  90                  95

Val Tyr Gly Gly Gly Thr Ala Val Thr Val Asn Ala
                100                 105

<210> SEQ ID NO 56
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Glu Leu Ser
                20                  25                  30

Ser Thr Tyr Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Gly Ser Leu Trp Val Lys Ser Gly Gly Asp Ser
                85                  90                  95

Trp Gly Arg Arg Asp Asp Val Tyr Gly Gly Gly Thr Val Val Thr Val
                100                 105                 110

Asn Ala

<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Lys Val Arg Arg Leu Gly Cys Asp Leu Asp Gln Met Phe
                85                  90                  95

Lys Ser Trp Asp Val Tyr Gly Gly Gly Thr Val Val Thr Val Asn Ala
```

-continued

```
                100                 105                 110
```

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Glu Gly Phe Leu Gly Ser Cys Asp Ser Met Trp
                85                  90                  95

Trp Asp Asp Val Tyr Gly Asp Gly Thr Ala Val Thr Val Asn Ala
                100                 105                 110
```

<210> SEQ ID NO 59
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Ser Val Leu Cys Leu Asp Tyr Tyr Phe Leu Gly
                85                  90                  95

Leu Lys Leu Asp Val Tyr Gly Asp Gly Thr Val Val Thr Val Asn Ala
                100                 105                 110
```

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Ala Arg Val Asp Gln Thr Pro Gln Thr Val Thr Lys Glu Thr Gly Glu
1               5                   10                  15
```

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Asn Glu Leu Phe Gly Ser Asp Gly Asn Val Ala
                85                  90                  95

Ser Asp Val Tyr Gly Gly Gly Thr Val Val Thr Val Asn Ala
            100                 105                 110

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Lys Val Glu Asn Leu Pro Gly Ser Gly Ser Cys Leu Arg
                85                  90                  95

Tyr Tyr Leu Ser Asp Val Tyr Gly Gly Gly Thr Val Val Thr Val Asn
            100                 105                 110

Ala

<210> SEQ ID NO 62
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

```
Tyr Arg Cys Lys Val Val Ala Gln Gly Gln Leu Gly Ala Ile Met Asp
                85                  90                  95

Val Tyr Gly Gly Gly Thr Val Thr Val Asn Ala
            100                 105

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Val Ala Thr Ser Trp Gly Gly Asp Tyr Ser Gln Arg
                85                  90                  95

Tyr Val Gly Ser Asp Val Tyr Gly Gly Gly Thr Val Val Thr Val Asn
            100                 105                 110

Ala

<210> SEQ ID NO 64
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Ile Glu Thr Phe Pro Tyr Gly Cys Leu Gly
                85                  90                  95

His Asp Val Tyr Gly Gly Gly Thr Val Val Thr Val Asn Ala
            100                 105                 110

<210> SEQ ID NO 65
<211> LENGTH: 111
<212> TYPE: PRT
<213> ORGANISM: Artificial Sequence
<220> FEATURE:
<223> OTHER INFORMATION: Description of Artificial Sequence: Synthetic
```

```
              polypeptide

<400> SEQUENCE: 65

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Ala Gly Leu Pro Gly Phe Cys Lys Val Leu
                85                  90                  95

Glu Glu Asp Val Tyr Gly Asp Gly Thr Ala Val Thr Val Asn Ala
            100                 105                 110

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Trp Cys Asn Ala Asp Lys Gly Asp Ser Lys Val
                85                  90                  95

Cys Cys Leu Arg Asp Val Tyr Gly Gly Thr Ala Val Thr Val Asn
            100                 105                 110

Ala

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45
```

```
Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Phe Cys Gly Asn Tyr Cys Cys Leu Arg Asp Val
                 85                  90                  95

Tyr Gly Asp Gly Thr Ala Val Thr Val Asn Ala
            100                 105
```

<210> SEQ ID NO 68
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Asn Cys Ala Leu Pro
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Lys Val Arg Glu Trp Ala Cys Glu Asp Asp Gly Arg Val
                 85                  90                  95

Trp Gly Trp Glu Asp Val Tyr Gly Asp Gly Thr Ala Val Thr Val Asn
            100                 105                 110

Ala
```

<210> SEQ ID NO 69
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Ile Cys Ala Leu Ser
                 20                  25                  30

Ser Thr His Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Asn Val Ser Gly Trp Ser Gly Tyr Gly Cys Leu Leu Arg
                 85                  90                  95

Asp Val Tyr Gly Gly Gly Thr Ala Val Thr Val Asn Ala
            100                 105
```

```
<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Tyr Thr Leu Trp Asp Tyr Cys Thr Ser Ala Asp
                85                  90                  95

Ser Leu Ala Gly Asp Val Tyr Gly Gly Thr Ala Val Thr Val Asn
            100                 105                 110

Ala

<210> SEQ ID NO 71
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Lys Val Lys Glu Met His Val Asp Arg Val Arg Val Leu
                85                  90                  95

Cys Gly Asp Ala Glu Leu Asp Val Tyr Gly Asp Gly Thr Thr Val Thr
            100                 105                 110

Val Asn Ala
        115

<210> SEQ ID NO 72
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72
```

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr His Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Lys Ile Asn Asp Leu Thr Val Glu Asp Ser Gly Thr
65                  70                  75                  80

Tyr Arg Cys Asn Val Gly Asp Pro Phe Gly Arg Tyr Gly Cys Leu Ser
                85                  90                  95

Ser Asp Val Tyr Gly Gly Gly Thr Val Val Thr Val Asn Ala
                100                 105                 110

<210> SEQ ID NO 73
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Ser Gly Trp Gly Gly Phe Gly Cys Leu Arg Val
                85                  90                  95

Asp Val Tyr Gly Gly Gly Thr Val Val Thr Val Asn Ala
                100                 105

<210> SEQ ID NO 74
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

```
Tyr Arg Cys Lys Val Trp Ser His Asp Pro Tyr Gly Gly Ala Cys Phe
                85                  90                  95

Pro Pro Gly Ser Arg Asp Val Tyr Gly Gly Thr Val Thr Val
            100                 105                 110

Asn Ala
```

<210> SEQ ID NO 75
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Lys Ala Met Asp Trp Tyr Tyr Gly His Trp Cys
                85                  90                  95

Gly Asp Val Tyr Gly Gly Gly Thr Ala Val Thr Val Asn Ala
            100                 105                 110
```

<210> SEQ ID NO 76
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Val Ser Arg Phe Tyr Gly Leu Cys Ala Asn Asp
                85                  90                  95

Arg Phe Asp Val Tyr Gly Asp Gly Thr Ala Val Thr Val Asn Ala
            100                 105                 110
```

<210> SEQ ID NO 77
<211> LENGTH: 112
<212> TYPE: PRT
<213> ORGANISM: Artificial Sequence
<220> FEATURE:
<223> OTHER INFORMATION: Description of Artificial Sequence: Synthetic

```
              polypeptide

<400> SEQUENCE: 77

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Lys Asp Ser Gly Thr
65                  70                  75                  80

Tyr Arg Cys Lys Val Arg Met Glu Tyr Glu Gly Ala Gly Pro Ser Gly
                85                  90                  95

Gly Trp Val Asp Val Tyr Gly Gly Gly Thr Val Val Thr Val Asn Ala
            100                 105                 110

<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Arg Cys Ile Ser Ser Leu Cys Ser Tyr Trp Met
                85                  90                  95

Gly Asp Val Tyr Gly Gly Gly Thr Val Val Thr Val Asn Ala
            100                 105                 110

<210> SEQ ID NO 79
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60
```

```
Ser Phe Ser Leu Arg Ile Asn Asp Leu Thr Val Glu Asp Ser Gly Thr
 65                  70                  75                  80

Tyr Arg Cys Lys Val Ala Ser Thr His Asn Ala Cys Ile Gln Leu Thr
                 85                  90                  95

Met Arg Ser Arg Asp Val Tyr Gly Gly Gly Thr Ala Val Thr Val Asn
                100                 105                 110

Ala
```

<210> SEQ ID NO 80
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
                 35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Arg Ser Leu Val Ser Phe Asp Gly Tyr Ala Cys
                 85                  90                  95

Trp Ala Asp Val Tyr Gly Gly Gly Thr Val Val Thr Val Asn Ala
                100                 105                 110
```

<210> SEQ ID NO 81
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
                 35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Trp Arg His Glu Cys Ala Tyr Asp Tyr Ser Gly
                 85                  90                  95

Pro Gly Cys His Asp Val Tyr Gly Gly Gly Thr Ala Val Thr Val Asn
                100                 105                 110

Ala
```

<210> SEQ ID NO 82
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Cys Thr Thr Arg Leu Ser Cys Tyr Ala Met
                85                  90                  95

Phe Val Asp Val Tyr Gly Asp Gly Thr Ala Val Thr Val Asn Ala
            100                 105                 110

<210> SEQ ID NO 83
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Phe Leu His Val Ala Arg Ser Gly Met Met Cys
                85                  90                  95

Met Asp Gln Leu Gly Asp Val Tyr Gly Gly Gly Thr Ala Val Thr Val
            100                 105                 110

Asn Ala

<210> SEQ ID NO 84
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Arg Val Asp Gln Thr Pro Gln Thr Ile Thr Lys Glu Thr Gly Glu
1               5                   10                  15

-continued

Ser Leu Thr Ile Asn Cys Val Leu Arg Asp Ser Asn Cys Ala Leu Ser
              20                  25                  30

Ser Thr Tyr Trp Tyr Arg Lys Lys Ser Gly Ser Thr Asn Glu Glu Ser
              35                  40                  45

Ile Ser Lys Gly Gly Arg Tyr Val Glu Thr Val Asn Ser Gly Ser Lys
         50                  55                  60

Ser Phe Ser Leu Arg Ile Asn Asp Leu Thr Val Glu Asp Ser Gly Thr
65                  70                  75                  80

Tyr Arg Cys Lys Val Leu Ser Leu Asp Ala Lys Tyr Gly Gly Phe Cys
                 85                  90                  95

Trp Ile Glu Gly Ala Asp Val Tyr Gly Asp Gly Thr Ala Val Thr Val
            100                 105                 110

Asn Ala

<210> SEQ ID NO 85
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
              20                  25                  30

Arg Thr Tyr Trp Tyr Arg Lys Lys Ser Gly Ser Thr Asn Glu Glu Ser
              35                  40                  45

Ile Ser Lys Gly Gly Arg Tyr Val Glu Thr Val Asn Ser Gly Ser Lys
         50                  55                  60

Ser Phe Ser Leu Arg Ile Asn Asp Leu Val Val Glu Asp Ser Gly Thr
65                  70                  75                  80

Tyr Arg Cys Lys Val Phe Val Leu Asn Leu Glu Tyr Gly Thr Ile Cys
                 85                  90                  95

Gly Ser Ser Gly Asp Val Tyr Gly Asp Gly Thr Ala Val Thr Val
            100                 105                 110

Asn Ala

<210> SEQ ID NO 86
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
              20                  25                  30

Asn Leu Tyr Trp Tyr Arg Lys Lys Ser Gly Ser Thr Asn Glu Glu Ser
              35                  40                  45

Ile Ser Leu Gly Gly Arg Tyr Val Glu Thr Val Asn Ser Gly Ser Lys
         50                  55                  60

Ser Phe Ser Leu Arg Ile Asn Asp Leu Thr Val Glu Asp Ser Gly Thr
65                  70                  75                  80

```
Tyr Arg Cys Lys Val Lys Pro Ile Glu Met Lys Trp Gly Tyr Gly Cys
                85                  90                  95

Gly Gly Arg His Trp Asp Val Tyr Gly Gly Thr Val Thr Val
            100                 105                 110

Asn Ala

<210> SEQ ID NO 87
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Val Phe Ser His Glu Asp Gly Asn Trp Cys Gly Gly
                85                  90                  95

Gly Asp Arg Ala Arg Asp Val Tyr Gly Gly Thr Ala Val Thr Val
            100                 105                 110

Asn Ala

<210> SEQ ID NO 88
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Leu Trp Tyr Arg Thr Lys Ser Gly Ser Thr Asn Glu Glu Ser
            35                  40                  45

Ile Ser Leu Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Ile Ser Arg Phe Tyr Gly Ile Cys Gln Leu Gly
                85                  90                  95

Ala Asp Val Tyr Gly Gly Gly Thr Ala Val Thr Val Asn Ala
            100                 105                 110

<210> SEQ ID NO 89
<211> LENGTH: 113
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 89

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Thr Gln Phe Asp Cys Ala Asn Gly Tyr Leu Ser
                85                  90                  95

Ala Val Glu Ala Asp Val Tyr Gly Gly Thr Ala Val Thr Val Asn
            100                 105                 110

Ala

<210> SEQ ID NO 90
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Tyr Gly Arg Asp Gly Tyr Cys Val Met Ala Asp
                85                  90                  95

Val Tyr Gly Asp Gly Thr Ala Val Thr Val Asn Ala
            100                 105

<210> SEQ ID NO 91
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

```
Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Trp Gly Ala Asp Asp Tyr Gly Ser Gly Ser Asp
                 85                  90                  95

Val Tyr Gly Gly Gly Thr Val Val Thr Val Asn Ala
                100                 105
```

<210> SEQ ID NO 92
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Glu Leu Ser
                20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Leu Ala Gln Asp Val Asp Tyr Gly Gly Leu Ser
                 85                  90                  95

Asp Val Tyr Gly Gly Gly Thr Ala Val Thr Val Asn Ala
                100                 105
```

<210> SEQ ID NO 93
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Asn Val Phe Asn His Ala Thr Gly Leu Cys Gln Leu Trp
                 85                  90                  95

Asp Val Tyr Gly Asp Gly Thr Ala Val Thr Val Asn Ala
                100                 105
```

<210> SEQ ID NO 94
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Val Gly Leu Tyr Arg Ser Val Cys Leu Ser Ala
                85                  90                  95

Thr Gly Ala Asp Val Tyr Gly Gly Gly Thr Ala Val Thr Val Asn Ala
            100                 105                 110

<210> SEQ ID NO 95
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu His
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Asn Val Ile Ala Arg Tyr Tyr Gly Leu Cys Asp Leu Asp
                85                  90                  95

Asp Val Tyr Gly Asp Gly Thr Ala Val Thr Val Asn Ala
            100                 105

<210> SEQ ID NO 96
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro

```
                    20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
         50                  55                  60

Ser Phe Ser Leu Arg Ile Asn Asp Leu Thr Val Glu Asp Ser Gly Thr
 65                  70                  75                  80

Tyr Arg Cys Lys Val Phe Cys Ser Ala Gly Leu Gly Cys Tyr Ala Gln
                 85                  90                  95

Phe Ala Ser Asp Val Tyr Gly Asp Gly Thr Ala Val Thr Val Asn Ala
                100                 105                 110
```

<210> SEQ ID NO 97
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Ala Arg Val Asp Gln Thr Pro Arg Ser Val Thr Lys Glu Thr Gly Glu
  1               5                  10                  15

Ser Leu Thr Ile Asn Cys Val Leu Arg Asp Ser Ile Cys Ala Leu Ser
             20                  25                  30

Ser Thr His Trp Tyr Arg Lys Lys Ser Gly Ser Thr Asn Glu Glu Ser
         35                  40                  45

Ile Ser Leu Gly Gly Arg Tyr Val Glu Thr Val Asn Ser Gly Ser Lys
     50                  55                  60

Ser Phe Ser Leu Arg Ile Asn Asp Leu Thr Val Glu Asp Ser Gly Thr
 65                  70                  75                  80

Tyr Arg Cys Asn Val Arg Gln Leu Leu Cys Gly Gly Pro Gly Ser
                 85                  90                  95

Asp Val Tyr Gly Asp Gly Thr Ala Val Thr Val Asn Ala
                100                 105
```

<210> SEQ ID NO 98
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Asn Cys Asp Leu Ser
             20                  25                  30

Arg Thr Tyr Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Lys Ile Asn Asp Leu Thr Val Glu Asp Ser Gly Thr
 65                  70                  75                  80

Tyr Arg Cys Lys Val Ile Gly Tyr Val Ala Asn Asp Tyr Gly Leu
                 85                  90                  95

Arg Val Ile Asp Asp Val Tyr Gly Gly Gly Thr Ala Val Thr Val Asn
```

-continued

<210> SEQ ID NO 99
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Leu Leu Tyr Gly Leu Phe Pro Cys Ser Ser Val
                85                  90                  95

Asp Val Tyr Gly Gly Gly Thr Ala Val Thr Val Asn Ala
            100                 105

<210> SEQ ID NO 100
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Arg Arg Leu Ser His Met Cys Leu Thr Val Ser
                85                  90                  95

Gly Leu Ser Trp Asp Val Tyr Gly Gly Gly Thr Ala Val Thr Val Asn
            100                 105                 110

Ala

<210> SEQ ID NO 101
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 101

Ala Arg Val Asp Gln Thr Pro Gln Ala Ile Thr Lys Glu Thr Gly Glu
1               5                   10                  15

Ser Leu Thr Ile Asn Cys Val Leu Arg Asp Ser Asn Cys Pro Leu Ser
            20                  25                  30

Asn Thr Tyr Trp Tyr Arg Lys Asn Ser Gly Ser Thr Asn Glu Glu Arg
        35                  40                  45

Leu Ser Asn Asp Tyr Arg Thr Val Glu Thr Val Asn Ser Ala Ser Asn
50                  55                  60

Ser Phe Ser Leu Arg Ile Asn Asp Leu Thr Val Glu Asp Thr Gly Thr
65                  70                  75                  80

Tyr Arg Cys Ser Ala Arg Met Tyr Tyr Cys Asp Leu Gly His Trp Ala
                85                  90                  95

Pro Asp Leu Tyr Gly Gly Gly Thr Ala Val Thr Val Asn Ala
            100                 105                 110

<210> SEQ ID NO 102
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Ile Cys Thr Ala Ser
            20                  25                  30

Asn Thr Tyr Trp Tyr Arg Lys Lys Ser Gly Ser Glu Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Phe Glu Asp Ser Gly Thr
65                  70                  75                  80

Tyr Arg Cys Lys Ala Ile Phe Gln Ser Gly Cys Gly Val Tyr His Arg
                85                  90                  95

Tyr Thr Gly Val Tyr Gly Gly Gly Thr Val Val Thr Val Asn Ala
            100                 105                 110

<210> SEQ ID NO 103
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ala Arg Val Asp Gln Thr Pro Gln Thr Ile Thr Lys Glu Thr Gly Glu
1               5                   10                  15

Ser Leu Thr Ile Lys Cys Val Leu Gln Asn Ser Ile Cys Ala Leu Ser
            20                  25                  30

Ser Thr Tyr Trp Tyr Trp Lys Lys Ser Gly Ser Ile Asn Glu Glu Glu
        35                  40                  45

Ile Ser Lys Gly Gly Arg Tyr Val Glu Thr Ile Asn Ser Glu Ser Lys
50                  55                  60

Ser Phe Ser Leu Arg Ile Asn Asp Leu Thr Val Glu Asp Ser Gly Thr

```
                    65                  70                  75                  80
Tyr Arg Cys Ala Ile Val Arg Gln Ser Gly Cys Glu Val Ala Thr Phe
                    85                  90                  95

Lys Ala Asp Val Tyr Gly Gly Gly Thr Val Val Thr Val Asn Ala
                100                 105                 110
```

<210> SEQ ID NO 104
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Val Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Ile Asn Ser Gly Ser Lys
        50                  55                  60

Ser Phe Ser Leu Arg Ile Asn Asp Leu Ala Val Glu Asp Ser Gly Thr
65                  70                  75                  80

Tyr Arg Cys Lys Ser Glu Phe Lys Ser Gly Cys Gly Val Phe Tyr Glu
                85                  90                  95

Leu Thr Asp Val Tyr Gly Gly Thr Ala Val Thr Val Asn Ala
                100                 105                 110
```

<210> SEQ ID NO 105
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Ala Arg Val Asp Gln Thr Pro Gln Thr Ile Thr Lys Glu Thr Gly Glu
1               5                   10                  15

Ser Val Thr Ile Asn Cys Val Leu Arg Asp Ser Ile Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Val Ala Arg Thr Ser Gly Cys Glu Val Tyr Thr Tyr
                85                  90                  95

Thr Gly Asp Val Tyr Gly Gly Gly Thr Val Val Thr Val Asn Ala
                100                 105                 110
```

<210> SEQ ID NO 106
<211> LENGTH: 111
<212> TYPE: PRT
<213> ORGANISM: Artificial Sequence
<220> FEATURE:
<223> OTHER INFORMATION: Description of Artificial Sequence: Synthetic

```
                   polypeptide

<400> SEQUENCE: 106

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr Tyr Trp Tyr Arg Lys Lys Ser Gly Ser Arg Lys Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Ile Glu Asp Ser Gly Thr
65                  70                  75                  80

Tyr Gln Cys Lys Val Ala Arg Thr Ser Gly Cys Glu Val Tyr Thr Tyr
                85                  90                  95

Thr Gly Asp Val Tyr Gly Gly Gly Thr Val Val Thr Val Asn Ala
            100                 105                 110

<210> SEQ ID NO 107
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Arg Val Asp Gln Thr Pro Gln Thr Ile Thr Lys Glu Thr Gly Gly
1               5                   10                  15

Ser Val Thr Ile Asn Cys Val Leu Leu Tyr Ser Asp Cys Pro Leu Ser
            20                  25                  30

Ser Thr Tyr Trp Tyr His Lys Lys Ser Gly Ser Thr Asn Glu Glu Arg
        35                  40                  45

Ile Arg Asn Glu Asn Arg Tyr Val Glu Thr Val Asn Ser Gly Ser Lys
    50                  55                  60

Ser Phe Ser Leu Thr Ile Asn Asp Leu Thr Val Glu Asp Ser Gly Thr
65                  70                  75                  80

Tyr Arg Cys Lys Tyr Gly Ser Ile Asp Val Cys Tyr Leu Thr Asn Asn
                85                  90                  95

Glu Arg Asp Val Tyr Gly Gly Gly Thr Val Val Thr Val Asn Ala
            100                 105                 110

<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ala Arg Val Asp Gln Thr Pro Gln Thr Ile Thr Lys Glu Thr Gly Glu
1               5                   10                  15

Ser Val Thr Ile Asn Cys Val Leu Arg Asp Ser Ile Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60
```

Ser Phe Ser Leu Arg Ile Asn Asp Leu Thr Val Glu Asp Ser Gly Thr
65                  70                  75                  80

Tyr Arg Cys Ala Ile Val Arg Gln Ser Gly Cys Trp Val Ser Leu His
                85                  90                  95

Glu Glu Asp Val Tyr Gly Gly Gly Thr Val Val Thr Val Asn Ala
            100                 105                 110

<210> SEQ ID NO 109
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Arg Val Asp Gln Thr Pro Gln Thr Ile Thr Lys Leu Thr Gly Glu
1               5                   10                  15

Ser Leu Thr Ile Asn Cys Val Leu Arg Asp Thr Tyr Cys Ala Leu Ser
                20                  25                  30

Asn Thr Asn Trp Tyr His Lys Lys Ser Gly Ser Thr His Glu Glu Ser
            35                  40                  45

Ile Ser Lys Gly Gly Arg Tyr Val Glu Thr Leu Asn Thr Asp Ser Lys
50                  55                  60

Ser Phe Ser Leu Arg Ile Thr Asp Leu Thr Ile Glu Asp Ser Gly Leu
65                  70                  75                  80

Tyr Arg Cys Lys Thr Trp Pro Val Ser Val Cys Tyr Leu Thr Asn Asn
                85                  90                  95

Glu Arg Asp Leu Tyr Gly Gly Gly Thr Ala Val Thr Val Asn Ala
            100                 105                 110

<210> SEQ ID NO 110
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ala Arg Val Asp Gln Thr Pro Gln Thr Ile Thr Lys Gly Thr Gly Glu
1               5                   10                  15

Ser Leu Thr Ile Asn Cys Val Leu Arg Asp Ser Arg Cys Arg Leu Ser
                20                  25                  30

Ser Thr Asp Trp Tyr Arg Lys Lys Ser Gly Ser Thr Asn Glu Glu Ser
            35                  40                  45

Ile Ser Lys Gly Gly Arg Tyr Val Glu Thr Val Asp Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys His Arg Thr Pro Tyr Val Cys Gly Leu His Ser Gln
                85                  90                  95

His Pro Asp Leu Tyr Gly Gly Gly Thr Val Val Thr Val Asn Ala
            100                 105                 110

<210> SEQ ID NO 111
<211> LENGTH: 111
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 111

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Phe Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ile Arg Val Val Asp Val Cys Trp Leu Glu His Gly
                85                  90                  95

Thr Trp Asp Val Tyr Gly Gly Gly Thr Ala Val Thr Val Asn Ala
            100                 105                 110

<210> SEQ ID NO 112
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Arg Val Asp Gln Thr Pro Gln Thr Ile Thr Lys Glu Thr Gly Glu
1               5                   10                  15

Ser Leu Thr Ile Lys Cys Val Ala Arg Asp Ala His Cys Ala Leu Asp
            20                  25                  30

Arg Thr Tyr Trp Tyr Arg Lys Lys Ser Gly Thr Thr Ile Glu Glu Ser
        35                  40                  45

Ile Pro Ile His Gly Arg Tyr Val Glu Thr Val Asn Ser Gly Gly Lys
    50                  55                  60

Ser Phe Ser Leu Arg Val Asn Asp Leu Ser Val Glu Asp Ser Gly Thr
65                  70                  75                  80

Tyr Arg Cys Lys Ile Lys Ser Phe Ser Asp Cys Asp Leu Gly His Trp
                85                  90                  95

Ala Pro Asp Leu Tyr Gly Gly Gly Thr Ala Val Thr Val Asn Ala
            100                 105                 110

<210> SEQ ID NO 113
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Leu Asn Glu Glu Ser
        35                  40                  45
```

```
Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Phe Arg Gly Tyr Asp Cys Asp Val Met Asp Val
                 85                  90                  95

Phe Gly Gly Val Tyr Gly Gly Thr Val Val Thr Val Asn Ala
                100                 105                 110
```

<210> SEQ ID NO 114
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Val Leu Gly
                 20                  25                  30

Ser Thr Phe Trp His Arg Thr Gln Ser Gly Ser Thr Asn Leu Glu Ser
             35                  40                  45

Ile Phe Ser Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Gln Cys Asn Ile Phe Val Asn Tyr Asp Cys Glu Asp Ala Lys Tyr
                 85                  90                  95

Trp Gln Gly Leu Tyr Gly Gly Thr Ala Val Thr Val Asn Ala
                100                 105                 110
```

<210> SEQ ID NO 115
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Val Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Lys Asn Pro Ser Gly Cys Gly Val Trp Tyr Ser
                 85                  90                  95

Gln Glu Asp Leu Tyr Gly Gly Thr Val Val Thr Val Asn Ala
                100                 105                 110
```

<210> SEQ ID NO 116
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ala Arg Val Asp Gln Thr Pro Gln Thr Ile Thr Lys Glu Thr Gly Glu
1               5                   10                  15

Ser Leu Thr Ile Asn Cys Val Leu Arg Asp Arg Asp Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ala Ile Ile Leu Tyr Gly Cys Glu Leu Thr Ser Asp
                85                  90                  95

Trp Ser Asp Leu Tyr Gly Gly Gly Thr Ala Val Thr Val Asn Ala
            100                 105                 110

<210> SEQ ID NO 117
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ala Arg Val Asp Gln Thr Pro Gln Thr Ile Thr Lys Ala Pro Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Gly
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Ile Val Glu Asp Ser Gly Thr
65                  70                  75                  80

Tyr Arg Cys Lys Leu Arg Thr His Ser Asp Cys Glu Asp Asn Phe Val
                85                  90                  95

Glu Trp Gly Leu Tyr Gly Gly Gly Thr Val Val Thr Val Asn Ala
            100                 105                 110

<210> SEQ ID NO 118
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asp Cys Ala Leu Ser
            20                  25                  30

Ser Thr Tyr Trp Tyr Arg Lys Lys Ser Gly Ser Thr Asn Glu Glu Ser
```

```
                35                  40                  45
Ile Ser Lys Gly Gly Arg Tyr Val Glu Thr Val Asn Ser Gly Ser Lys
 50                  55                  60
Ser Phe Ser Leu Arg Ile Asn Asp Leu Thr Val Glu Asp Ser Gly Thr
 65                  70                  75                  80
Tyr Arg Cys Lys Thr Trp Thr Leu Tyr Asp Cys Asp Tyr Arg Trp Gly
                 85                  90                  95
Asn Gln Asp Leu Tyr Gly Gly Gly Thr Ala Val Thr Val Asn Ala
                100                 105                 110
```

<210> SEQ ID NO 119
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Ala Arg Val Asp Gln Thr Pro Gln Thr Ile Thr Lys Glu Thr Gly Glu
 1                   5                  10                  15
Ser Leu Thr Ile Asn Cys Val Leu Arg Asp Ser Ile Cys Ala Leu Ser
                 20                  25                  30
Ser Thr Tyr Trp Tyr Arg Lys Lys Ser Gly Ser Thr Asn Glu Glu Ser
                 35                  40                  45
Ile Ser Lys Gly Gly Arg Tyr Val Glu Thr Val Asn Ser Gly Ser Lys
 50                  55                  60
Ser Phe Ser Leu Arg Ile Asn Asp Leu Thr Val Glu Asp Ser Gly Thr
 65                  70                  75                  80
Tyr Arg Cys Lys Ser Glu Phe Lys Ser Gly Cys Gly Val Phe Tyr Glu
                 85                  90                  95
Leu Thr Asp Val Tyr Gly Gly Gly Thr Val Val Thr Val Asn Ala
                100                 105                 110
```

<210> SEQ ID NO 120
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Ala Arg Val Asp Gln Thr Pro Gln Thr Ile Thr Lys Glu Thr Gly Glu
 1                   5                  10                  15
Ser Leu Thr Ile Asn Cys Val Leu Arg Asp Ser Asn Cys Ala Leu Ser
                 20                  25                  30
Ser Thr Tyr Trp Tyr Arg Lys Lys Ser Gly Ser Thr Phe Glu Glu Ser
                 35                  40                  45
Ile Ser Lys Gly Gly Arg Tyr Val Glu Thr Val Asn Ser Gly Ser Lys
 50                  55                  60
Ser Phe Ser Leu Arg Ile Asn Asp Leu Thr Val Glu Asp Ser Gly Thr
 65                  70                  75                  80
Tyr Arg Cys Ala Gly Lys Val Phe Tyr Asp Cys Glu Leu Tyr Trp Gly
                 85                  90                  95
Met Thr Asp Val Tyr Gly Gly Gly Thr Val Val Thr Val Asn Ala
                100                 105                 110
```

```
<210> SEQ ID NO 121
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Ala Ile Val Arg Gln Ser Gly Cys Glu Val His Leu Tyr
                85                  90                  95

Gln Arg Asp Leu Tyr Gly Gly Gly Thr Ala Val Thr Val Asn Ala
            100                 105                 110

<210> SEQ ID NO 122
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Val Ser
                20                  25                  30

Ser Thr Tyr Gln Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Ile Asn Leu Ala Tyr Tyr Cys Tyr Leu Asn Phe Glu
                85                  90                  95

Phe Arg Asp Val Tyr Gly Gly Gly Thr Ala Val Thr Val Asn Ala
            100                 105                 110

<210> SEQ ID NO 123
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ala Arg Val Asp Gln Thr Pro Gln Thr Ile Thr Lys Glu Thr Gly Glu
1               5                   10                  15

Ser Leu Thr Ile Lys Cys Val Ala Arg Asp Ala His Cys Ala Leu Asp
                20                  25                  30
```

```
Arg Thr Tyr Trp Tyr Arg Lys Lys Ser Gly Thr Thr Ile Glu Glu Ser
            35                  40                  45

Ile Pro Ile His Gly Arg Tyr Val Glu Thr Val Asn Ser Gly Gly Lys
 50                  55                  60

Ser Phe Ser Leu Arg Val Asn Asp Leu Ser Val Glu Asp Ser Gly Thr
 65                  70                  75                  80

Tyr Arg Cys Lys Met Lys Arg Phe Ser Asp Cys Glu Leu Gly Leu Phe
                85                  90                  95

Ile Glu Asp Val Tyr Gly Gly Gly Thr Val Val Thr Val Asn Ala
            100                 105                 110
```

<210> SEQ ID NO 124
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Ala Arg Val Asp Gln Thr Pro Gln Thr Ile Thr Lys Leu Thr Gly Glu
 1               5                  10                  15

Ser Leu Thr Ile Asn Cys Val Leu Arg Asp Thr Tyr Cys Ala Leu Ser
            20                  25                  30

Asn Thr Asn Trp Tyr His Lys Lys Ser Gly Ser Thr His Glu Glu Ser
            35                  40                  45

Ile Ser Lys Gly Gly Arg Tyr Val Glu Thr Leu Asn Thr Asp Ser Lys
 50                  55                  60

Ser Phe Ser Leu Arg Ile Thr Asp Leu Thr Ile Glu Asp Ser Gly Leu
 65                  70                  75                  80

Tyr Arg Cys Lys Leu His Met Ile Gly Asp Cys Glu Leu Pro Gln Asn
                85                  90                  95

Trp Glu Asp Leu Tyr Gly Gly Gly Thr Ala Val Thr Val Asn Ala
            100                 105                 110
```

<210> SEQ ID NO 125
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
            20                  25                  30

Ser Ala Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Leu Gln Leu Trp Asp Val Cys Gly Asp Asn Trp Glu
                85                  90                  95

Arg Ile Gly Val Tyr Gly Gly Gly Thr Ala Val Thr Val Asn Ala
            100                 105                 110
```

<210> SEQ ID NO 126
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Ile Cys Thr Ala Ser
            20                  25                  30

Asn Thr Tyr Trp Tyr Arg Lys Lys Ser Gly Ser Glu Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Phe Glu Asp Ser Gly Thr
65                  70                  75                  80

Tyr Arg Cys Lys Ser Gln Ser Val Ser Gly Cys Gly Val Trp Ala Asn
                85                  90                  95

Glu Phe Asp Val Tyr Gly Gly Gly Thr Ala Val Thr Val Asn Ala
            100                 105                 110
```

<210> SEQ ID NO 127
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Ala Arg Val Asp Gln Thr Pro Gln Thr Ile Thr Lys Leu Thr Gly Glu
1               5                   10                  15

Ser Leu Thr Ile Asn Cys Val Leu Arg Asp Thr Tyr Cys Ala Leu Ser
            20                  25                  30

Asn Thr Asn Trp Tyr His Lys Lys Ser Gly Ser Thr His Glu Glu Ser
        35                  40                  45

Ile Ser Lys Gly Gly Arg Tyr Val Glu Thr Leu Asn Thr Asp Ser Lys
    50                  55                  60

Ser Phe Ser Leu Arg Ile Thr Asp Leu Thr Ile Glu Asp Ser Gly Leu
65                  70                  75                  80

Tyr Arg Cys Lys Val Ala Arg Thr Ser Gly Cys Tyr Val Trp Ala Trp
                85                  90                  95

Asp Asn Asp Val Tyr Gly Gly Gly Thr Ala Val Thr Val Asn Ala
            100                 105                 110
```

<210> SEQ ID NO 128
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Ala Arg Val Asp Gln Thr Pro Gln Thr Ile Thr Lys Glu Thr Gly Glu
1               5                   10                  15
```

Ser Leu Thr Ile Asn Cys Val Ile Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Tyr Trp Pro Asn Tyr Cys Glu Leu Asp Phe Gly
                85                  90                  95

Glu Arg Asp Leu Tyr Gly Gly Gly Thr Ala Val Thr Val Asn Ala
            100                 105                 110

<210> SEQ ID NO 129
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Gly
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Met Asn Val Trp Tyr Asp Cys Gly Asp Lys Gly Pro
                85                  90                  95

Glu Arg Gly Leu Tyr Gly Gly Gly Thr Ala Val Thr Val Asn Ala
            100                 105                 110

<210> SEQ ID NO 130
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ala Arg Val Asp Gln Thr Pro Gln Thr Ile Thr Lys Asp Ala Gly Glu
1               5                   10                  15

Ser Leu Thr Ile Asn Cys Val Leu Arg Asp Ser Val Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Ala Ala Gly Thr Lys
    50                  55                  60

Ser Phe Ser Leu Arg Ile Asn Asp Leu Arg Val Glu Asp Ser Gly Thr
65                  70                  75                  80

Tyr Arg Cys Ala Ile Val Arg Gln Ser Gly Cys Trp Val Tyr Trp Tyr
                85                  90                  95

```
Glu Thr Gly Val Tyr Gly Gly Gly Thr Val Val Thr Val Asn Ala
            100                 105                 110
```

<210> SEQ ID NO 131
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Gly
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Ser Tyr Tyr Pro Gln Asp Tyr Cys Asp Tyr Phe Gly Asn
                85                  90                  95

Tyr Arg Asp Leu Tyr Gly Gly Thr Val Val Thr Val Asn Ala
            100                 105                 110
```

<210> SEQ ID NO 132
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Asn Trp Tyr Arg Lys Lys Thr Pro Ser Thr Asn Glu Glu Asn
        35                  40                  45

Ile Leu Thr Gly Gly Arg Tyr Val Glu Thr Val Asn Arg Gly Ser Lys
    50                  55                  60

Ser Phe Ser Leu His Ile Asn Asp Leu Thr Ile Glu Asp Ser Gly Thr
65                  70                  75                  80

Tyr Gly Cys Asn Met Val Phe Lys Ser Val Cys Glu Asp Asn Pro Tyr
                85                  90                  95

Gln Tyr Gly Leu Tyr Gly Gly Thr Ala Val Thr Val Asn Ala
            100                 105                 110
```

<210> SEQ ID NO 133
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Ala Arg Val Asp Gln Thr Pro Gln Thr Ile Thr Lys Glu Thr Gly Glu
```

```
             1               5                  10                 15
Ser Leu Thr Ile Lys Cys Val Leu Gln Asn Ser Ile Cys Ala Leu Ser
                    20                  25                  30

Ser Thr Tyr Trp Tyr Trp Lys Lys Ser Gly Ser Ile Asn Glu Glu Glu
            35                  40                  45

Ile Ser Lys Gly Gly Arg Tyr Val Glu Thr Ile Asn Ser Glu Ser Lys
        50                  55                  60

Ser Phe Ser Leu Arg Ile Asn Asp Leu Thr Val Glu Asp Ser Gly Thr
65                  70                  75                  80

Tyr Arg Cys Ala Ile Val Arg Gln Ser Gly Cys Trp Val Thr Thr Ser
                85                  90                  95

Glu Val Asp Leu Tyr Gly Gly Gly Thr Ala Val Thr Val Asn Ala
            100                 105                 110
```

<210> SEQ ID NO 134
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Ala Arg Val Asp Gln Thr Pro Gln Thr Ile Thr Lys Glu Thr Gly Glu
1               5                  10                  15

Ser Ala Thr Ile Asn Cys Glu Leu Gln Asn Ser Phe Cys Arg Leu Ser
                    20                  25                  30

Thr Thr Tyr Trp Tyr Arg Lys Lys Ser Gly Ser Thr Val Glu Glu Thr
            35                  40                  45

Ile Ser Lys Gly Gly Arg Tyr Val Glu Thr Val Ala Arg Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Ile Glu Tyr Leu Gly Tyr Cys Gly Leu Trp Asn Lys
                85                  90                  95

Phe Tyr Gly Leu Tyr Gly Gly Thr Val Val Thr Val Asn Ala
            100                 105                 110
```

<210> SEQ ID NO 135
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

```
Ala Arg Val Asp Gln Thr Pro Gln Thr Ile Thr Lys Glu Thr Gly Glu
1               5                  10                  15

Ser Leu Thr Ile Asn Cys Val Leu Arg Asp Ser Ile Cys Ala Leu Ser
                    20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Val Ile Trp Ala His Ser Gly Cys Glu Val Ile Thr His
```

85                  90                  95

Ala Met Asp Leu Tyr Gly Gly Gly Thr Ala Val Thr Val Asn Ala
            100                 105                 110

<210> SEQ ID NO 136
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Gly
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Thr Leu Tyr Trp Ser Tyr Cys Asp Leu Arg Thr Gly
                85                  90                  95

Ile His Asp Leu Tyr Gly Gly Gly Thr Ala Val Thr Val Asn Ala
            100                 105                 110

<210> SEQ ID NO 137
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Arg Trp Val Gly Arg Leu Tyr Cys Gly Asp Asn Glu Trp
                85                  90                  95

Met Gln Asp Leu Tyr Gly Gly Gly Thr Ala Val Thr Val Asn Ala
            100                 105                 110

<210> SEQ ID NO 138
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Trp
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Met Arg Glu Pro Leu Asp Cys Gly Leu Pro Asn Trp
                85                  90                  95

Met Tyr Gly Leu Tyr Gly Gly Gly Thr Ala Val Thr Val Asn Ala
                100                 105                 110

<210> SEQ ID NO 139
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Ser Tyr Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Thr Arg Arg Ile Asp Val Cys Glu Val Lys Tyr Glu
                85                  90                  95

Phe Gly Asp Val Tyr Gly Gly Gly Thr Ala Val Thr Val Asn Ala
                100                 105                 110

<210> SEQ ID NO 140
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ala Arg Val Asp Gln Thr Pro Gln Ala Ile Thr Lys Glu Thr Gly Glu
1               5                   10                  15

Ser Leu Thr Ile Asn Cys Ala Leu Arg Asp Thr Asn Cys Ala Leu Pro
            20                  25                  30

Gly Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80
```

Tyr Arg Cys Lys Val Ala Arg Thr Ser Gly Cys Trp Val Trp Tyr
                85                  90                  95

Glu Thr Gly Val Tyr Gly Gly Thr Ala Val Thr Val Asn Ala
            100                 105                 110

<210> SEQ ID NO 141
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Ser Tyr Glu Glu Ser
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Asn Arg Gln Met Asp Val Cys Trp Leu Glu His Gly
                85                  90                  95

Thr Trp Asp Val Tyr Gly Gly Thr Ala Val Thr Val Asn Ala
            100                 105                 110

<210> SEQ ID NO 142
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Arg Val Asp Gln Thr Pro Gln Thr Ile Thr Lys Glu Thr Gly Glu
1               5                   10                  15

Ser Leu Thr Ile Asn Cys Val Val Arg Asp Ser Asn Cys Pro Leu Ala
                20                  25                  30

Ala Thr Tyr Trp Tyr Arg Lys Lys Ser Ala Ser Thr Asn Glu Glu Ser
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Gln Cys Arg Ile Arg Ser Thr Asp Val Cys Tyr Asp Ala Met Gln
                85                  90                  95

Glu Thr Gly Leu Tyr Gly Gly Gly Thr Val Val Thr Val Asn Ala
            100                 105                 110

<210> SEQ ID NO 143
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Arg Val Asp Gln Thr Pro Gln Thr Ile Thr Lys Leu Thr Gly Glu
1               5                   10                  15

Ser Leu Thr Ile Asn Cys Val Leu Arg Asp Thr Tyr Cys Ala Leu Ser
                20                  25                  30

Asn Thr Asn Trp Tyr His Lys Lys Ser Gly Ser Thr His Glu Glu Ser
            35                  40                  45

Ile Ser Lys Gly Gly Arg Tyr Val Glu Thr Leu Asn Thr Asp Ser Lys
        50                  55                  60

Ser Phe Ser Leu Arg Ile Thr Asp Leu Thr Ile Glu Asp Ser Gly Leu
65                  70                  75                  80

Tyr Arg Cys Lys Ala Lys Gly Trp Gly Asp Cys Tyr Tyr Lys Trp Thr
                85                  90                  95

Val Asn Asp Val Tyr Gly Gly Gly Thr Val Val Thr Val Asn Ala
                100                 105                 110

<210> SEQ ID NO 144
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Arg Val Asp Gln Thr Pro Gln Thr Leu Thr Lys Glu Thr Gly Glu
1               5                   10                  15

Ser Leu Thr Ile Asn Cys Val Leu Arg Gly Ala Asn Cys Ala Phe Asp
                20                  25                  30

Arg Thr Tyr Trp Tyr Arg Lys Lys Ser Gly Ser Thr Arg Glu Glu Ser
            35                  40                  45

Ile Ser Lys Gly Gly Arg Tyr Val Glu Thr Val Asn Ser Gly Ser Lys
        50                  55                  60

Ser Phe Ser Leu Thr Ile Asn Asp Leu Thr Ile Glu Asp Ser Gly Thr
65                  70                  75                  80

Tyr Arg Cys Ala Lys Arg Trp Ile Ser Gly Cys Asp Val Pro Val Leu
                85                  90                  95

Ala Pro Asp Leu Tyr Gly Gly Gly Thr Ala Val Thr Val Asn Ala
                100                 105                 110

<210> SEQ ID NO 145
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr His Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Ile Arg Gln Val Leu Asp Cys Gly Tyr Phe Thr Gly
                85                  90                  95

Asp Trp Asp Leu Tyr Gly Gly Gly Thr Ala Val Thr Val Asn Ala
            100                 105                 110

<210> SEQ ID NO 146
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
                20                  25                  30

Thr Thr His Trp Tyr Arg Lys Lys Ser Asp Ser Thr Asn Glu Glu Ser
            35                  40                  45

Ile Ser Lys Gly Gly Arg Tyr Val Glu Thr Val Ser Ser Gly Ser Lys
        50                  55                  60

Ser Phe Ser Leu Arg Ile Asn Asp Leu Thr Ile Glu Asp Ser Gly Thr
65                  70                  75                  80

Tyr Arg Cys Asn Lys Tyr Glu Phe Gly Asp Cys Asp Leu Thr Asn Lys
                85                  90                  95

Trp Met Asp Val Tyr Gly Gly Gly Thr Ala Val Thr Val Asn Ala
            100                 105                 110

<210> SEQ ID NO 147
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ala Arg Val Asp Gln Thr Pro Gln Thr Ile Thr Lys Glu Thr Gly Glu
1               5                   10                  15

Ser Leu Thr Ile Asn Cys Val Leu Val Asp Ser Asn Cys Ala Glu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Ala Trp Glu Gly Ser Trp Cys Trp Val Gln Phe Leu
                85                  90                  95

Gln Pro Gly Leu Tyr Gly Gly Gly Thr Ala Val Thr Val Asn Ala
            100                 105                 110

<210> SEQ ID NO 148
<211> LENGTH: 111
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 148

Ala Arg Val Asp Gln Thr Pro Gln Ser Ile Thr Lys Gln Thr Gly Glu
1               5                   10                  15

Ser Leu Thr Ile Asn Cys Val Leu Gly Asp Ser Gln Cys Pro Val Glu
            20                  25                  30

Glu Thr Trp Trp Tyr Arg Lys Lys Thr Gly Ser Thr Asn Glu Glu Arg
        35                  40                  45

Ile Ser Lys Arg Gly Arg Tyr Val Glu Thr Ile Asn Ser Gly Gly Lys
    50                  55                  60

Ser Phe Ser Leu Arg Ile Asn Asp Leu Thr Val Glu Asp Ser Gly Thr
65                  70                  75                  80

Tyr Thr Cys Lys Thr Asp Phe Gly Gly Val Cys Trp Asp Ile Trp His
                85                  90                  95

Pro Pro Gly Leu Tyr Gly Gly Gly Thr Val Val Thr Val Asn Ala
            100                 105                 110

<210> SEQ ID NO 149
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ala Arg Val Asp Gln Thr Pro Gln Thr Ile Thr Lys Leu Thr Gly Glu
1               5                   10                  15

Ser Leu Thr Ile Asn Cys Val Leu Arg Asp Thr Tyr Cys Ala Leu Ser
            20                  25                  30

Asn Thr Asn Trp Tyr His Lys Lys Ser Gly Ser Thr His Glu Glu Ser
        35                  40                  45

Ile Ser Lys Gly Gly Arg Tyr Val Glu Thr Leu Asn Thr Asp Ser Lys
    50                  55                  60

Ser Phe Ser Leu Arg Ile Thr Asp Leu Thr Ile Glu Asp Ser Gly Leu
65                  70                  75                  80

Tyr Arg Cys Lys Thr Leu Ser Phe Tyr Val Cys Asp Leu Phe Leu Trp
                85                  90                  95

Gly Gly Asp Val Tyr Gly Gly Gly Thr Val Val Thr Val Asn Ala
            100                 105                 110

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Ser Ile Cys Ala Leu Ser Ser
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Asp Ser Asn Cys Ala Leu Pro Ser
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Ser Val Cys Ala Leu Ser Ser
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Ser Asn Cys Ala Leu Ser Ser
1               5

<210> SEQ ID NO 154
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Val His Met Glu Asp Met Asn Val Arg Asp Tyr Gly Gly Phe Trp Gly
1               5                   10                  15

Glu Asp Val

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Val Asn Leu Arg Ser Val Leu Pro Cys Gly Trp Pro Asp Val
1               5                   10

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Val Glu Asn Leu Pro Gly Ser Gly Ser Cys Leu Arg Tyr Tyr Leu Ser
1               5                   10                  15

Asp Val

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Val Arg Glu Trp Ala Cys Glu Asp Asp Gly Arg Val Trp Gly Trp Glu
1               5                   10                  15

Asp Val

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Ala Arg Thr Ser Gly Cys Glu Val Tyr Thr Tyr Thr Gly Asp Val
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Val Lys Asn Pro Ser Gly Cys Gly Val Trp Tyr Ser Gln Glu Asp Leu
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Glu Phe Lys Ser Gly Cys Gly Val Phe Tyr Glu Leu Thr Asp Val
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Met Val Phe Lys Ser Val Cys Glu Asp Asn Pro Tyr Gln Tyr Gly Leu
1               5                   10                  15

<210> SEQ ID NO 162
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 162

Ile Trp Ala His Ser Gly Cys Glu Val Ile Thr His Ala Met Asp Leu
1               5                   10                  15

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Thr Asn Glu Glu Asn Ile Ser Lys Gly
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Thr Asn Glu Glu Ser Ile Ser Lys Gly
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Lys Glu Glu Ser Ile Ser Lys Gly
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Asn Glu Glu Asn Ile Leu Thr Gly
1               5

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Gly Ser Lys Ser
1               5
```

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Gly Ser Lys Ser
1               5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 169

His His His His His His
1               5

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Gly Gly Gly Ser
1               5

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gaccccaaaa tcagcgaaat                                              20

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tctggttact gccagttgaa tctg                                         24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173

```
acccegcatt acgtttggtg gacc                                              24

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
agatttggac ctgcgagcg                                                    19

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gagcggctgt ctccacaagt                                                   20

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
ttctgacctg aaggctctgc gcg                                               23
```